(12) United States Patent
Xu et al.

(10) Patent No.: US 11,604,197 B2
(45) Date of Patent: *Mar. 14, 2023

(54) REAL TIME ELECTRONIC CELL SENSING SYSTEMS AND APPLICATIONS FOR CELL-BASED ASSAYS

(71) Applicant: Agilent Technologies, Inc., Santa Clara, CA (US)

(72) Inventors: Xiao Xu, San Diego, CA (US); Yama A. Abassi, San Diego, CA (US); Xiaobo Wang, San Diego, CA (US); Jiangbo Gan, San Diego, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 378 days.

This patent is subject to a terminal disclaimer.

(21) Appl. No.: 16/833,180

(22) Filed: Mar. 27, 2020

(65) Prior Publication Data
US 2020/0348312 A1 Nov. 5, 2020

Related U.S. Application Data

(60) Division of application No. 15/487,349, filed on Apr. 13, 2017, now Pat. No. 10,690,677, which is a continuation of application No. 13/244,004, filed on Sep. 23, 2011, now Pat. No. 9,625,472, which is a division of application No. 11/725,040, filed on Mar. 15, 2007, now Pat. No. 8,026,080, which is a division of application No. 10/987,732, filed on Nov. 12, 2004, now Pat. No. 7,192,752, which is a continuation-in-part of application No. 10/705,615, filed on Nov. 10, 2003, now Pat. No. 7,459,303, and a continuation-in-part of application No. 10/705,447, filed on Nov. 10, 2003, now Pat. No. 7,470,533.

(60) Provisional application No. 60/548,713, filed on Feb. 27, 2004, provisional application No. 60/542,927, filed on Feb. 9, 2004, provisional application No. 60/519,567, filed on Nov. 12, 2003, provisional application No. 60/469,572, filed on May 9, 2003, provisional application No. 60/435,400, filed on Dec. 20, 2002.

(51) Int. Cl.
| | |
|---|---|
| G01N 33/68 | (2006.01) |
| C12M 1/12 | (2006.01) |
| C12M 1/34 | (2006.01) |
| G01N 33/50 | (2006.01) |
| G01N 33/483 | (2006.01) |

(52) U.S. Cl.
CPC ......... *G01N 33/6854* (2013.01); *C12M 25/08* (2013.01); *C12M 41/36* (2013.01); *G01N 33/4836* (2013.01); *G01N 33/5005* (2013.01); *G01N 2500/10* (2013.01)

(58) Field of Classification Search
None
See application file for complete search history.

(56) References Cited

U.S. PATENT DOCUMENTS

| | | |
|---|---|---|
| 2,656,508 A | 10/1953 | Coulter |
| 3,259,842 A | 7/1966 | Coulter et al. |
| 3,743,581 A | 7/1973 | Cady et al. |
| 3,890,201 A | 6/1975 | Cady |
| 4,072,578 A | 2/1978 | Cady et al. |
| 4,225,410 A | 9/1980 | Pace |
| 4,559,310 A | 12/1985 | Cantor et al. |
| 4,686,190 A | 8/1987 | Cramer et al. |
| 4,920,047 A | 4/1990 | Giaever et al. |
| 5,001,048 A | 3/1991 | Taylor et al. |
| 5,134,070 A | 7/1992 | Casnig |
| 5,187,096 A | 2/1993 | Giaever et al. |
| 5,218,312 A | 6/1993 | Moro |
| 5,247,827 A | 9/1993 | Shah |
| 5,278,048 A | 1/1994 | Parce et al. |
| 5,284,753 A | 2/1994 | Goodwin, Jr. |
| 5,514,555 A | 5/1996 | Springer et al. |
| 5,563,067 A | 10/1996 | Sugihara et al. |
| 5,601,997 A | 2/1997 | Tchao |
| 5,622,872 A | 4/1997 | Ribi |
| 5,626,734 A | 5/1997 | Docoslis et al. |
| 5,643,742 A | 7/1997 | Malin et al. |
| 5,725,563 A | 3/1998 | Klotz |

(Continued)

FOREIGN PATENT DOCUMENTS

| | | |
|---|---|---|
| EP | 1138758 A1 | 10/2001 |
| EP | 1195432 B1 | 6/2004 |

(Continued)

OTHER PUBLICATIONS

PCT/US2004/037696 International Search Report dated May 16, 2005.
Cartellieri et al. "Chimeric Antigen Receptor-Engineered T Cells for Immunotherapy of Cancer." Journal of Biomedicine and Biotechnology, 2010; 2010:1-13.
Aravanis et al. "A Genetically Engineered Cell-Based Biosensor for Functional Classification of Agents." Biosensors & Bioelectronics, 2001, 16:571-577.
Banach et al. "Development of Electrical Activity in Cardiac Myocyte Aggregates Derived from Mouse Embryonic Stem Cells." Amerocam Journal of Physiology-Heart Circulatoy Physiology, 2003, 284: H2114-H2123.

(Continued)

*Primary Examiner* — William H. Beisner

(57) ABSTRACT

Methods for identifying compounds that modulate cellular responses stimulated by IgE, which include providing an impedance-based system that monitors cell-substrate impedance of cells on a substrate; introducing cells to the substrate of the system; adding at least one test compound and IgE to the cells, wherein the at least one test compound is suspected of modulating cell responses stimulated by the IgE; adding an antigen to the cells; monitoring the cell-substrate impedance of cells on the substrate; and analyzing the cell-substrate impedance to evaluate whether the at least one test compound alters a cellular response to stimulation with the IgE.

15 Claims, 26 Drawing Sheets

(56) References Cited

U.S. PATENT DOCUMENTS

| | | |
|---|---|---|
| 5,766,934 A | 6/1998 | Guiseppi-Elie |
| 5,800,467 A | 9/1998 | Park et al. |
| 5,801,055 A | 9/1998 | Henderson |
| 5,810,725 A | 9/1998 | Sugihara et al. |
| 5,824,494 A | 10/1998 | Feldberg |
| 5,851,489 A | 12/1998 | Wolf et al. |
| 5,981,268 A | 11/1999 | Kovacs et al. |
| 6,033,628 A | 3/2000 | Kaltenback et al. |
| 6,051,422 A | 4/2000 | Kovacs et al. |
| 6,132,683 A | 10/2000 | Sugihara et al. |
| 6,169,394 B1 | 1/2001 | Frazier et al. |
| 6,232,062 B1 | 5/2001 | Kayyem et al. |
| 6,235,520 B1 | 5/2001 | Malin et al. |
| 6,280,586 B1 | 8/2001 | Wolf et al. |
| 6,288,527 B1 | 9/2001 | Sugihara et al. |
| 6,368,795 B1 | 4/2002 | Hefti et al. |
| 6,368,851 B1 | 4/2002 | Baumann et al. |
| 6,376,233 B1 | 4/2002 | Wolf et al. |
| 6,377,057 B1 | 4/2002 | Borkholder et al. |
| 6,440,662 B1 | 8/2002 | Van Gerwen et al. |
| 6,448,030 B1 | 9/2002 | Rust et al. |
| 6,448,794 B1 | 9/2002 | Cheng et al. |
| 6,461,808 B1 | 10/2002 | Bodner et al. |
| 6,472,144 B2 | 10/2002 | Malin et al. |
| 6,485,905 B2 | 11/2002 | Hefti |
| 6,492,175 B1 | 12/2002 | Mueller et al. |
| RE37,977 E | 2/2003 | Sugihara et al. |
| 6,535,822 B2 | 3/2003 | Mansky et al. |
| 6,566,079 B2 | 5/2003 | Hefti |
| 6,573,063 B2 | 6/2003 | Hochman |
| 6,596,499 B2 | 7/2003 | Jalink |
| 6,626,902 B1 | 9/2003 | Kucharczyk et al. |
| 6,627,461 B2 | 9/2003 | Chapman et al. |
| 6,630,359 B1 | 10/2003 | Caillat et al. |
| 6,637,257 B2 | 10/2003 | Sparks |
| 6,638,743 B2 | 10/2003 | Baumann et al. |
| RE38,323 E | 11/2003 | Sugihara et al. |
| 6,649,402 B2 | 11/2003 | Van der Weide et al. |
| 6,686,193 B2 | 2/2004 | Maher et al. |
| 6,716,620 B2 | 4/2004 | Bashir et al. |
| 6,723,523 B2 | 4/2004 | Lynes et al. |
| 6,803,229 B2 | 10/2004 | Martin et al. |
| 6,835,552 B2 | 12/2004 | Miles et al. |
| 6,846,639 B2 | 1/2005 | Miles et al. |
| 6,852,525 B1 | 2/2005 | Cantor |
| 6,998,249 B1 | 2/2006 | McKim et al. |
| 7,010,347 B2 | 3/2006 | Schecter |
| 7,148,059 B1 | 12/2006 | Tillotson et al. |
| 7,192,752 B2 | 3/2007 | Xu et al. |
| 7,208,279 B2 | 4/2007 | Gilchrist et al. |
| 7,294,334 B1 | 11/2007 | Michal et al. |
| 7,399,631 B2 | 7/2008 | Giaever et al. |
| 7,459,303 B2 | 12/2008 | Wang et al. |
| 7,468,255 B2 | 12/2008 | Xu et al. |
| 7,470,533 B2 | 12/2008 | Xu et al. |
| 7,476,827 B1 | 1/2009 | Bhullar et al. |
| 7,510,699 B2 | 3/2009 | Black et al. |
| 7,553,448 B2 | 6/2009 | Kumar et al. |
| 7,560,269 B2 | 7/2009 | Wang et al. |
| 7,732,127 B2 | 6/2010 | Wang et al. |
| 7,842,246 B2 | 11/2010 | Wohlstadter et al. |
| 7,876,108 B2 | 1/2011 | Abassi et al. |
| 8,026,080 B2 | 9/2011 | Wang et al. |
| 8,041,515 B2 | 10/2011 | Wang et al. |
| 8,206,903 B2 | 6/2012 | Wang et al. |
| 8,263,375 B2 | 9/2012 | Abassi et al. |
| 8,344,742 B2 | 1/2013 | Abassi et al. |
| 8,420,363 B2 | 4/2013 | Wang et al. |
| 8,916,357 B2 | 12/2014 | Abassi et al. |
| 8,921,041 B2 | 12/2014 | Wang et al. |
| 9,399,787 B2 | 7/2016 | Abassi et al. |
| 9,612,234 B2 | 4/2017 | Li et al. |
| 9,625,472 B2 | 4/2017 | Xu et al. |
| 9,709,548 B2 | 7/2017 | Wang et al. |
| 10,012,636 B2 | 7/2018 | Wang et al. |
| 10,067,121 B2 | 9/2018 | Abassi et al. |
| 10,533,985 B2 | 1/2020 | Wang et al. |
| 2002/0010492 A1 | 1/2002 | Donovan et al. |
| 2002/0032531 A1 | 3/2002 | Mansky et al. |
| 2002/0076690 A1 | 6/2002 | Miles et al. |
| 2002/0086280 A1 | 7/2002 | Lynes et al. |
| 2002/0090649 A1 | 7/2002 | Chan et al. |
| 2002/0110847 A1 | 8/2002 | Baumann et al. |
| 2002/0150886 A1 | 10/2002 | Miles et al. |
| 2003/0032000 A1 | 2/2003 | Liu et al. |
| 2003/0072549 A1 | 4/2003 | Facer et al. |
| 2003/0104512 A1 | 6/2003 | Freeman et al. |
| 2003/0116447 A1 | 6/2003 | Surridge et al. |
| 2003/0143625 A1 | 7/2003 | Martin et al. |
| 2003/0157587 A1 | 8/2003 | Gomez et al. |
| 2003/0166015 A1 | 9/2003 | Zarowitz et al. |
| 2003/0166018 A1* | 9/2003 | Wabl ............... G01N 33/5047 435/7.21 |
| 2003/0211500 A1 | 11/2003 | Woosley |
| 2004/0091397 A1 | 5/2004 | Picard |
| 2004/0106095 A1 | 6/2004 | Thomson et al. |
| 2004/0146849 A1 | 7/2004 | Huang et al. |
| 2004/0152067 A1 | 8/2004 | Wang et al. |
| 2005/0014130 A1 | 1/2005 | Liu et al. |
| 2005/0153425 A1 | 7/2005 | Xu et al. |
| 2005/0182447 A1 | 8/2005 | Schecter |
| 2005/0287065 A1 | 12/2005 | Suddarth et al. |
| 2006/0023559 A1 | 2/2006 | Xu et al. |
| 2006/0050596 A1 | 3/2006 | Abassi et al. |
| 2006/0057771 A1 | 3/2006 | Kovacs et al. |
| 2006/0121446 A1 | 6/2006 | Abassi et al. |
| 2006/0161073 A1 | 7/2006 | Singer |
| 2006/0216203 A1 | 9/2006 | Fuller et al. |
| 2006/0240490 A1 | 10/2006 | Lee |
| 2006/0252054 A1 | 11/2006 | Lin et al. |
| 2007/0042347 A1 | 2/2007 | Rosen et al. |
| 2007/0087333 A1 | 4/2007 | Gruters et al. |
| 2007/0172939 A1 | 7/2007 | Xu et al. |
| 2007/0212423 A1 | 9/2007 | Epstein et al. |
| 2008/0190783 A1 | 8/2008 | Hyland |
| 2008/0286750 A1 | 11/2008 | Xu et al. |
| 2009/0017465 A1 | 1/2009 | Xu |
| 2009/0142790 A1 | 6/2009 | Fang et al. |
| 2009/0155821 A1 | 6/2009 | Kunich et al. |
| 2009/0241698 A1 | 10/2009 | Biksacky |
| 2009/0325213 A1 | 12/2009 | Gambari et al. |
| 2010/0029506 A1 | 2/2010 | Wang et al. |
| 2011/0039294 A1 | 2/2011 | Wang et al. |
| 2011/0231103 A1 | 9/2011 | Fang |
| 2011/0300569 A1 | 12/2011 | Li et al. |
| 2012/0142031 A1 | 6/2012 | Xu et al. |
| 2012/0295253 A1 | 11/2012 | Abassi et al. |
| 2012/0322050 A1 | 12/2012 | Abassi et al. |
| 2013/0123136 A1 | 5/2013 | Abassi et al. |
| 2014/0203818 A1 | 7/2014 | Wang et al. |
| 2015/0125894 A1 | 5/2015 | Laing et al. |
| 2015/0185206 A1 | 7/2015 | Abassi et al. |
| 2015/0218549 A1 | 8/2015 | Li et al. |
| 2015/0231634 A1 | 8/2015 | Szita et al. |
| 2017/0205391 A1 | 7/2017 | Li et al. |
| 2017/0269062 A1 | 9/2017 | Abassi et al. |
| 2017/0315131 A1 | 11/2017 | Xu et al. |
| 2017/0370907 A1 | 12/2017 | Abassi et al. |
| 2018/0246079 A1 | 8/2018 | Wang et al. |
| 2019/0195861 A1 | 6/2019 | Abassi et al. |
| 2020/0071672 A1 | 3/2020 | Zhang et al. |

FOREIGN PATENT DOCUMENTS

| | | |
|---|---|---|
| EP | 1040345 B1 | 3/2006 |
| EP | 2213721 | 8/2010 |
| EP | 2291645 | 9/2015 |
| WO | 1996/001836 A1 | 1/1996 |
| WO | 1999/066329 A1 | 12/1999 |
| WO | 2000/037628 A1 | 6/2000 |
| WO | 2000/070343 A2 | 11/2000 |
| WO | 2000/071669 A1 | 11/2000 |
| WO | 2001/025769 A3 | 4/2001 |
| WO | 2001/038873 A3 | 5/2001 |

(56) References Cited

FOREIGN PATENT DOCUMENTS

| | | |
|---|---|---|
| WO | 2001/079529 A1 | 10/2001 |
| WO | 2002/004943 A3 | 1/2002 |
| WO | 2002/042766 A3 | 5/2002 |
| WO | 2003/0016887 A3 | 2/2003 |
| WO | 2004/010103 A2 | 1/2004 |
| WO | 2005/005979 A1 | 1/2005 |
| WO | 2005/047482 A2 | 5/2005 |
| WO | 2005/077104 A2 | 8/2005 |
| WO | 2006/015387 A2 | 2/2006 |
| WO | 2006/017762 A2 | 2/2006 |
| WO | 2009/137440 A1 | 11/2009 |
| WO | 2010/129725 A1 | 11/2010 |
| WO | 2011/146531 A1 | 11/2011 |
| WO | 2012/043820 A1 | 4/2012 |
| WO | 2014/085727 A1 | 6/2014 |
| WO | 2016183143 A1 | 11/2016 |
| WO | 2017/068421 A1 | 4/2017 |
| WO | 2017/087945 A1 | 5/2017 |

OTHER PUBLICATIONS

Baumann et al., "Microelectronic Sensor System for Microphysical Application on Living Cells", Sensors and Actuators, 1999:77-89.

Becker et al. "Separation of Human Breast Cancer Cells from Blood by Differential Dielectric Affinity." Cell Biology, 1995, 92:960-964.

Berdondini et al. "High-Density Electrode Array for Imaging in Vitro Electrophysiological Activity." Biosensors and Bioelectronics, 2005, 21:167-174.

Berens et al. "The Role of Extracelluar Matrix in Human Astrocytoma Migration and Proliferation Studied in a Microliter Scale Assay." Clinical and Experimental Metastasis, 1994; 12(6):405-415.

Bergveld, P. "A Critical Evaluation of Direct Electrical Protein Detection Methods." Biosensors & Bioelectronics. 6:55-72 (1991).

Bieberich et al. "Neuronal Differentiation and Synapse Formation of PC12 and Embryonic Stem Cells on Interdigitated Microelectrode Arrays," Biosensors and Bioelectronics 2004; 19:923-931.

Blagbrough et al. "Polyamines and Novel Polyamine Conjugates Interact with DNA in Ways That Can Be Exploited in Non-Viral Gene Therapy." Biochemical Society Transactions, 2003, 31, Part 2, pp. 397-406.

Bonetta, Laura. "The Inside Scoop-Evaluating Gene Delivery Methods." Nature Methods, Nov. 2005, 2 (11):875-883.

Burnett et al. "Fluorescent Imaginng of Electrically Stimulated Cells." Journal of Biomolecular Screening 2003; 8 (6):660-667.

Burns et al. "Neutrophil Transendothelial Migration Is Independent of Tight Junctions and Occurs Preferentially at Tricellular Corners." Journal of Immunology, 1997, 2893-2903.

Cady et al. "Electrical Impedance Measurements: Rapid Method for Detecting and Monitoring Microorganisms," Journal of Clinical Mirobiology, 1978; 7(3):265-272.

Cartellieri et al. "Chimeric Antigen Receptor—Engineered T Cells for Immunotherapy of Cancer." Journal of Biomedicine and Biotechnology, 2010, 1-13.

Chang et al. "Impedimetric Monitoring of Cell Attachment on Interdigitated Microelectrodes." Sensors and Actuators, 2005, B 105:159-163.

Ciambrone et al. "Cellular Dielectric Spectroscopy: A Powerful New Approach to Label-Free Cellular Analysis." Journal of Biomolecular Screening, 2004, 9(6):467-480.

Connolly et al. "An Extracellular Microelectrode Array for Monitoring Electrogenic Cells in Culture," Biosensors and Biolectronics, 1190, 5:223-234.

Duan et al. "Separation-Free Sandwich Enzyme Immunoassays Using Microporous Gold Electrodes and Self-Assembled Monolayer/Immobilized Capture Antibodies." Analytical Chemistry, 1994, 66:1369-1377.

Ehret et al. "Monitoring of Cellular Behaviour by Impedance Measurements on Interdigitated Electrode Structures." Biosensors and Bioelectronics 1997; 12(1):29-41.

Ehret et al. "On-Line Control of Cellular Adhesion with Impedance Measurements Using Interdigitated Electrode Structures", Medical & Biological Engineering & Computing, 1998; 36:365-370.

Falk et al. "A 48-well Micro Chemotaxis Assembly for Rapid and Accurate Measurement of Leukocyte Migration." Journal of Immunological Methods., 1980, 33:239-247.

Fuhr et al. "Positioning and Manipulation of Cells and Microparticles Using Miniaturized Electric Field Traps and Travelling Waves." Sensors and Materials 7(2):131-146 (1995).

Fusenig et al. "The Need for a Worldwide Consensus for Cell Line Authentication: Experience Implementing a Mandatory Requirement at the Internation Journal of Cancer". PLOS Biologiy, Apr. 17, 2017, 15(4) p. e2001438 pp. 1-13.

Giaever et al, "Monitoring Fibroblast Behavior in Tissue Culture with an Applied Electric Field." Proceedings of the National Academy of Sciences. USA; 1984; 81(Jun.):3761-3764.

Giaever et al. "Micromotion of Mammalian Cells Measured Electrically." Proceedings of the National Academy of Sciences, USA, 1991; 8(Sep.):7896-7900.

Gutmann et al. "Evidence for Different ABC-Transporters in Caco-2 Cells Modulating Drug Uptake." Pharmaceutical Research, 1999, 16(3):402-407.

Hadjout et al. "Automated Real-Time Measurement of Chemotactic Cell Motility." BioTechniques, 2001, 31:1130-1138.

Hapala, Ivan. "Breaking the Barrier: Methods for Reversible Permeabilization of Cellular Membranes." Critical Reviews in Biotechnology, 1997, 17(2):105-122.

Henning et al. "Approach to a Mutliparametric Sensor-Chip-Based Tumor Chemosensitivity Assay," Anti-Cancer Drugs 2001; 12:21-32.

Hescheler et al. "Determination of Electrical Properties of ES Cell-derived Cardiomyocytes Using MEAs." Journal of Electrocardiology, 2004, vol. 37, Suppl.

Hidalgo et al. "Characterization of the Human Colon Carcinoma Cell Line (Caco-2) as a Model System for Intestinal Epithelial Permeability," Gastroenterology, 1989; 96:736-749.

Horvath et al. "Monitoring of Living Cell Attachment and Spreading Using Reverse Symmetry Waveguide Sensing." Applied Physics Letters, 2005, 86:071101.

Huang et al. "Dielectrophoretic Cell Separation and Gene Expression Profiling on Microelectronic Chip Arrays." Analytical Chemistry, 2002, 74:3362-3371.

Hug, Thomas, "Biophysical Methods for Monitoring Cell-Substrate Interactions in Drug Discovery." Assay and Drug Development Technologies, 2003; 1(3):479-488.

Keese et al. "Real-time Impedance Assay to Follow the Invasive Activities of Metastatic Cells in Culture." BioTechniques, 2002, 33:842-850.

Klauke et al. "Extracellular Recordings of Field Potentials from Single Cardiomyocytes." Biophysical Journal, Oct. 2006, 91:2543-2551.

Kleinman et al. "Basement Membrane Complexes with Biological Activity." Biochemistry 1986; 25(2):312-318.

Kloss et al. "Microcavity Array (MCA)-Based Biosensor Chip for Functional Drug Screening of 3D Tissue Models." Biosensors and Bioelectronics, 2008, 23:1473-1480.

Kowolenko et al. "Measurement of Macrophage Adherence and Spreading with Weak Electric Fields." Journal of Immunological Methods, 1990; 127:71-77.

Larsen et al. "Somatic Cell Counting with Silicon Apertures." Micro Total Analysis Systems, 2000, 103-106.

Lin et al. "Electroporation Microchips for In Vitro Gene Transfection." Journal of Micromechanics and Microengineering, 2001, 11:542-547.

Lin et al. "Simulation and Experimental Demonstration of the Electric Field Assisted Electroporation Microchip for In Vitro Gene Delivery Enhancement." Miniaturisation for Chemistry, Biology & Bioengineerin., 2004, 4:104-108.

Lo et al. American Physical Society March Meeting 2010, Portland Oregon, vol. 55, No. 2, Poter Session Abstract, BAPS, Mar. 2010 C1 268.

Lo et al. "Monitoring Motion of Confluent Cells in Tissue Culture." Experimental Cell Research 1983; 204:102-109.

(56) References Cited

OTHER PUBLICATIONS

Lo et al. "Impedance Analysis of MDCK Cells Measured by Electric Cell-Substrate Impedance Sensing." Biophysical Journal, 1995, 69:2800-2807.
Lo et al. "pH Changes in pulsed CO2 incubators cause periodic changes in cell morphology ." Experimental Cell Research, 1994, 213:391-397.
Loffert et al. "Multiplex PCR with QIAGEN: Tag DNA Plymerase and PCR Buffer." QIAGENews, 1994, 4:15-18.
Luan et al. "Clustering of Time-Course Gene Expression Data Using a Mixed-Effects Model with B-Splines." Bioinformatics, 2003, 19(4):474-482.
Luong et al. "Monitoring Motility, Spreading and Mortality of Adherent Insect Cells Using an Impedance Sensor ", Analytical Chemistry, 2001, 73(8):1844-1848.
Mitra et al. "Electric Measurements Can Be Used to Monitor the Attachment and Spreading of Cells in Tissue Culture." Biotechniques, 1991, 11(4):504-510.
EP05786773 Extended European Search Report dated Mar. 21, 2013.
EP05852157 Extended European Search Report dated Sep. 13, 2011.
EP058122680 Extended European Search Report dated Sep. 7, 2011.
EP03748948 Extended European Search Report dated Mar. 12, 2007.
EP09743420 European Search Report dated Nov. 26, 2013.
EP10772804.0 Extended European Search Report dated Oct. 27, 2017.
PCT/US2009/033801 International Search Report and Written Opinion dated Jul. 9, 2010.
PCT/US2009/042787 International Search Report and Written Opinion dated Jun. 24, 2009.
PCT/US2011/036877 International Search Report dated Sep. 2, 2011.
PCT/US2013/072439 International Search Report dated Feb. 19, 2014.
PCT/US2005/034561 International Preliminary Report on Patentability dated Mar. 27, 2007.
PCT/US2005/034561 International Search Report dated Sep. 27, 2006.
PCT/US2005/027943 International Preliminary Report on Patentability dated Apr. 11, 2007.
PCT/US2005/027943 International Search Report and Written Opinion dated Mar. 21, 2007.
PCT/US2005/04481 International Search Report dated Sep. 12, 2005.
PCT/US2016/063066 ISR and WO mailed Jan. 30, 2017.
PCT/US2018/044774 ISR and WO mailed Oct. 23, 2018.
Batalov et al. "Differentiation of Cardiomyocytes from Human Pluripotent Stem Cells Using Monolayer Culture." Biomarkers Insights, 2015, 10(s1):71-76.
Brustaert et al. "Cardiac Endothelial-Myocardial Signaling: Its Role in Cardiac Growth, Catractile Performance, and Rhythmicity." Physiological Reviews, 2003, 83:59-115.
Jacot et al. "Substrate Stiffness Affects the Functional Maturatioon of Neonatal Rat Ventricular Myocytes." Biophysics Journal, Oct. 2008, 95:3479-3487.
Lundy et al. "Structural and Functional Maturation of Cardiomyocytes Derived from Human Pluripotent Stem Cells." Stem Cells and Development, 2013, 22(14):1991-2002.
McDevitt et al. "In Vitro Generation of Differential Cardiac Myofibers on Micropatterned Laminin Surfaces." Journal of Biomedical Materials Research, 2002, 60:472-479.
Moran et al. "Temporal Trends in Ischemic Heart Disease Mortality in 21 World Regions, 1980 to 2010 The Global Burden of Disease 2010 Study" Circulation, Apr. 8, 2014, 129(14):1483-1492.
Sathaye et al. "Electrical Pacing Counteracts Intrinsic Shortening of Action Potential Duration of Neonatal Rat Ventricular Cells in Culture." Journal of Molecular and Cellular Cardiology, 2006, 41:633-641.
Takahashi et al. "Introduction of Pluripotent Stem Cells from Mouse Embryonic and Adult Fibroblast Cultures by Defined Factors." Cell, Aug. 25, 2006, 126:663-676.
Takahashi et al. "Introduction of Pluripotent Stem Cells from Adult Human Fibroblasts by Defined Factors." Cell, Nov. 30, 2007, 131:861-872.
Werley et al. "Geometry-dependent functional changes in iPSC-derived cardiomyocytes probed by functional imaging and RNA Sequencing." PLOS One, Mar. 23, 2017, 12(3):e0172671.
Yang et al., "Tri-iodo-L-Thyronine Promotes the Maturation of Human Cardiomyocytes-Derived from Induced Pluripotent Stem Cells " Journal of Molecular Cell Cardiology, Jul. 2014, 72:296-304.
Zimmermann et al. "Tissue Engineering of a Differentiated Cardiac Muscle Construct." Circulation Research, Feb. 8, 2002, 90:223-230.
Maher et al. "Targeting Cytotoxic T Lymphocytes for Cancer Immunotherapy." British Journal of Cancer, 2004, 91:817-821.
EP16867327.5 Supplementary Partial European Search Report dated Jun. 6, 2019.
Carrega et al. "Susceptibility of Human Melanoma Cells to Autologous Natural Killer (NK) Cell Killing: HLA-Related Effector Mechanisms and Role of Unlicensed NK Cells " PLoS One, Dec. 4, 2009, 4(12):e8132.
Peper et al. "An Impedance-Based Cytotoxicity Assay for Real-Time and Label-Free Assessment of T-Cell-Mediated Killing of Adherent Cells," Journal of Immunological Methods, Jan. 29, 2014, 405:192-198.
Oberg et al. "Monitoring Circulating gamma-delta-T Cells in Cancer Patients to Optimize gamma-delta-T Cell-Based Immunnotherapy." Frontiers in Immunology, Dec. 17, 2014, 5(643):1-7.
Erskine et al. "Determining Optimal Cytotoxic Activity of Human Her2neu Specific CD8 T Cells by Comparing the CR51 Release Assay to the xCELLigence System," Journal of Visualized Experiments, Aug. 8, 2012, 66(e3683):1-6.
Alici et al. "Autologous Antitumor Activity by NK Cells Expanded from Myeloma Patients Using GMP-Compliant Components," Blood, Mar. 15, 2008, 111(6):3155-3162.
"Label-Free Assay for NK Cell-Mediated Cytolysis," Jan. 1, 2013, pp. 1-8, retrieved from the internet May 23, 2019, URL discloses a method of assessing the effect of e.g. NK cell-mediated cytolysis on target cells using a cell substrate impedance monitoring devices indentical to the one used in the application as filed.
"xCELLigence System Application Table of Contents," Jan. 1, 2014, retrieved from the internet May 23, 2014, URL: https://www.ols-bio.de/media/pdf/Application_Book_09082014_OLS_xs.pdf.
Lamarche et al. Using Impedance-Based Approaches for Measuring Cell-Mediated Cytotoxicity and Antibody-Dependent Cell-Mediated Cytotoxicity (ADCC), Journal of ImmunoTherapy of Cancer, Nov. 4, 2015, 3(Suppl 2) P214.
Miyata et al. "New Wound-Healing Model Using Cultured Corneal Endothelial Cells." Japan Journal of Opthalmology, 1990, 34:257-266.
Mohr et al. "Performance of a Thin Film Microelectrode Array for Monitoring Electrogenic Cells in Vitro." Sensors and Actuators, B34:265-269 (1996).
Neher, Erwin, "Molecular Biology Meets Microelectronics" Nature Biotechnology, 2001; 19:114.
Nerurkar et al. "The Use of Surfactants to Enhance the Permeability of Peptides Through Caco-2 Cells by Inhibition of an Apically Polarized Efflux System." Pharmaceutical Research, 1996,13(4):528-534.
Nicolazzi et al. "Cationic Lipids for Transfection." Current Medicinal Chemistry, 2003, 10:1263-1277.
Oka et al. "A New Planar Multielectrode Array for Extracellular Recording: Application to Hippocampal Acute Slice." Journal of Neuroscience Methods, 1999, 93:61-67, Elsevier Science, B.V.
Ong et al. "Remote Query Resonant-Circuit Sensors for Monitoring of Bacterial Growth: Application to Food Quality Control." Sensors 2002; 2:219-232.

(56) References Cited

OTHER PUBLICATIONS

Pancrazio et al. "Portable Cell-Based Biosensor System for Toxin Detection." Sensors and Actuators 1998; 53:179-185.
Patolsky et al. "Detection of Single-Base DNA Mutations by Enzyme-Amplified Electronic Transduction." Nature Biotechnology, 2001, 19:253-257.
Pethig et al. "Positive and Negative Dielectrophoretic Collection of Colloidal Particles Using Interdigitated Castellated Microelectrodes." Applied Physics, 1992, 24:881-888.
Qiu et al. "Real-Time Monitoring Primary Cardiomyocyte Adhesion Based on Electrochemical Impedance Spectroscopy and Electrical Cell-Substrate Impedance Sensing" Analytical Chemistry, 2008, 80:990-996.
Rabow et al. "Mining the National Cancer Institute's Tumor-Screening Database: Identification of Compounds with Similar Cellular Activities." Journal of Medicinal Chemistry, 2002, 45:818-840.
Richards et al. "A Modified Microchamber Method for Chemotaxis and Chemokinesis." Immunological Communications, 1984, 13 (1):49-62.
Rishpon et al. "An Amperometric Enzyme-channeling Immunosensor." Biosensors & Bioelectronics, 1997, 12 (3):195-204.
Simpson et al. "Whole-Cell Biocomputing." Trends in Biotechnology, 2001, 19(9):317-323.
Slaughter et al. "Artificial Neural Network for Temporal Impedance Recognition of Neurotoxins." 2006 International Joint Conference on Neural Networks 2006; Jul. 16-21: 2001-2008.
Sohn et al. "Capacitance Cytometry: Measuring Biological Cells One by One." Proceedings of the National Academy of Sciences, 2000, 97(20):10687-10690.
Steinem et al. "Impedance and Shear Wave Resonance Analysis of Ligand-Receptor Interactions at Functionalized Surfaces and of Cell Monolayers." Biosensors & Bioelectronics, 1997, 12(8):787-808.
Stenger et al. "Detection of Physiologically Active Compounds Using Cell-Based Biosensors." Trends in Biotechnology, 2001; 19(8):304-309.
Svetlicic et al. "Charge Displacement by Adhesion and Spreading of a Cell." Bioelectrochemistry, 2000, 53:79-86.
Tiruppathi et al. "Electrical Method for Detection of Endothelial Cell Shape Change in Time: Assessment of Endothelial Barrier Function." Proceedings of the National Academy of Sciences, USA, 1992, 89:7919-7923.
Wang et al. "Selective Dielectrophoretic Confinement of Bioparticles in Potential Energy Wells." Applied Physics, 1993, 26:1278-1285.
Wang et al. "Cell Separation by Dielectrophoretic Field-Flow-Fractionation." Analyitcal Chemistry., 2000, 72:832-839.
Wang et al. "Dielectrophoretic Manipulation of Cells with Spiral Electrodes." Biophysical Journal, 1997, 72:1887-1899.
Wang et al. "Separation of Polystyrene Microbeads Using Dielectrophoretic/Gravitational Field-Flow-Fractionation." Biophysical Journal, 1998, 74:2689-2701.
Wang et al. "Electronic Manipulation of Cells on Microchip-Based Devices." In Biochip Technology (eds), 2001, pp. 135-159, Harwood Academic Publishers, PA, USA.
Wang et al. "A Theoretical Method of Electrical Field Analysis for Dielectrophoretic Electrode Arrays Using Green's Theorem." Journal of Phyics D: Applied Physics, 1996; 29:1649-1660.
Warburg Ueber die Polarisationscapacitat des Platins. Annals of Physics, 6:125-135 (1901).
Wegener et al. "Electric Cell-Substrate Impedance Sensing (ECIS) as Noninvasive Means to Monitor the Kinetics of Cell Spreading to Artificial Surfaces." Experimental Cell Research 2000; 259:158-166.
Wegener et al., Use of Electrochemical Impedance Measurements to Monitor Beta-Adrenergic Stimulation of Bovine Aortic Endothelial Cells. European Journal of Physiology, 437:925-934 (1999).
Wolf et al. "Monitoring of Cellular Signalling and Metabolism with Modular Sensor-Technique: The PhysioControl-Microsystem (PCM)." Biosensors and Bioelectronics 1998; 13:501-509.
Xiao et al. "Assessment of Cytotoxicity Using Electric Cell-Substrate Impedance Sensing: Concentration and Time Response Function Approach." Analytical Chemistry, 2002, 74:5748-5753.
Xiao et al. "An In-Depth Analysis of Electric Cell-Substrale Impedance Sensing to Study the Attachment and Spreading of Mammalian Cells." Analytical Chemistry, 2002; 74(6):1333-1339.
Xiao et al. "On-Line Monitoring of Cell Growth and Cytotoxicity Using Electric Cell-Substrate Impedance Sensing (ECIS)." Biotechnology Progress, 2003; 19:1000-1005.
Xing et al. "Dynamic Monitoring of Cytotoxicity on Microelectronic Sensors" Chemical Research in Toxicology., 2005, 18 (2):154-161.
Yamauchi et al. "Spatially and Temporally Controlled Gene Transfer by Electroporation into Adherent Cells on Plasmid DNA-Loaded Electrodes." Nucleic Acids Research, 2004, 32(22):1-8.
Yang et al. "Celli Separation on Microfabricated Electrodes Using Dielectrophoretic/Gravitational field-flow Fractionation." Analytical Chemistry, 1999, 71:911-918.
Yang et al. "A Novel Microtluidic Impedance Assay for Monitoring Endothelin-lnduced Cardiomyocyte Hypertrophy." Biosensors and Bioelectronics, 2007, 22:1688-1693.
Yu et al. "Real-Time Monitoring of Morphological Changes in Living Cells by Electronic Cell Sensor Arrays: An Approach To Study G Protein-Coupled Receptors." Analytical Chemistry, 2006, 78:35-43.
"Automated Cell Monitoring Instrument." Applied BioPhysics, 2002, [retrieved from the internet] http://www.biophysics.com/pages/front.html, 1 page.
"Cell Migration Studies with TECAN Systems." TECAN., Sep. 1999, [retrieved from the internet] http://www.tecan.com/migration_introl.pdf, 10 pgs.
"Detect Cell Migration and Invasion in a Homogeneous Fluorescent Assay System." BD Biosciences, http://www. bdbiosciences.com/discovery_labware/Products/inserts/BD_Falcon_HTS_fluoroblok_inserts/individual_fluoroblok_inserts/index.html, 2004.
HP 4284A Precision LCR Meter Operation Manual, Aug. 1998, Hewlett Packard, 6th Edition, p. 1-460.
"Molecular Viewer" New Products page. Science 298:2409 (2002).
"Neuro Probe AA96, AB96, AC96 Chemotaxis Chambers." Neuro Probe, [retrieved from the internet] http://www.neuroprobe.com/protocol/pt_96a.html, 5 pgs.
CA2556219 Office Action dated Aug. 9, 2010.
CA2575573 Office Action dated Apr. 4, 2012.
EP05722991 Extended European Search Report dated Apr. 3, 2009.
EP11193882 Extended European Search Report dated Apr. 5, 2012.
EP13171137 Extended European Search Report dated Aug. 16, 2013.

\* cited by examiner

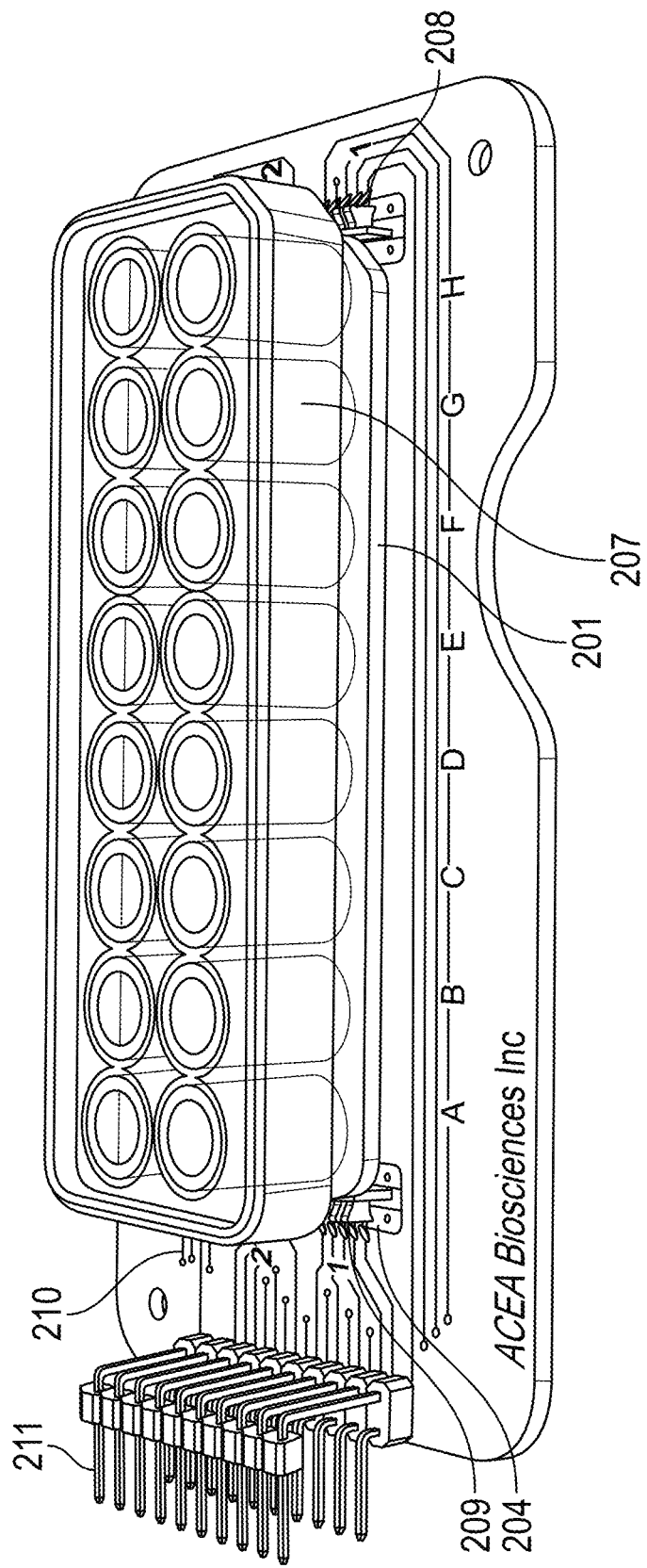

Fig. 6B

REAL TIME ELECTRONIC CELL SENSING SYSTEMS AND APPLICATIONS FOR CELL-BASED ASSAYS

CROSS REFERENCE TO RELATED APPLICATIONS

This is a divisional of U.S. patent application Ser. No. 15/487,349, filed Apr. 13, 2017, which is a continuation of U.S. patent application Ser. No. 13/244,004, filed Sep. 23, 2011, now U.S. Pat. No. 9,625,472, which is a divisional of U.S. patent application Ser. No. 11/725,040, filed Mar. 15, 2007, now U.S. Pat. No. 8,026,080, which is a divisional of U.S. patent application Ser. No. 10/987,732, filed Nov. 12, 2004, now U.S. Pat. No. 7,192,752, which is a continuation-in-part of U.S. patent application Ser. No. 10/705,447, filed Nov. 10, 2003, now U.S. Pat. No. 7,470,533, which claims priority to U.S. provisional patent application No. 60/435,400, filed Dec. 20, 2002, and claims priority to U.S. provisional application No. 60/469,572, filed May 9, 2003. All of the applications referred to in this paragraph are incorporated by reference herein.

U.S. patent application Ser. No. 10/987,732 is also a continuation-in-part of U.S. patent application Ser. No. 10/705,615, filed on Nov. 10, 2003, now U.S. Pat. No. 7,459,303, which claims priority to U.S. provisional patent application No. 60/435,400, filed Dec. 20, 2002 and claims priority to U.S. provisional application No. 60/469,572, filed May 9, 2003. All of the applications referred to in this paragraph are incorporated by reference herein.

U.S. patent application Ser. No. 10/987,732 also claims priority to U.S. provisional patent application No. 60/519,567 filed Nov. 12, 2003, U.S. provisional patent application No. 60/542,927 filed Feb. 9, 2004, and U.S. provisional patent application No. 60/548,713, filed Feb. 27, 2004. All of the applications referred to in this paragraph are incorporated by reference herein.

TECHNICAL FIELD

This invention relates to the field of cell-based assays. In particular, the invention provides impedance-based devices, apparatuses and systems for analyzing cells and for conducting cell-based assays.

BACKGROUND OF THE INVENTION

A. Electronic Analysis of Cells

Bioelectronics is a progressing interdisciplinary research field that involves the integration of biomaterials with electronic devices. Bioelectronic methods have been used for analyzing cells and assaying biological molecules and cells. In one type of application, cells are cultured on microelectrodes and cell-electrode impedance is measured and determined to monitor cellular changes.

In PCT Application No. PCT/US03/22557, entitled "IMPEDANCE BASED DEVICES AND METHODS FOR USE IN ASSAYS", filed on Jul. 18, 2003, a device for detecting cells and/or molecules on an electrode surface is disclosed. The device detects cells and/or molecules through measurement of impedance changes resulting from the attachment or binding of cells and/or molecules to the electrode surfaces. A number of embodiments of the device is disclosed, together with the apparatuses, system for using such devices to perform certain cell based assays.

B. Allergic Diseases and IgE-Mediated Cell Activation

Allergic diseases, also commonly known as immediate hypersensitivity disorder are the most common dysfunction of the immune system afflicting 20% of all individuals in the United States. The immediate hypersensitivity response can range anywhere from a simple rash or itchy and watery eyes to the most extreme case of anaphylaxis, where the airways are restricted to the point of asphyxiation and death. Due to the severity of the hypersensitivity responses, the lack of adequate treatment and the high percentage of the population suffering from various forms of this condition, the pharmaceutical industry has taken a keen interest in developing novel drugs to effectively treat and combat the symptoms of this disabling and potentially life threatening disorder.

The primary cells of the immune system that are involved in the allergic response are mast cells, basophils and eisonophils. Basophils and eisonophils differentiate in the bone marrow, circulate in the blood and are recruited to the sites of the inflamed tissue in the late-phase of the reactions. In contrast, mast cells are normally distributed throughout the connective tissue and are the involved in the immediate phase of immunoglobulin E (IgE)-mediated allergic reactions (Sharma et al. Clin Rev Allergy Immunol. 2002 April; 22(2):119-48). The initial encounter of an individual with an allergen leads to the production of IgE, which binds to the high affinity IgE receptor (Fc(epsilon)RI) on the surface of mast cells causing sensitization of the mast cells. Subsequent encounter with the allergen leads to cross-linking of the Fc(epsilon)RI-IgE complex on the surface of mast cells and stimulation of the mast cells to release mediators of immediate hypersensitivity. The cross-linking of receptor-bound IgE on the mast cell surface triggers a sequence of intracellular events, collectively referred to as mast cell activation that culminate in the extracellular release of potent inflammatory mediators, many of which are stored in the secretory granules, including histamine. Mast cell activation can be divided into an interdependent early and late phase. The early phase of mast cell activation include phosphorylation and activation of protein tyrosine kinases and their substrates, generation of the second messengers inositol-tris phosphate and diacylglycerol, elevation of intracellular calcium levels and fusion of secretory granules with the membrane (Stassen et al. Crit Rev Immunol. 2002; 22(2):115-40). The late phase of mast cell activation includes dramatic morphological changes due to remodeling of the actin cytoskeleton, gene expression leading to the synthesis and secretion of potent inflammatory cytokines and synthesis of lipid mediators that have variety of effects on blood vessels, bronchial smooth muscle and leukocytes.

Based on the various steps involved in the initiation and execution of the immediate hypersensitivity response, there are multiple potential targets for pharmaceutical intervention. The bulk of the current therapies for immediate hypersensitivity disorders such as asthma seek to alleviate the symptoms of the condition rather than directly target the underlying cause. However, current promising efforts are underway to neutralize the IgE antibody by administration of humanized monoclonal anti-IgE antibody and to achieve long term alleviation of clinical symptoms (D'Amato et al. Monaldi Arch Chest Dis. 2003 January-March; 59(1):25-9). Also, the elucidation of the intrinsic signaling pathways underlying IgE-mediated mast cell activation together with the advent of combinatorial chemistry provide ample opportunity to employ small molecular inhibitors to target key proteins and enzymes involved in mast cell activation. These compounds could potentially provide novel immunomodulators for the treatment of immediate hypersensitivity disorder. Small molecular inhibitors of several kinases, including PKC and the tyrosine kinase Syk have provided encouraging preclinical results in rodent studies in blocking some immediate hypersensitivity responses (Seow et al. Eur J Pharmacol. 2002 May 17; 443(1-3):189-96).

An increasing number of companies are utilizing large chemical libraries to screen for potential inhibitors of signaling pathways that maybe involved in various disease states. Hence, there is an urgent need for high-throughput molecular and cellular assays to screen for potential modulators of these signaling pathways. With regards to IgE-mediated signaling, the current assays measure mediators that are released into the media after degranulation. This is accomplished by either measuring the enzymatic activity of these mediators (Rac and phosphatidylinositol 3-kinase regulate the protein kinase B in Fc epsilon RI signaling in RBL 2H3 mast cells. J Immunol. 2001 Feb. 1; 166(3):1627-34), using radioactive precursors (Guillermot et al. J Cell Sci. 1997 September; 110 (Pt 18):2215-25), or by ELISA, quantifying the amount of mediators that are released (Berger et al. Allergy. 2002 July; 57(7):592-9). These assays are single point assays or endpoint assays which measure the cumulative release of these mediators and also involve utilization of reagents and manipulation of the cells, such as fixation or lysis. The fact that these are single point assays, which utilize expensive reagents such as antibodies and cellular manipulation, does not warrant adaptability for high-throughput analysis that is required to screen large chemical libraries.

C. Anticancer Drug Screening and Discovery

In anticancer drug development, the study of the time dependence of cytotoxic and cell proliferation inhibitory effect of a drug is an important element for gaining information to use in the development of clinical dosing strategies. In particular, time dependent IC50's are derived and different time dependent patterns for IC50's are observed (e.g., see Hassan S B, Jonsson E, Larsson R and Karlsson M O in *J. Pharmacology and Experimental Therapeutics*, 2001, Vol. 299, No. 3, pp 1140-1147; Levasseur L M, Slocum H K, Rustum Y M and Greco W R, in *Cancer Research*, 1998, vol. 58, pp 5749-5761.). Typically, these studies used end-point single-measurement assays. Each time point for a dose concentration of drug or compound applied to the cultured cells required a separate experiment. This limits the time resolution and the number of time points of such time-dependent cytotoxicity studies. Thus, new technologies or methods that can provide higher time resolution and permit measurements on many time points are needed.

The present invention further expands the inventions disclosed in PCT Application No. PCT/US03/22557, entitled "IMPEDANCE BASED DEVICES AND METHODS FOR USE IN ASSAYS", filed on Jul. 18, 2003 and disclosed in U.S. patent application Ser. No. 10/705,447, entitled "IMPEDANCE BASED DEVICES AND METHODS FOR USE IN ASSAYS", filed on Nov. 10, 2003. The invention provides a real time cell electronic sensing system for conducting cell-based assays based on measurement of cell-substrate impedance and provides the method for using such a system to perform cell-based assays. Furthermore, the present invention is aimed at addressing the limitations in current methods and technologies for assaying IgE-mediated signaling and cell activation.

BRIEF SUMMARY OF THE INVENTION

In one aspect, the present invention is directed to a device for monitoring cell-substrate impedance, which device comprises: a) a nonconducting substrate; b) two or more electrode arrays fabricated on the substrate, where each of the two or more electrode arrays comprises two electrode structures; and c) at least two connection pads, each of which is located on an edge of the substrate. For each of the two or more electrode arrays of the device, the first of the two electrode structures is connected to one of the two or more connection pads, and the second of the two electrode structures is connected to another of the two or more connection pads. Each of the two electrode structures of the two or more electrode arrays comprises multiple electrode elements, and each electrode array of the device has an approximately uniform electrode resistance distribution across the entire array. The substrate of the device has a surface suitable for cell attachment or growth; where cell attachment or growth on said substrate can result in a detectable change in impedance between or among the electrode structures within each electrode array. In preferred embodiments, each electrode array on the substrate of a device of the present invention is associated with a fluid-impermeable container.

In another aspect, the present invention is directed to a cell-substrate impedance measurement system comprising: a) at least one multiple-well device monitoring cell-substrate impedance, in which at least two of the multiple wells each comprise an electrode array at the bottom of the well; b) an impedance analyzer; c) a device station capable of engaging the one or more multiple-well devices and capable of selecting and electrically connecting electrode arrays within any of the multiple wells in to the impedance analyzer; and d) a software program to control the device station and perform data acquisition and data analysis on impedance values measured by the impedance analyzer. In preferred embodiments of this aspect of the present invention, each electrode array of the multiple-well device is individually addressed.

In yet another aspect, the present invention provides a method for monitoring cell-substrate impedance using a device of the present invention. The method includes: providing a multiple array device of the present invention; connecting said multiple array device to an impedance analyzer; depositing cells on at least one of the two or more arrays of the device; and monitoring cell-substrate impedance on one or more arrays of the device.

In yet another aspect, the present invention provides methods for calculating a Cell Index for quantifying and comparing cell-substrate impedance.

In yet another aspect, the present invention provides methods for calculating resistance of electrical traces connecting an array of a cell-substrate monitoring device with a connection pad. Such calculations of electrical trace resistance can be used for calculating Cell Index.

In yet another aspect, the present invention provides a method for monitoring cell-substrate impedance using a cell-substrate impedance measurement system of the present invention. The method includes: providing a cell-substrate impedance measurement system of the present invention, adding cells to at least one well of the multiple-well device that comprises an electrode array, and monitoring cell-substrate impedance from one or more of the wells that comprise cells. Impedance can be monitored at regular or irregular time intervals. In preferred embodiments, cell-substrate impedance is monitored in at least two wells of a multiple-well device.

In yet another aspect, the present invention provides a method for performing real-time cell-based assays investigating the effects of one or more compound on cells, comprising: providing an above described cell-substrate impedance measurement system; introducing cells into at least one well of the system that comprises an electrode array; adding one or more compounds to one or more of the wells containing cells; and monitoring cell-substrate impedance over the electrode array of the one or more wells before and after adding the one or more compounds. Preferably, cell-substrate impedance is monitored at regular or irregular time intervals after adding one or more compounds to the one or more of the wells containing cells. The time dependent impedance change can provide information about time dependent cell status before addition of the compound and about time dependent cell status under the interaction of the compound. This information can be used to determine the effect of a compound on the cells.

In yet another aspect, the present invention provides a method for performing real-time cytotoxicity assays of at least one compound, comprising: providing an above described cell-substrate impedance measurement system; introducing cells into one or more wells of the system that comprise an electrode array; adding one or more compounds to the one or more wells containing cells; and monitoring cell-substrate impedance of the one or more wells before and after adding the one or more compounds, wherein the time dependent impedance change provides information about time dependent cytotoxicity of the compound or compounds. Preferably, cell-substrate impedance is monitored at regular or irregular time intervals after adding one or more compounds to the one or more of the wells containing cells. The time dependent impedance change can provide information about any potential cytotoxic effects of the compound.

In one embodiment of the above method, multiple wells with same cell types are used, wherein different concentrations of a compound are added to different wells that comprise cells. The method can provide time-dependent and concentration-dependent cytotoxic responses.

In yet another aspect, the present invention provides a method for analyzing and comparing time-dependent cytotoxic effects of a first compound and a second compound on a cell type, comprising: a) performing a real-time cytotoxicity assay on a cell type with the first compound using the method described above; b) performing a real-time cytotoxicity assay on said cell type with the second compound using the method described above; and c) comparing the time-dependent cytotoxic responses of the first compound and the second compound.

In one embodiment of this method, time-dependent cytotoxic responses are determined for a first compound at multiple dose concentrations. In another embodiment, time-dependent cytotoxic responses are determined for a second compound at multiple dose concentrations. In yet another embodiment, time-dependent cytotoxic responses are determined for both a first compound and a second compound at multiple dose concentrations.

In yet another aspect, the present invention provides methods for cytotoxicity profiling for a compound on multiple cell types, comprising: a) performing real-time cytotoxicity assays on different cell types with the compound using the method described above, and b) analyzing real-time cytotoxic responses of different cell types to the compound to provide a cytotoxicity profile of the compound.

In yet another embodiment, the above methods are applied to perform cytotoxicity profiling of multiple compounds on multiple cell types.

In yet another aspect, the present invention is directed to method to use electronic impedance technology to assess and quantify the morphological changes that occur in cells as a result of IgE stimulation and IgE receptor cross-linking with an antigen. The method includes: providing a cell-substrate impedance measurement system of the present invention; introducing cells into one or more wells of the system, adding IgE to the one or more wells comprising cells; adding an antigen to the one or more wells comprising cells and IgE; and monitoring cell-substrate impedance from the one or more wells of the system. Impedance can be monitored before and after adding IgE, and is preferably measured before adding IgE, after adding IgE and before adding antigen, and after adding antigen. The cell-substrate impedance can be used as an indicator of a cell's response to IgE stimulation through cell morphological changes.

In yet another aspect, the present invention is directed at a method to screen for inhibitors of signaling pathways that are initiated by engagement of the IgE-Fc(epsilon)RI complex by an antigen by utilizing electronic measurement and sensing of cells. The method includes: providing a cell-substrate impedance measurement system of the present invention, introducing cells into one or more wells of the system, adding at least one test compound to at least one of the one or more wells containing cells; providing at least one control well comprising cells in the absence of test compound; adding IgE to the one or more wells comprising cells and test compound and to the one or more control wells; adding an antigen to the one or more wells comprising cells and test compound and to the one or more control wells; and monitoring cell-substrate impedance from the one or more wells of the system. Impedance can be monitored before and after adding IgE, and is preferably measured before adding IgE, after adding IgE and before adding antigen, and after adding antigen. The cell-substrate impedance can be used as an indicator of a cell's response to IgE stimulation through cell morphological changes. Comparsion of the cell-substrate impedance in one or more wells comprising test compound with one or more control wells provides an assessment of the effect of a test compound on the cells' response to IgE stimulation. In particular, inhibitors of the IgE response can be identified by their property of reducing the cell-impedance response of cells treated with test compound when compared with the responses of control cells.

In one embodiment of this aspect, the present invention is directed to method to use electronic impedance technology to screen for potential inhibitors of IgE binding to the high affinity Fc(epsilon)RI receptor on the surfaces of mast cells or basophils.

In another embodiment of this aspect, the present invention is directed to method of using electronic impedance technology for screening of small molecular inhibitors of key enzymes and proteins involved in the signaling pathway that ensues from engagement of the high-affinity Fc(epsilon)RI receptor of cells in the presence or absence of IgE cross-linking by the antigen.

In yet another aspect, the present invention is directed to method to use electronic impedance technology for target validation purposes of key enzymes and proteins involved in the signaling pathway leading from engagement of the high-affinity FcεRI receptor of cells in the presence or absence of IgE cross-linking by the antigen. The method includes: providing a cell-substrate impedance measurement system of the present invention; introducing genetically modified cells into one or more wells of the system; providing at least one control well comprising cells that are not genetically modified; adding IgE to the wells comprising genetically modified cells and to the one or more control wells, adding an antigen to the wells comprising genetically modified cells and to the one or more control wells; adding an antigen to the wells comprising genetically modified cells and to the one or more control wells; monitoring cell-substrate impedance form the wells comprising genetically modified cells and to the one or more control wells; and analyzing the impedance data to determine the effect of the genetic alteration on the response of cells to IgE stimulation.

In yet another aspect, the present invention is directed to method to use electronic impedance technology for comparing IgE-mediated responses of cells of different genetic backgrounds. The method can be used for screening and validating genetic markers such as gene expression profiles, gene splicing variants, protein expression profiles, key single nucleotide polymorphisms (SNPs) or mutations and other genetic variants that determine or influence the IgE stimulation, IgE receptor interactions, antigen-mediated IgE receptor cross-linking, intracellular signal transduction pathways, and degranulation.

In yet another aspect, the present invention is directed to method to use electronic impedance technology for screening, discovering, and validating chemical structures of antigens (allergens) and half antigens, which lead to IgE cross-linking specifically or nonspecifically.

BRIEF DESCRIPTION OF THE DRAWINGS

FIG. 1A depicts the substrate having 16 electrode arrays (or 16 electrode structure units) that are arranged in a 2-row by 8-column configuration on a substrate. FIG. 1B depicts a single electrode array of a device. FIG. 1C shows a schematic drawing of an electrode array, illustrating the requirement of approximately uniform distribution of electrode resistance across the array.

FIG. 2 shows an image of a 16× device of the present invention.

FIGS. 6A-E show different pages from real-time cell electronic sensing software. In FIG. 6A, an experimental note page allows the recording of key information about the experiment by the experimenter, such as the goals and procedures of the experiment. In FIG. 6B, an experimental layout page allows the recording of cells, cell number, compound and compound concentration added into each well. In FIG. 6C, a test time setting page allows for the recording and control of time intervals used for performing cell-substrate impedance measurement and multiple experimental steps each having different time interval values and different length times can be setup. In FIG. 6D, a cell index page is a result page where the software automatically update the measured and derived cell index values for all wells that are under test after the completion of each measurement at predetermined time interval as setup by the Test time setting page. In FIG. 6E, an experimental data plot page allows for flexible plotting and organization of experimental data.

Approximately 14 hours after seeding the cells were incubated with 100 ng/mL anti-DNP IgE followed by application of 100 ng/mL DNP-BSA 24 hours later. Impedance measurements (indicated as Cell Index) were performed at 5 minute intervals post DNP-BSA application.

Figure 15A:
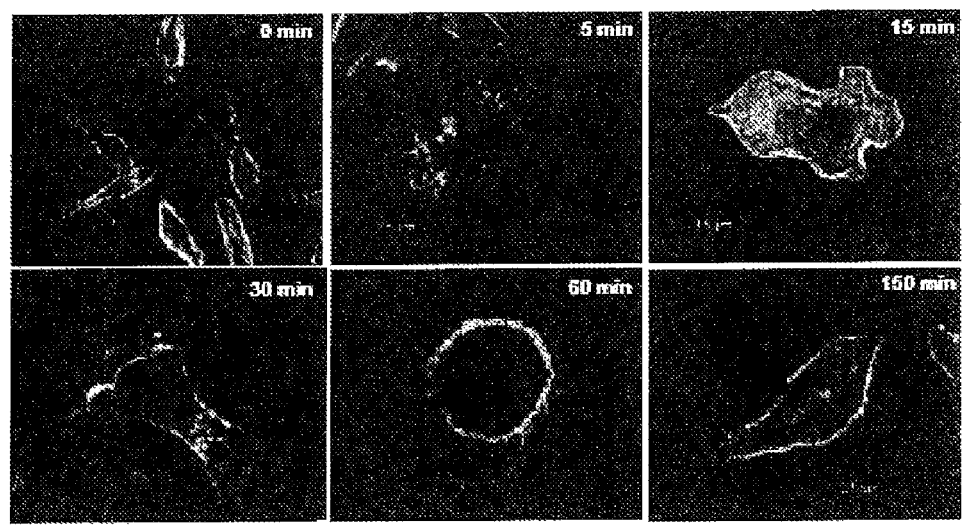
Figure 15B:
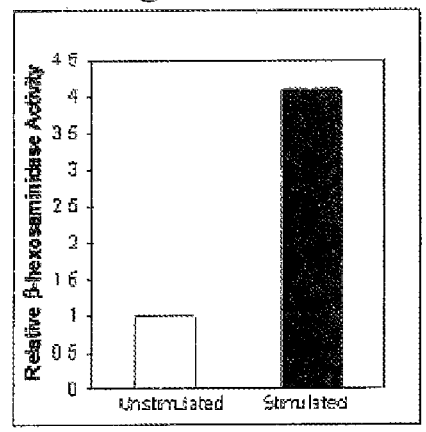

FIGS. 15A-B show correlation between cell-electrode impedance response of RBL-2H3 mast cells and cell morphological dynamics and mediator release. (A) RBL-2H3 mast cells were sensitized with 100 ng/mL IgE or treated with a control IgG antibody and subsequently activated with DNP-BSA. The cells were fixed with paraformaldehyde at the indicated time points, permeablized and stained with rhodamine-phalloidin. The cells were visualized and photographed with a Nikon E-400 immunoflourescence microscope equipped with a CCD camera. (B) RBL-2H3 cells were sensitized with IgE, activated by the addition of DNP-BSA.

Figure 16A:
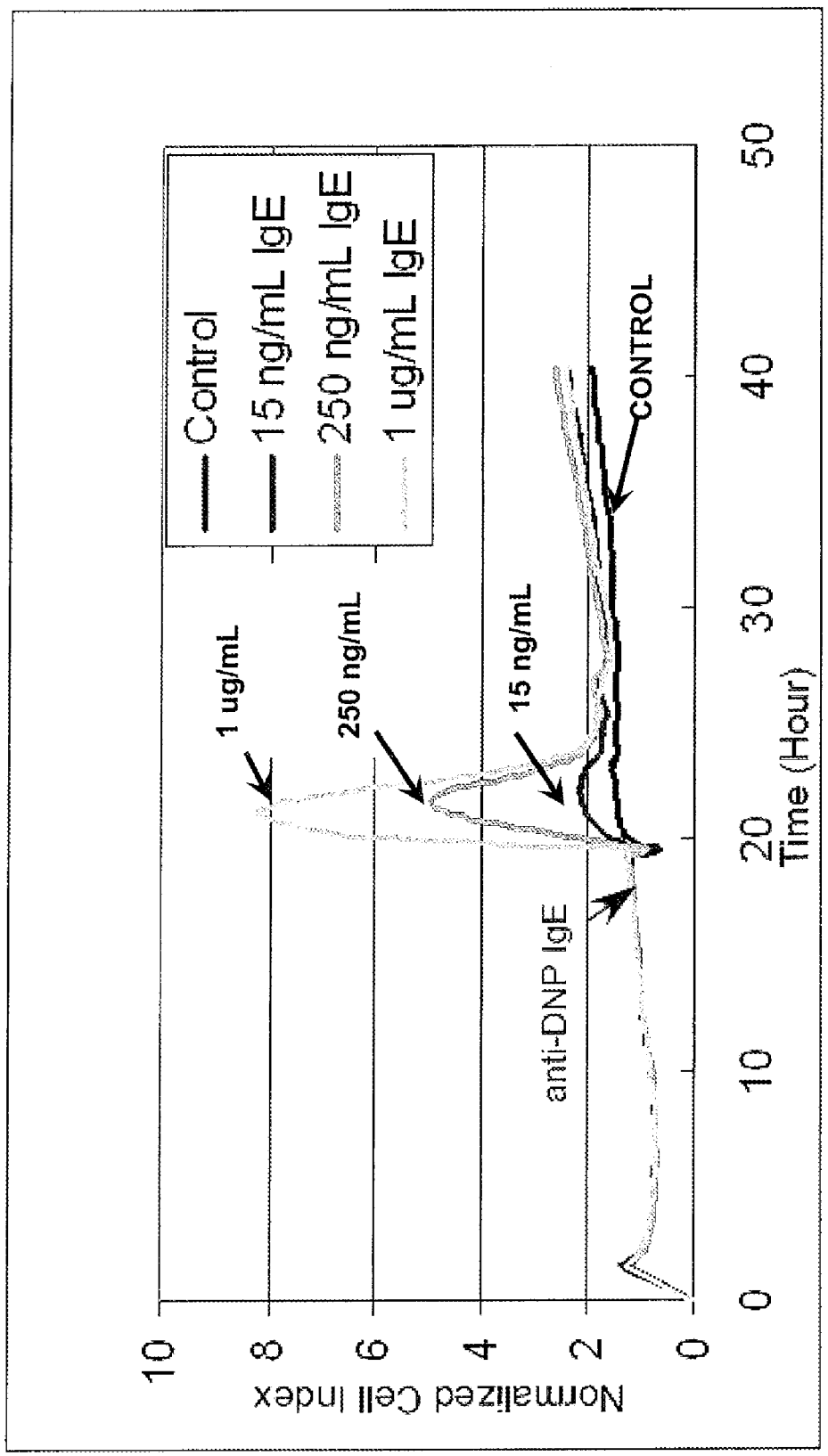
Figure 16B:
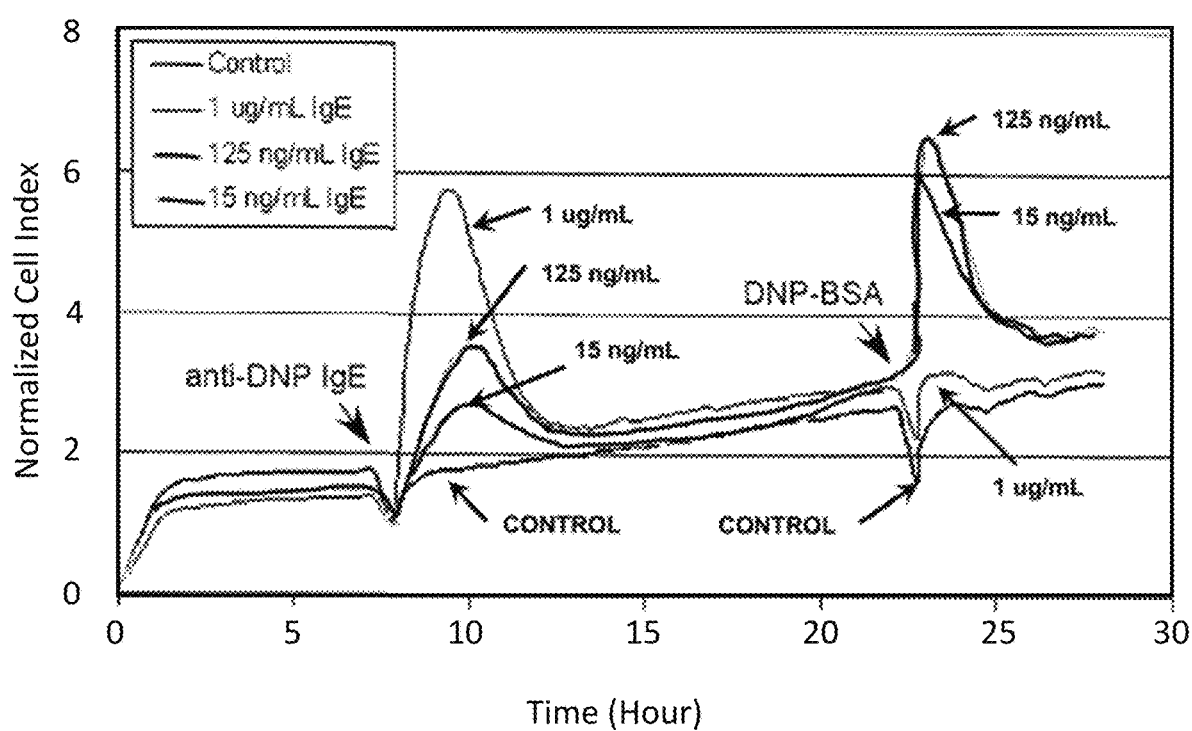

FIGS. 16A-B show IgE alone-mediated increase in mast cell-electrode impedance response and its effect on antigen-mediated activation step. (A) RBL-2H3 cells seeded on microelectronic sensor arrays were left untreated or treated with indicated concentration of anti-DNP IgE. The impedance value indicated as Cell Index was continuously monitored and recorded using a cell-substrate impedance monitoring system. (B) RBL-2H3 cells that had been sensitized with 15 ng/mL or 1 microgram/mL anti-DNP-IgE were activated by the application of 100 ng/mL DNP-BSA. The impedance value indicated as Cell Index was continuously monitored using the system.

Figure 17:
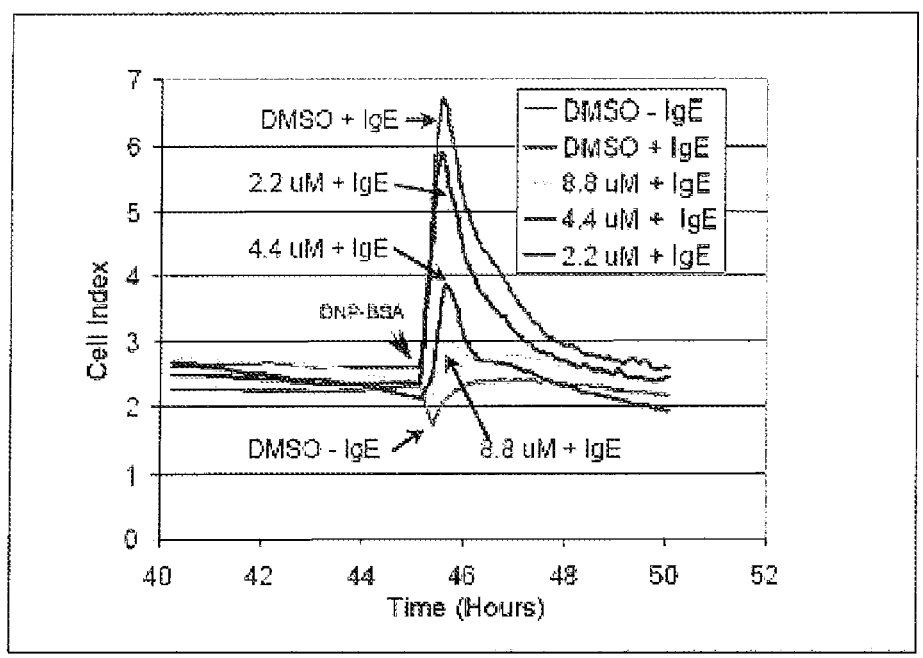

FIG. 17 shows monitoring of inhibitory effects of Protein kinase C inhibitor, Bisindolylmaleimide on IgE-mediated RBL-2H3 mast cell activation by cell-electrode impedance measurement. RBL-2H3 mast cells were sensitized with 100 ng/mL anti-DNP-IgE and then incubated with the indicated concentrations of the Bisindolylmaleimide 1 hour prior to addition of 100 ng/mL DNP-BSA. The impedance value indicated as Cell Index was monitored using a cell-substrate impedance monitoring system of the present invention.

Figure 18:
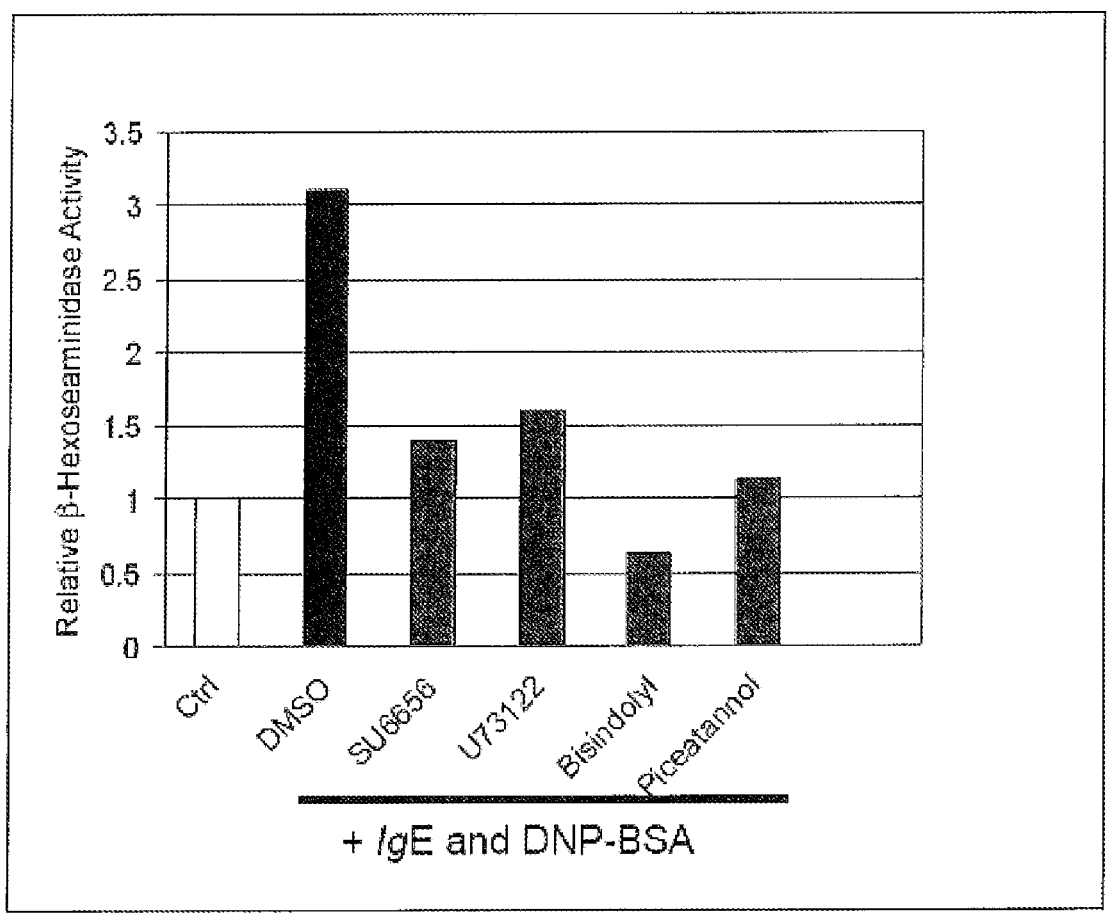

FIG. 18 shows the beta-hexosaminidase activity of IgE-mediated RBL-2H3 mast cells measured in the presence of pharmacological inhibitors. RBL-2H3 mast cells were sensitized, incubated with DMSO, 16.6 micromolar SU 6656, 5 micromolar U73122, 16.6 micromolar Bisindolylmaleimide, 16.6 micromolar Piceatannol and 16.6 micromolar PD 98059 for 1 hour. The cells were activated by the addition of 100 ng/mL DNP-BSA.

DETAILED DESCRIPTION OF THE INVENTION

A. Definitions

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "membrane" is a sheet of material.

As used herein, "biocompatible membrane" means a membrane that does not have deleterious effects on cells, including the viability, attachment, spreading, motility, growth, or cell division.

When a suspension of viable, unimpaired, epithelial or endothelial cells is added to a vessel, a surface of the vessel "is suitable for cell attachment" when a significant percentage of the cells are adhering to the surface of the vessel within twelve hours. Preferably, at least 50% of the cells are adhering to the surface of the vessel within twelve hours. More preferably, a surface that is suitable for cell attachment has surface properties so that at least 70% of the cells are adhering to the surface within twelve hours of plating (i.e., adding cells to the vessel). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating. To have desired surface properties for cell attachment, the surface may need to chemically-treated (e.g. treatment with an acid and/or with a base), and/or physically treated (e.g. treatment with plasma), and/or biochemically treated (e.g. coated with one or more molecules or biomolecules that promotes cell attachment). In the present invention, a biocompatible surface (such as a membrane) preferably is suitable for the attachment of cells of the type that are to be used in an assay that uses the biocompatible surface (e.g., membrane), and most preferably, allows the attachment of at least 90% of the cells that contact the biocompatible surface during the assay.

A "biomolecular coating" is a coating on a surface that comprises a molecule that is a naturally occurring biomolecule or biochemical, or a biochemical derived from or based on one or more naturally occurring biomolecules or biochemicals. For example, a biomolecular coating can comprise an extracellular matrix component (e.g., fibronectin, collagens), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals.

An "extracellular matrix component" is a molecule that occurs in the extracellular matrix of an animal. It can be a component of an extracellular matrix from any species and from any tissue type. Nonlimiting examples of extracellular matrix components include laminins, collagens fibronectins, other glycoproteins, peptides, glycosaminoglycans, proteoglycans, etc. Extracellular matrix components can also include growth factors.

An "electrode" is a structure having a high electrical conductivity, that is, an electrical conductivity much higher than the electrical conductivity of the surrounding materials.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike projection of an interdigitated electrode structure.

As used herein, an "electrode array" or "electrode structure unit" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Non-limiting examples of electrode structure units are interdigitated electrode structure units and concentric electrode structure units.

An "electrode bus" is a portion of an electrode that connects individual electrode elements or substructures. An electrode bus provides a common conduction path from individual electrode elements or individual electrode substructures to another electrical connection. In the devices of the present invention, an electrode bus can contact each electrode element of an electrode structure and provide an electrical connection path to electrical traces that lead to a connection pad.

"Electrode traces" or "electrically conductive traces" or "electrical traces", are electrically conductive paths that extend from electrodes or electrode elements or electrode structures toward one end or boundary of a device or apparatus for connecting the electrodes or electrode elements or electrode structures to an impedance analyzer. The end or boundary of a device may correspond to the connection pads on the device or apparatus.

A "connection pad" is an area on an apparatus or a device of the present invention which is electrically connected to at least one electrode or all electrode elements within at least one electrode structure on an apparatus or a device and which can be operatively connected to external electrical circuits (e.g., an impedance measurement circuit or a signal source). The electrical connection between a connection pad and an impedance measurement circuit or a signal source can be direct or indirect, through any appropriate electrical conduction means such as leads or wires. Such electrical conduction means may also go through electrode or electrical conduction paths located on other regions of the apparatus or device.

"Interdigitated" means having projections coming one direction that interlace with projections coming from a different direction in the manner of the fingers of folded hands (with the caveat that interdigitated electrode elements preferably do not contact one another).

As used herein, a "high probability of contacting an electrode element" means that, if a cell is randomly positioned within the sensor area of a device or apparatus of the present invention, the probability of a cell (or particle) contacting on an electrode element, calculated from the average diameter of a cell used on or in a device or apparatus of the present invention, the sizes of the electrode elements, and the size of the gaps between electrode elements, is greater than about 50%, more preferably greater than about 60%, yet more preferably greater than about 70%, and even more preferably greater than about 80%, greater than about 90%, or greater than about 95%.

As used herein, "at least two electrodes fabricated on said substrate" means that the at least two electrodes are fabricated or made or produced on the substrate. The at least two electrodes can be on the same side of the substrate or on the different side of the substrate. The substrate may have multiple layers, the at least two electrodes can be either on the same or on the different layers of the substrate.

As used herein, "at least two electrodes fabricated to a same side of said substrate" means that the at least two electrodes are fabricated on the same side of the substrate.

As used herein, "at least two electrodes fabricated to a same plane of said substrate" means that, if the nonconducting substrate has multiple layers, the at least two electrodes are fabricated to the same layer of the substrate.

As used herein, "said . . . electrodes [or electrode structures] have substantially the same surface area" means that the surface areas of the electrodes referred to are not substantially different from each other, so that the impedance change due to cell attachment or growth on any one of the electrodes (or electrode structures) referred to will contribute to the overall detectable change in impedance to a same or similar degree as the impedance change due to cell attachment or growth on any other of the electrodes (or electrode structures) referred to. In other words, where electrodes (or electrode structures) have substantially the same surface area, any one of the electrodes can contribute to overall change in impedance upon cell attachment or growth on the electrode. In most cases, the ratio of surface area between the largest electrode and the smallest electrode that have "substantially the same surface area" is less than 10. Preferably, the ratio of surface area between the largest electrode and the smallest electrode of an electrode array is less than 5, 4, 3, 2, 1.5, 1.2 or 1.1. More preferably, the at least two electrodes of an electrode structure have nearly identical or identical surface area.

As used herein, "said device has a surface suitable for cell attachment or growth" means that the electrode and/or non-electrode area of the apparatus has appropriate physical, chemical or biological properties such that cells of interest can viably attach on the surface and new cells can continue to attach, while the cell culture grows, on the surface of the apparatus. However, it is not necessary that the device, or the surface thereof, contain substances necessary for cell viability or growth. These necessary substances, e.g., nutrients or growth factors, can be supplied in a medium. Preferably, when a suspension of viable, unimpaired, epithelial or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among said electrodes" (or "detectable change in impedance between or among said electrode structures") means that the impedance between or among said electrodes (or electrode structures) would have a significant change that can be detected by an impedance analyzer or impedance measurement circuit when molecule binding reaction occurs on the electrode surfaces. The impedance change refers to the difference in impedance values when molecule binding reaction occurs on the electrode surface of the apparatus and when no molecular reaction occurs on the electrode surface. Alternatively, the impedance change refers to the difference in impedance values when cells are attached to the electrode surface and when cells are not attached to the electrode surface, or when the number, type, activity, adhesiveness, or morphology of cells attached to the electrode-comprising surface of the apparatus changes. In most cases, the change in impedance is larger than 0.1% to be detectable. Preferably, the detectable change in impedance is larger than 1%, 2%, 5%, or 8%. More preferably, the detectable change in impedance is larger than 10%. Impedance between or among electrodes is typically a function of the frequency of the applied electric field for measurement. "Detectable change in impedance between or among said electrodes" does not require the impedance change at all frequencies being detectable. "Detectable change in impedance between or among said electrodes" only requires a detectable change in impedance at any single frequency (or multiple frequencies). In addition, impedance has two components, resistance and reactance (reactance can be divided into two categories, capacitive reactance and inductive reactance). "Detectable change in impedance between or among said electrodes" requires only that either one of resistance and reactance has a detectable change at any single frequency or multiple frequencies. In the present application, impedance is the electrical or electronic impedance. The method for the measurement of such impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. Measurement of such electric impedance is an electronic or electrical process that does not involve the use of any reagents.

As used herein, "said at least two electrodes have substantially different surface area" means that the surface areas of any electrodes are not similar to each other so that the impedance change due to cell attachment or growth on the larger electrode will not contribute to the overall detectable impedance to a same or similar degree as the impedance change due to cell attachment or growth on the smaller electrodes. Preferably, any impedance change due to cell attachment or growth on the larger electrode is significantly smaller than the impedance change due to cell attachment or growth on the smaller electrode. Ordinarily, the ratio of surface area between the largest electrode and the smallest electrode is more than 10. Preferably, the ratio of surface area between the largest electrode and the smallest electrode is more than 20, 30, 40, 50 or 100.

As used herein, "multiple pairs of electrodes or electrode structures spatially arranged according to wells of a multi-well microplate" means that the multiple pairs of electrodes or electrode structures of a device or apparatus are spatially arranged to match the spatial configuration of wells of a multi-well microplate so that, when desirable, the device can be inserted into, joined with, or attached to a multiwell plate (for example, a bottomless multiwell plate) such that multiple wells of the multi-well microplate will comprise electrodes or electrode structures.

As used herein, "arranged in a row-column configuration" means that, in terms of electric connection, the position of an electrode, an electrode array or a switching circuit is identified by both a row position number and a column position number.

As used herein, "each well contains substantially same number . . . of cells" means that the lowest number of cells in a well is at least 50% of the highest number of cells in a well. Preferably, the lowest number of cells in a well is at least 60%, 70%, 80%, 90%, 95% or 99% of the highest number of cells in a well. More preferably, each well contains an identical number of cells.

As used herein, "each well contains . . . same type of cells" means that, for the intended purpose, each well contains same type of cells; it is not necessary that each well contains exactly identical type of cells. For example, if the intended purpose is that each well contains mammalian cells, it is permissible if each well contains same type of mammalian cells, e.g., human cells, or different mammalian cells, e.g., human cells as well as other non-human mammalian cells such as mice, goat or monkey cells, etc.

As used herein, "each well contains . . . serially different concentration of a test compound" means that each well contains a test compound with a serially diluted concentrations, e.g., an one-tenth serially diluted concentrations of 1 M, 0.1 M, 0.01 M, etc.

As used herein, "dose-response curve" means the dependent relationship of response of cells on the dose concentration of a test compound. The response of cells can be measured by many different parameters. For example, a test compound is suspected to have cytotoxicity and cause cell death. Then the response of cells can be measured by percentage of non-viable (or viable) cells after the cells are treated by the test compound.

As used herein, "the electrodes have, along the length of the microchannel, a length that is substantially less than the largest single-dimension of a particle to be analyzed" means that the electrodes have, along the length of the microchannel, a length that is at least less than 90% of the largest single-dimension of a particle to be analyzed. Preferably, the electrodes have, along the length of the microchannel, a length that is at least less than 80%, 70%, 60%, 50%, 40%, 30%, 20%, 10%, 5% of the largest single-dimension of a particle to be analyzed.

As used herein, "the microelectrodes span the entire height of the microchannel" means that the microelectrodes span at least 70% of the entire height of the microchannel. Preferably, microelectrodes span at least 80%, 90%, 95% of the entire height of the microchannel. More preferably, microelectrodes span at least 100% of the entire height of the microchannel.

As used herein, "an aperture having a pore size that equals to or is slightly larger than size of said particle" means that aperture has a pore size that at least equals to the particle size but less than 300% of the particle size. Here both pore size and particle size are measured in terms of single dimension value.

As used herein, "microelectrode strip or electrode strip" means that a non-conducting substrate strip on which electrodes or electrode structure units are fabricated or incorporated. The non-limiting examples of the non-conducting substrate strips include polymer membrane, glass, plastic sheets, ceramics, insulator-on-semiconductor, fiber glass (like those for manufacturing printed-circuits-board). Electrode structure units having different geometries can be fabricated or made on the substrate strip by any suitable microfabrication, micromachining, or other methods. Non-limiting examples of electrode geometries include interdigitated electrodes, circle-on-line electrodes, diamond-on-line electrodes, castellated electrodes, or sinusoidal electrodes. Characteristic dimensions of these electrode geometries may vary from as small as less than 5 micron, or less than 10 micron, to as large as over 200 micron, over 500 micron, over 1 mm. The characteristic dimensions of the electrode geometries refer to the smallest width of the electrode elements, or smallest gaps between the adjacent electrode elements, or size of a repeating feature on the electrode geometries. The microelectrode strip can be of any geometry for the present invention. One exemplary geometry for the microelectrode strips is rectangular shape—having the width of the strip between less than 50 micron to over 10 mm, and having the length of the strip between less than 60 micron to over 15 mm. An exemplary geometry of the microelectrode strips may have a geometry having a width of 200 micron and a length of 20 mm. A single microelectrode strip may have two electrodes serving as a measurement unit, or multiple such two-electrodes serving as multiple measurement units, or a single electrode structure unit as a measurement unit, or multiple electrode structure units serving as multiple electrode structure units. In one exemplary embodiment, when multiple electrode structure units are fabricated on a single microelectrode strip, these electrode structure units are positioned along the length direction of the strip. The electrode structure units may be of squared-shape, or rectangular-shape, or circle shapes. Each of electrode structure units may occupy size from less than 50 micron by 50 micron, to larger than 2 mm×2 mm.

As used herein, "sample" refers to anything which may contain a moiety to be isolated, manipulated, measured, quantified, detected or analyzed using apparatuses, microplates or methods in the present application. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

B. Devices and Systems for Monitoring Cell-Substrate Impedance

Devices for Measuring Cell-Substrate Impedance

The present invention includes devices for measuring cell-substrate impedance that comprise a nonconducting substrate; two or more electrode arrays fabricated on the substrate, where each of the two or more electrode arrays comprises two electrode structures; and at least two connection pads, each of which is located on an edge of the substrate. Each electrode array of the device has approximately uniform electrode resistance across the entire array. The substrate of the device has a surface suitable for cell attachment or growth; where cell attachment or growth on said substrate can result in a detectable change in impedance between or among the electrode structures within each electrode array.

An electrode array is two or more electrode structures that are constructed to have dimensions and spacing such that they can, when connected to a signal source, operate as a unit to generate an electrical field in the region of spaces around the electrode structures. An electrode structure refers to a single electrode, particularly one with a complex structure. (For example, an electrode structure can comprise two or more electrode elements that are electrically connected together.) In devices of the present invention, an electrode array comprises two electrode structures, each of which comprises multiple electrode elements, or substructures. In preferred embodiments of the present invention, the electrode structures of each of the two or more electrode arrays of a device have substantially the same surface area. In preferred embodiments of a device of the present invention, each of the two or more electrode arrays of a device comprise two electrode structures, and each electrode structure comprises multiple electrode elements. Each of the two electrode structures of an electrode array is connected to a separate connection pad that is located at the edge of the substrate.

Thus, in devices of the present invention, for each of the two or more electrode arrays of the device, the first of the two electrode structures is connected to one of the two or more connection pads, and the second of the two electrode structures is connected to another of the two or more connection pads. Preferably, each array of a device is individually addressed, meaning that the electrical traces and connection pads of the arrays are configured such that an array can be connected to an impedance analyzer in such a way that a measuring voltage can be applied across a single array at a given time by using switches (such as electronic switches).

Each electrode array of the device has an approximately uniform electrode resistance distribution across the entire array. By "uniform resistance distribution across the array" is meant that when a measurement voltage is applied across the electrode structures of the array, the electrode resistance at any given location of the array is approximately equal to the electrode resistance at any other location on the array. Preferably, the electrode resistance at a first location on an array of the device and the electrode resistance at a second location on the same array does not differ by more than 30%. More preferably, the electrode resistance at a first location on an array of the device and the electrode resistance at a second location on the same array does not differ by more than 15%. Even more preferably, the electrode resistance at a first location on an array of the device and a second location on the same array does not differ by more than 5%. More preferably yet, the electrode resistance at a first location on an array of the device and a second location on the same array does not differ by more than 2%.

For a device of the present invention, preferred arrangements for the electrode elements, gaps between the electrodes and electrode buses in a given electrode array are used to allow all cells, no matter where they land and attach to the electrode surfaces, to contribute similarly to the total impedance change measured for the electrode array. Thus, it is desirable to have similar electric field strengths at any two locations within any given array of the device when a measurement voltage is applied to the electrode array. At any given location of the array, the field strength is related to the potential difference between the nearest point on a first electrode structure of the array and the nearest point on a second electrode structure of the array. It is therefore desirable to have similar electric potential drops across the electrode elements and across the electrode buses of a given array. Based on this requirement, it is preferred to have an approximately uniform electrode resistance distribution across the whole array where the electrode resistance at a location of interest is equal to the sum of the electrode resistance between the nearest point on a first electrode structure (that is the point on the first electrode structure nearest the location of interest) and a first connection pad connected to the first electrode structure and the electrode resistance between the nearest point on a second electrode structure (that is the point on the first electrode structure nearest the location of interest) and a second connection pad connected to the second electrode structure.

Devices of the present invention are designed such that the arrays of the device have an approximately uniform distribution across the whole array. This can be achieved, for example, by having electrode structures and electrode buses of particular spacing and dimensions (lengths, widths, thicknesses and geometrical shapes) such that the resistance at any single location on the array is approximately equal to the resistance at any single other location on the array. In most embodiments, the electrode elements (or electrode structures) of a given array will have even spacing and be of similar thicknesses and widths, the electrode buses of a given array will be of similar thicknesses and widths, and the electrode traces leading from a given array to a connection pad will be of closely similar thicknesses and widths. Thus, in these preferred embodiments, an array is designed such that the lengths and geometrical shapes of electrode elements or structures, the lengths and geometrical shapes of electrode traces, and the lengths and geometrical shapes of buses allow for approximately uniform electrode resistance distribution across the array.

In some preferred embodiments of cell-substrate impedance measurement devices, electrode structures comprise multiple electrode elements, and each electrode element connects directly to an electrode bus. Electrode elements of a first electrode structure connect to a first electrode bus, and electrode elements of a second electrode structure connect to a second electrode bus. In these embodiments, each of the two electrode buses connects to a separate connection pad via an electrical trace. Although the resistances of the traces contribute to the resistance at a location on the array, for any two locations on the array the trace connections from the first bus to a first connection pad and from the second bus to a second connection pad are identical. Thus, in these preferred embodiments trace resistances do not need to be taken into account in designing the geometry of the array to provide for uniform resistances across the array.

Figure 1A:
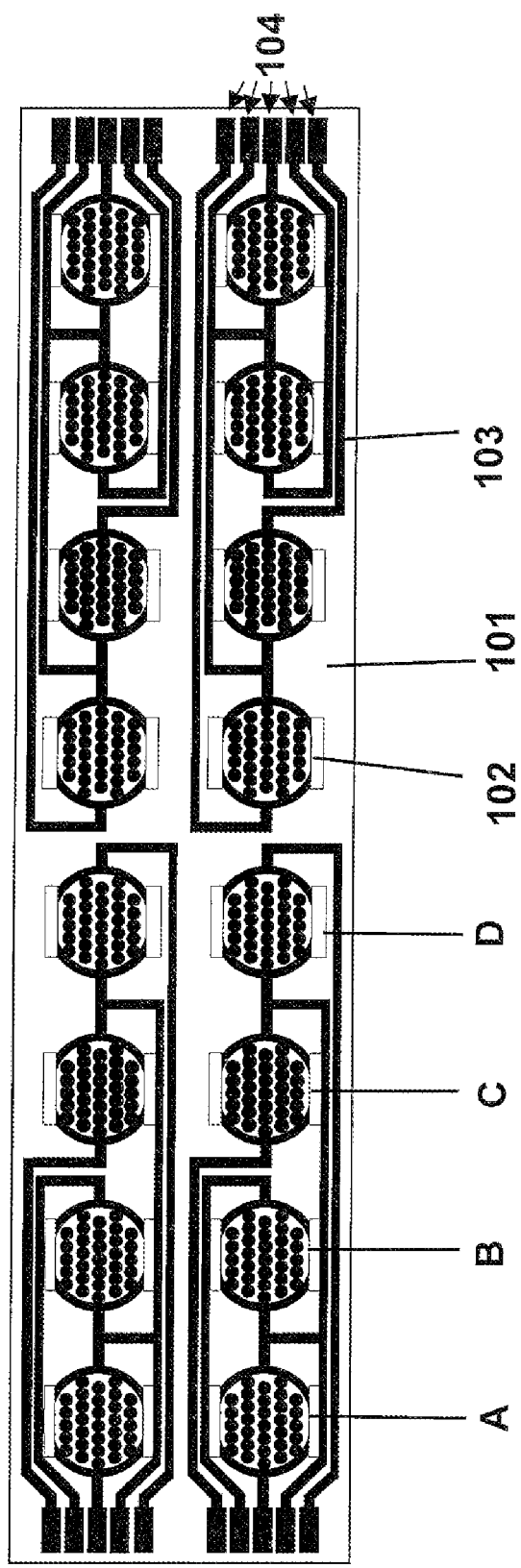
FIGS. 1A-C are schematic drawings of one design of a cell-substrate impedance measurement device of the present invention.
Figure 1B:
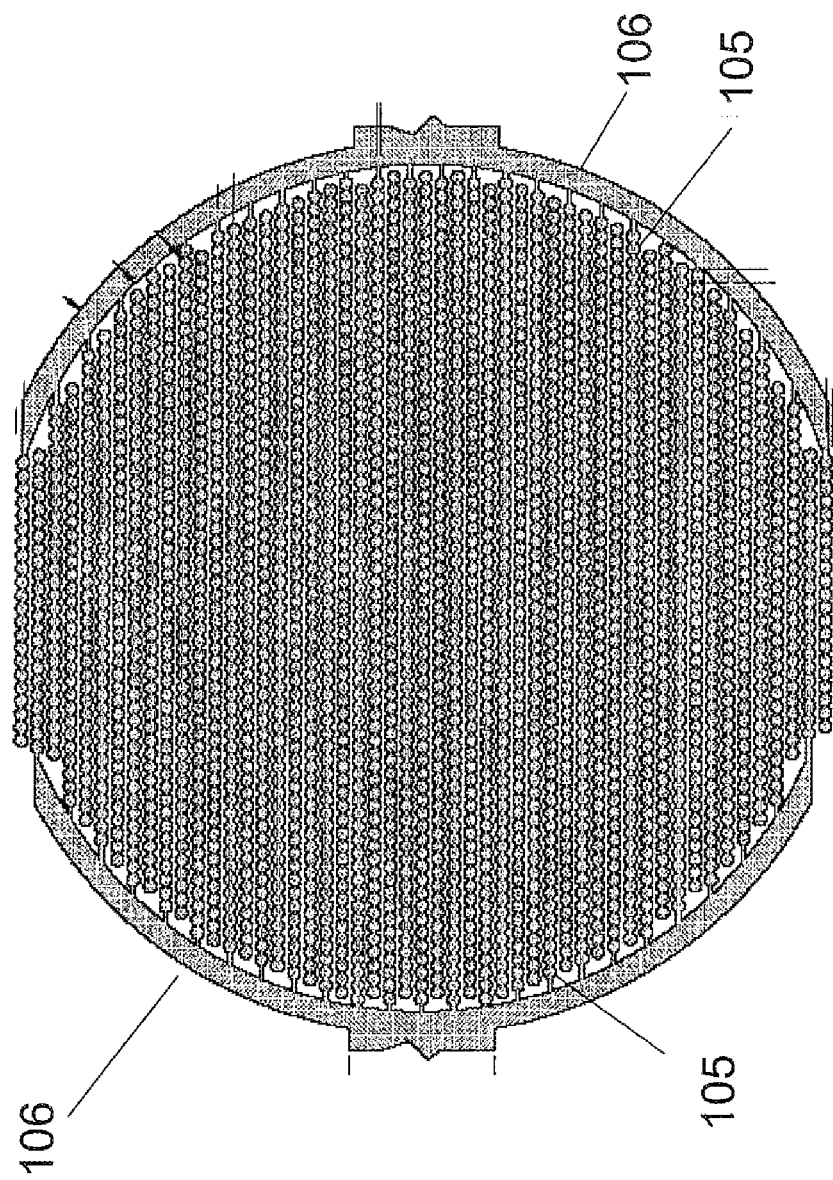
Figure 1C:
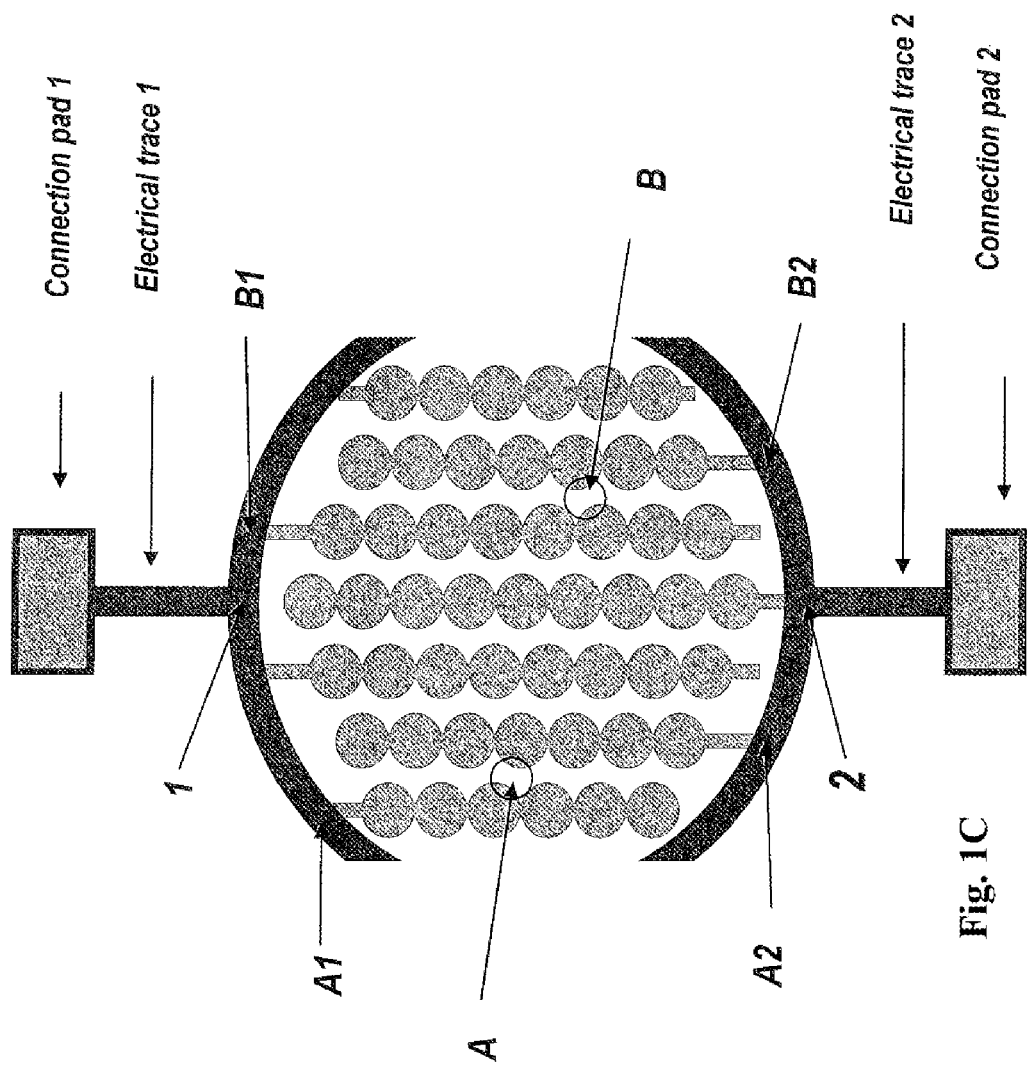

Taking the electrode array in FIG. 1C as an example, it is desirable that cells attached at location B and cells attached at location A contribute similarly to the total impedance change. Thus, it is desirable to have similar electric field strengths at location A and location B when a measurement voltage is applied to the electrode array. It is thus desirable to have similar electric potential drops across the electrode elements and across the electrode buses. Based on this requirement, it is preferred to have an approximately uniform electrode resistance distribution across the whole array where the electrode resistance at a location of interest is equal to the sum of the electrode resistances between the electrode points at the location and the two connection pads connected to the electrode array. The electrode resistance at location A and location B in FIG. 1C is given by $$R_{location\_A} = R_{trace1} + R_{1-to-A1} + R_{A1-to-A} + R_{A-to-A2} + R_{A2-to-2} + R_{trace2} \quad (1)$$

$$R_{location\_B} = R_{trace1} + R_{1-to-B1} + R_{B1-to-B} + R_{B-to-B2} + R_{B2-to-2} + R_{trace2} \quad (2)$$

where $R_{trace1}$ is the impedance (i.e., resistance, since the reaction component is very very small) of the electrical connection trace from a connection pad to location 1 on the top electrode bus; $R_{trace2}$ is the impedance (i.e., resistance, since the reaction component is very very small) of the electrical connection trace from a connection pad to location 2 on the bottom electrode bus; $R_{1-to-A1}$ is the impedance (i.e., resistance, the reaction component is very very small) between location 1 and location A1 along the top electrode bus; $R_{2-to-A2}$ is the impedance (i.e., resistance, the reaction component is very very small) between location 2 and location A2 along the bottom electrode bus; $R_{A1-to-A}$ is the impedance (i.e., resistance, the reaction component is very very small) between location A1 on the top electrode bus and location A along a connected electrode element; $R_{A2-to-A}$ is the impedance (i.e., resistance, the reaction component is very very small) between location A2 on the bottom electrode bus and location A along another connected electrode element. The requirement for an approximately uniform electrode resistance is that $R_{location\_A}$ is similar to $R_{location\_B}$.

Electrode structures shown in FIG. 1C are designed to satisfy the requirement of approximately uniform electrode resistance. In FIG. 1C, the electrodes or electrode elements are circle-on-a-line configuration with diameter of the circle being about 90 microns, the line width about 30 microns and the gaps between lines about 80 microns. The inner diameter of the electrode bus is about 5.75 mm and the outer diameter for the electrode bus is about 6.070 mm.

In preferred embodiments of the present invention, for the measurement of cell-substrate impedance, an impedance analyzer is connected indirectly through electronic switches to the connection pads on the substrate. The measured impedance $Z_{total}$ at the impedance analyzer is given by $$Z_{total} = Z_{switch} + Z_{trace} + Z_{electrode-array} \quad (3)$$

where $Z_{switch}$ is the impedance of electronic switch at its on stage, $Z_{trace}$ is the impedance of the electrical connection traces on the substrate between the connection pads and the electrode buses, $Z_{electrode-array}$ is the impedance of the electrode array with or without cell—being present. Major components of both $Z_{switch}$ and $Z_{trace}$ are electric resistance. The contribution of $Z_{switch}$ and $Z_{trace}$ to total measured impedance $Z_{total}$ can be removed from the measured impedance if these values can be determined. By choosing electronic switches of good quality, the $Z_{switch}$ values can be nearly-constant for different switches. Thus, the contribution of $Z_{switch}$ to total measured impedance $Z_{total}$ can be removed from the measured impedance. $Z_{trace}$ is somewhat difficult to remove because different electrode arrays may have different impedance values and also because there is also a thickness variation in the conductive thin film used for making the electrode structures between different devices. For accurate measurement of cell-substrate impedance, it is preferred to have small electrical connection trace (or electrical traces) impedance $Z_{trace}$. For this reason, it is desirable to have electrical traces of large width, which will lead to a reduced size for the electrode array area. For this reason, in one embodiment of the device of the presentation, in order to have reasonably wide electrical traces, the diameter of the electrode array area, as exemplified in FIG. 1B as the inner diameter of arc-shaped electrode buses, was made smaller than the bottom well diameter of a standard microtiter plate. To ensure the electrode buses are not exposed to solution during the assay, a plate having wells whose with a bottom diameter is small enough to exclude the electrode buses from the interior of the wells can be attached to the substrate.

In preferred embodiments of the present invention, a device for monitoring cell-substrate impedance has two or more electrode arrays that share a connection pad. Preferably one of the electrode structures of at least one of the electrode arrays of the device is connected to a connection pad that also connects to an electrode structure of at least one other of the electrode arrays of the device. Preferably for at least two arrays of the device, each of the two or more arrays has a first electrode structure connected to a connection pad that connects with an electrode structure of at least one other electrode array, and each of the two or more arrays has a second electrode structure that connects to a connection pad that does not connect with any other electrode structures or arrays of the device. Thus, in preferred designs of a device there are at least two electrode arrays each of which has a first electrode structure that is connected to a common connection pad and a second electrode structure that is connected to an independent connection pad.

In some preferred embodiments of the present invention, each of the electrode structures of an array is connected to an electrode bus that is connected to one of the two or more connection pads of the device via an electrically conductive trace. In preferred embodiments, each of the two electrode structures is connected to a single bus, such that each array connects to two buses, one for each electrode structures. In this arrangement, each of the two buses connects to a separate connection pad of the substrate.

The electrically conductive traces that connect a bus with a connection can be fabricated of any electrically conductive material. The traces can be localized to the surface of the substrate, and can be optionally covered with an insulating layer. Alternatively the traces can be disposed in a second plane of the substrate. Description of arrangements and design of electrically conductive traces on impedance measurement devices can be found in parent U.S. patent application Ser. No. 10/705,447, herein incorporated by reference for disclosure on fabrication and design of electrically conductive trace on substrates.

FIG. 1A shows an example of the device of the present invention. This device comprises a glass substrate (101) shown with 16 electrode arrays fabricated on the substrate. Each electrode array (102) comprises two electrode structures (shown in detail in FIG. 1B). Each electrode array connects to two electrical traces (103), with each of the two traces connected one of the two electrode structures. These electrical connection traces (103) from the electrode array (102) are connected to the connection pads (104) at the edges of the substrate (101). As shown in FIG. 1A, each the four electrode arrays in each of four quarters on the substrate (101) have one of their electrical connection traces (103) connected to a common connection pad (104). Thus, for the entire device there are four common connection pads (104), one for each quarter of the device. In addition, each electrode array has a separate electrical connection trace (103), connecting to an independent connection pad (104). Thus, there are total 20 connection pads (104) at the edges of the substrate (101).

An example of an electrode array that can be used on a device of the present invention (such as that of FIG. 1A) is depicted in FIG. 1B. Here, a single electrode array is shown. The electrode array has two electrode structures, where each electrode structure comprises multiple electrode elements (105) shown here having a circle-on-line geometry. In this electrode array structure, electrode elements (105) of one electrode structure of the array alternate with electrode elements (105) of the other electrode structure of the array. Each of the electrode structures is independently connected to its electrode bus (106), in this case, by means of direct connection of the electrode elements (105) to the electrode bus (106). Each electrode bus (106) forms an arc around the perimeter of the array, where the two buses of the array do not abut or overlap. The electrically conductive connection traces (103 in FIG. 1A) connect each bus with a connection pad (104 in FIG. 1A) on the edge of the substrate (101 in FIG. 1A)

Appropriate electronic connection means such as metal clips engaged onto the connection pads on the substrate and connected printed-circuit-boards can be used for leading the electronic connections from the connection pads on the devices to external electronic circuitry (e.g. an impedance analyzer). Description of the design of cell-substrate impedance devices and their manufacture can be found in U.S. patent application Ser. No. 10/705,447, herein incorporated by reference for description and disclosure of the design, features, and manufacture of impedance device comprising electrode arrays.

Preferably the nonconducting substrate is planar, and is flat or approximately flat. Exemplary substrates can comprise many materials, including, but not limited to, silicon dioxide on silicon, silicon-on-insulator (SOI) wafer, glass (e.g., quartz glass, lead glass or borosilicate glass), sapphire, ceramics, polymer, fiber glass, plastics, e.g., polyimide (e.g. Kapton, polyimide film supplied by DuPont), polystyrene, polycarbonate, polyvinyl chloride, polyester, polypropylene and urea resin. Preferably, the substrate and the surface of the substrate are not going to interfere with molecular binding reactions that will occur at the substrate surface. For cell-substrate impedance monitoring, any surface of the nonconducting substrate that can be exposed to cells during the use of a device of the present invention is preferably biocompatible. Substrate materials that are not biocompatible can be made biocompatible by coating with another material, such as polymer or biomolecular coating.

All or a portion of the surface of a substrate can be chemically treated, including but not limited to, modifying the surface such as by addition of functional groups, or addition of charged or hydrophobic groups.

Descriptions of electrode arrays used for impedance measurement that apply to the devices of the present invention are described in parent U.S. patent application Ser. No. 10/705,447, herein incorporated by reference for all disclosure relating to electrode arrays (or structural units), electrode structures, electrode materials, electrode dimensions, and methods of manufacturing electrodes on substrates.

Preferred electrode arrays for devices of the present invention include arrays comprising two electrode structures, such as, for example, spiral electrode arrays and interdigitated arrays. In some preferred devices of the present invention, electrode arrays are fabricated on a substrate, in which the arrays comprises two electrode structures, each of which comprises multiple circle-on-line electrode elements, in which the electrode elements of one structure alternate with the electrode elements of the opposite electrode structure. For example, FIG. 1B depicts such an array.

Preferably, the electrode elements (or electrode structures) of an array of the present device of the present invention are of approximately equal widths. Preferably the electrode elements (or electrode structures) of an array of the present device of the present invention are greater than 30 microns in width, more preferably from about 50 to about 300 microns in width, and more preferably yet about 90 microns in width.

Preferably, the electrode elements (or electrode structures) of an array of the present device of the present invention are approximately evenly spaced. Preferably, the gap between electrode elements (or electrode structures) of an array of the present device of the present invention is less than 50 microns in width, more preferably from about 5 to about 30 microns in width, and more preferably yet about 20 microns in width.

A device of the present invention can include one or more fluid-impermeable receptacles which serve as fluid containers. Such receptacles may be reversibly or irreversibly attached to or formed within the substrate or portions thereof (such as, for example, wells formed as in a microtiter plate). In another example, the device of the present invention includes microelectrode strips reversibly or irreversibly attached to plastic housings that have openings that correspond to electrode structure units located on the microelectrode strips. Suitable fluid container materials comprise plastics, glass, or plastic coated materials such as ceramics, glass, metal, etc. Descriptions and disclosure of devices that comprise fluid containers can be found in parent U.S. patent application Ser. No. 10/705,447, herein incorporated by reference for all disclosure of fluid containers and fluid container structures that can engage a substrate comprising electrodes for impedance measurements, including their dimensions, design, composition, and methods of manufacture.

In preferred embodiments, each electrode array on the substrate of a device of the present invention is associated with a fluid-impermeable container or receptacle. Preferably, the device of the present invention is assembled to a bottomless, multiwell plastic plate or strip with a fluid tight seal, as shown, for example, in FIG. 2 and FIG. 3A. The device is assembled such that a single array of the substrate is at the bottom of a receptacle or well. Preferably, each array of a device is associated with a well of a multiwell plate. In some preferred embodiments, a multiwell device for cell-substrate impedance measurement has "non-array" wells that are attached to the substrate but not associated with arrays. Such wells can optionally be used for performing non-impedance based assays, or for viewing cells microscopically.

The design and assembly of multiwell impedance measurement devices is described in parent U.S. patent application Ser. No. 10/705,447, herein incorporated by reference for disclosure of multiwell impedance measurement devices, including their design, composition, and manufacture. A device of the present invention preferably has between 2 and 1,536 wells, more preferably between 4 and 384 wells, and even more preferably, between 16 and 96 wells, all or less than all or which are associated with electrode arrays.

In some preferred embodiments, commercial tissue culture plates can be adapted to fit a device of the present invention. Bottomless plates may also be custom-made to preferred dimensions. Preferably, well diameters are from about 1 millimeter to about 20 millimeters, more preferably from about 2 millimeters to about 8 millimeters at the bottom of the well (the end disposed on the substrate). The wells can have a uniform diameter or can taper toward the bottom so that the diameter of the container at the end in contact with the substrate is smaller than the diameter of the opposing end.

Preferred Devices

The following descriptions of devices are not intended to limit the invention in any way.

FIG. 2 is an image of one design of a 16× device with a glass substrate (201) having 16 microfabricated electrode arrays mounted to a printed-circuit-board (208) via metal clips (209). The metal clips (209) are engaged onto connection pads (204) on the substrate and are soldered to the connection lines (210) on the printed-circuit-board (208). The connection lines (210) on the printed-circuit-board (208) in turn are connected to the connection pins (211) located on the edge of the device. A bottomless plastic 16 well strip (207) is bonded to the substrate (201) via a double-sided pressure sensitive adhesive, forming 16 individual fluid containers. In this device, the bottom diameter of the fluid containers is about 5 mm.

Figure 3A:
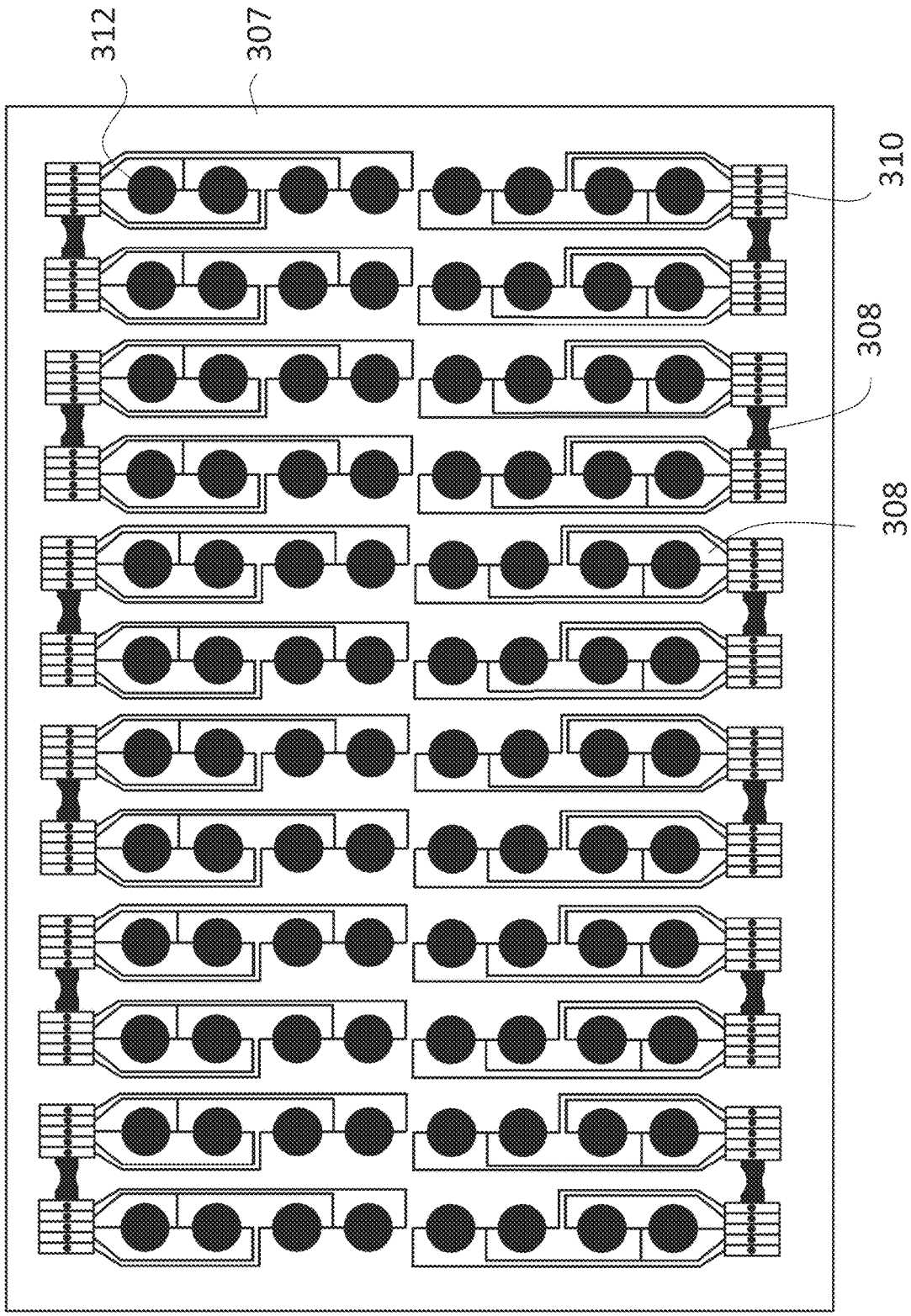
FIGS. 3A-B are images of a 96× device of the present invention.
Figure 3B:
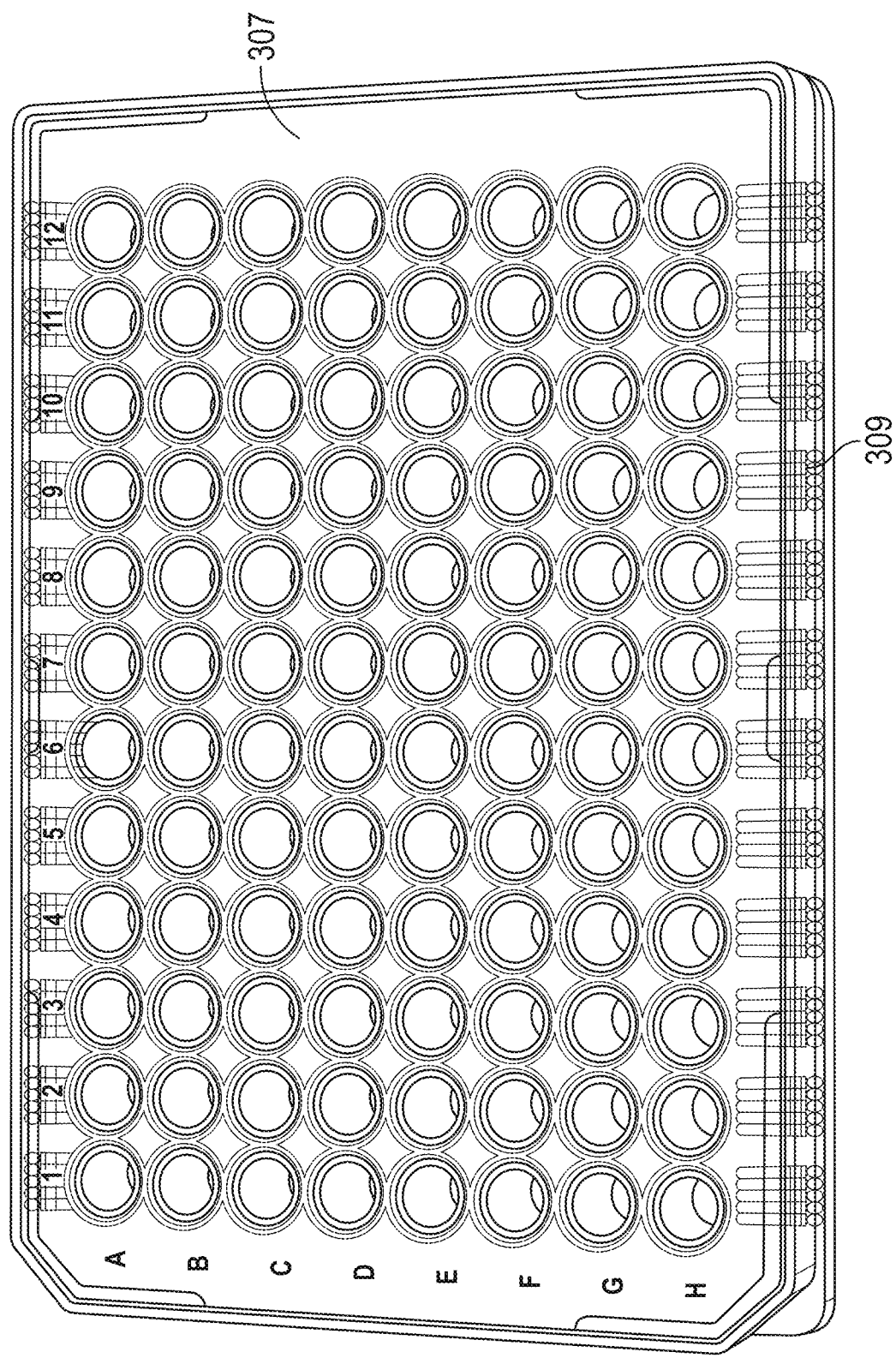

FIGS. 3A-B show an image of one design of a 96× device with six glass substrates each having either 15 or 16 microfabricated electrode arrays. FIG. 3A shows the bottom side of the device with open wells facing downwards and FIG. 3B shows the device with a plastic lid with wells open well facing upwards. The six substrates (301) are mounted and sealed to a bottomless 96 well plate (307) so that 95 of 96 wells comprise an electrode array on the bottom surface of the wells (when the open wells face upwards). One of 96 wells does not have electrodes (as indicated (312) in FIG. 3A). The well bottom diameter is about 5 mm. Metal clips are engaged onto the connection pads on the substrate and are soldered to the connection lines on the top side (when the 96-well plate is placed with open wells facing upward, as shown in FIG. 3B) of small printed-circuit-boards (308) located on the ends of the substrates (301). The printed-circuit-boards (308) are double-sided, and same number of connection lines exists on both sides of the boards at positions opposite to each other. The connection lines on the top side of the board are connected through conductive vias to connection lines on the bottom side, where the electronic connections to a device station are made.

Methods of Use

The present invention also includes methods of using a device of the present invention that comprises fluid containers situated over electrode arrays to measure cell-substrate impedance. Such methods include: providing a device of the present invention that comprises fluid containers situated over electrode arrays, attaching an impedance analyzer to a device of the present invention, adding cells to one or more fluid containers of the device, and measuring impedance over one or more arrays of the device. Methods of performing cell assays using impedance measurement devices can be found in parent U.S. patent application Ser. No. 10/705,447, herein incorporated by reference for its disclosure of methods of using impedance measurement devices, as well as in Sections D and E of the present application.

Cell-Substrate Impedance Measurement Systems

In another aspect, the present invention is directed to a cell-substrate impedance measurement system comprising a) at least one multiple-well cell-substrate impedance measuring device, in which at least two of the multiple wells comprise an electrode array at the bottom of the well; b) an impedance analyzer electronically connected to the multiple-well cell-substrate impedance measuring device; c) a device station capable of engaging the one or more multiple-well devices and comprising electronic circuitry capable of selecting and connecting electrode arrays within any of the multiple wells to the impedance analyzer; and d) a software program connected to the device station and impedance analyzer to control the device station and perform data acquisition and data analysis from the impedance analyzer.

In a cell-substrate impedance measurement system of the present invention, the impedance analyzer engages connection pads of one or more multi-well devices to measure impedance. A cell-substrate measurement system can be used to efficiently and simultaneously perform multiple assays by using circuitry of the device station to digitally switch from recording from measuring impedance over an array in one well to measuring impedance over an array in another well.

A multiple-well cell-substrate impedance measuring device in a system of the present invention can be any multiple-well cell-substrate impedance measuring device in which at least two of the multiple wells comprise an electrode array at the bottom of the well, and in which at least two of the multiple wells comprise an electrode array are individually addressed. A device used in a system of the present invention, when connected to an impedance analyzer, can measure differences in impedance values that relate to cell behavior. For example, a cell-substrate impedance measuring device used in a system of the present invention can measure differences in impedance values when cells are attached to the electrode array and when cells are not attached to the electrode array, or can detect differences in impedance values when the number, type, activity, adhesiveness, or morphology of cells attached to the electrode-comprising surface of the apparatus changes.

Preferred devices that can be part of a cell-substrate impedance monitoring system can be those described in parent U.S. patent application Ser. No. 10/705,447, herein incorporated by reference for disclosure of cell-substrate impedance monitoring devices that comprise electrode arrays, including disclosure of their design, composition, and manufacture. Preferred devices that can be part of a cell-substrate impedance monitoring system can also be those described in the present application.

Preferably a multi-well device of a system of the present invention comprises between 4 and 1,536 wells, some or all of which can comprise electrode arrays. In some embodiments of the present invention, a device station can comprise one or more platforms or one or more slots for positioning one or more multiwell devices. The one or more platforms or one or more slots can comprise sockets, pins or other devices for electrically connecting the device to the device station. The device station preferably can be positioned in a tissue culture incubator during cell impedance measurement assays. It can be electrically connected to an impedance analyzer and computer that are preferably located outside the tissue culture incubator.

The device station comprises electronic circuitry that can connect to an impedance monitoring device and an impedance analyzer and electronic switches that can switch on and off connections to each of the two or more electrode arrays of the multiwell devices used in the system. The switches of the device station are controlled by a software program. The software program directs the device station to connect arrays of the device to an impedance analyzer and monitor impedance from one or more of the electrode arrays. During impedance monitoring, the impedance analyzer can monitor impedance at one frequency or at more than one frequency. Preferably, impedance monitoring is performed at more than one time point for a given assay, and preferably, impedance is monitored at at least three time points. The device station can connect individual arrays of a device to an impedance analyzer to monitor one, some, or all of the arrays of a device for a measurement time point. The switches of the device station allow the selected individual arrays to be monitored in rapid succession for each desired monitoring time point. Each monitoring time point is in fact a narrow time frame (for example from less than one second to minutes) of measurement in the assay during which impedance monitoring is performed. In some preferred embodiments of the present invention, the device station software is programmable to direct impedance monitoring of any of the wells of the device that comprise arrays at chosen time intervals.

The software of the impedance monitoring system can also store and display data. Data can be displayed on a screen, as printed data, or both. Preferably the software can allow entry and display of experimental parameters, such as descriptive information including cells types, compound concentrations, time intervals monitored, etc.

Preferably, the software can also analyze impedance data. In preferred embodiments, the software can calculate a cell index for one or more time points for one or more wells of the multiwell device.

Figure 4:
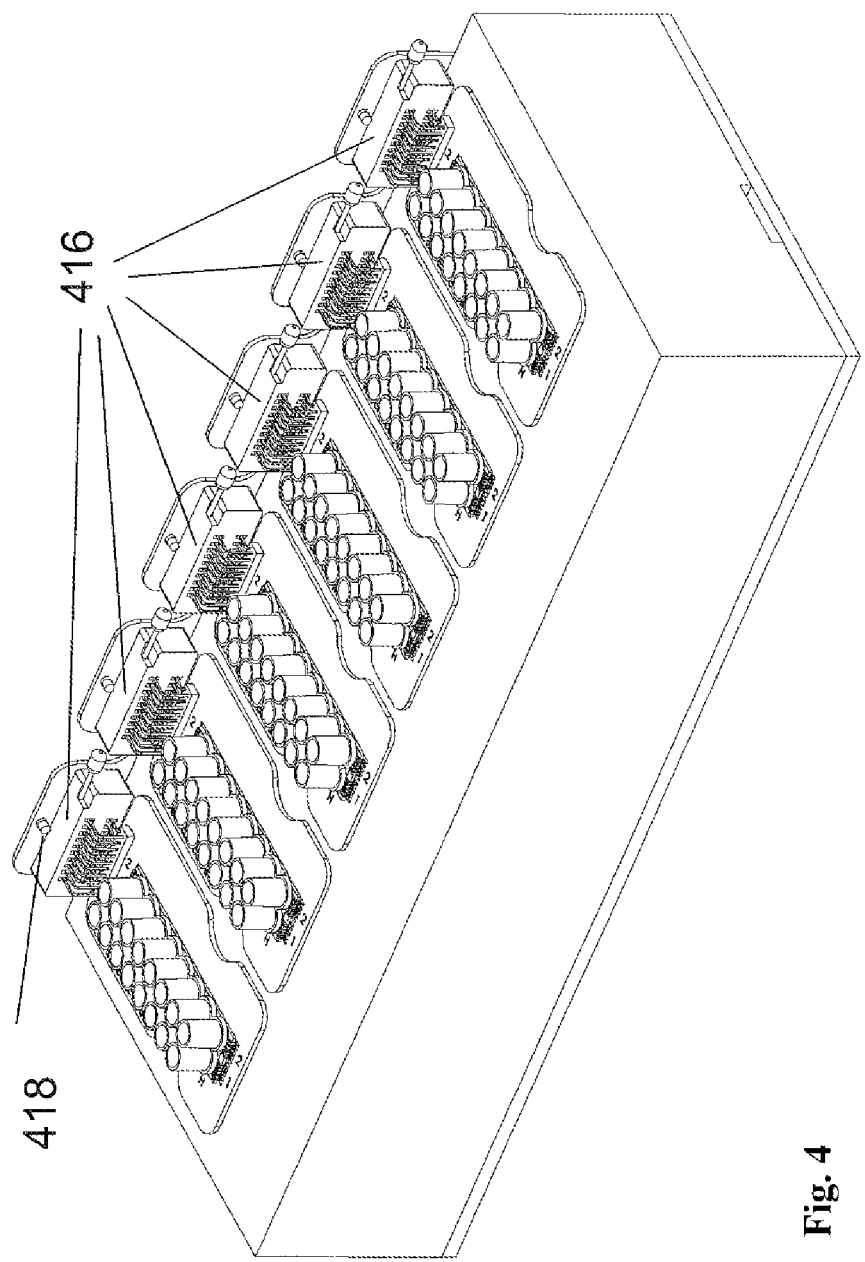
FIG. 4 shows one design of a 16× device station with 6 16× devices connected to the station.

FIG. 4 shows one design of a 16× device station with 6 16 well devices connected to the station. The device station has six individual slots for six devices, in which each slot comprises a zero-insertion force socket (416) with connection indicators (418). When a device is properly engaged with the device station, a light (418) will be on because the light indicator (418) will be connected through circuit lines on the PCB of the device to an electrical power source. The station comprises electronic switches that can be switched on (connected) or off (disconnected) digitally to connect electrode arrays in individual wells to an impedance analyzer.

Figure 5:
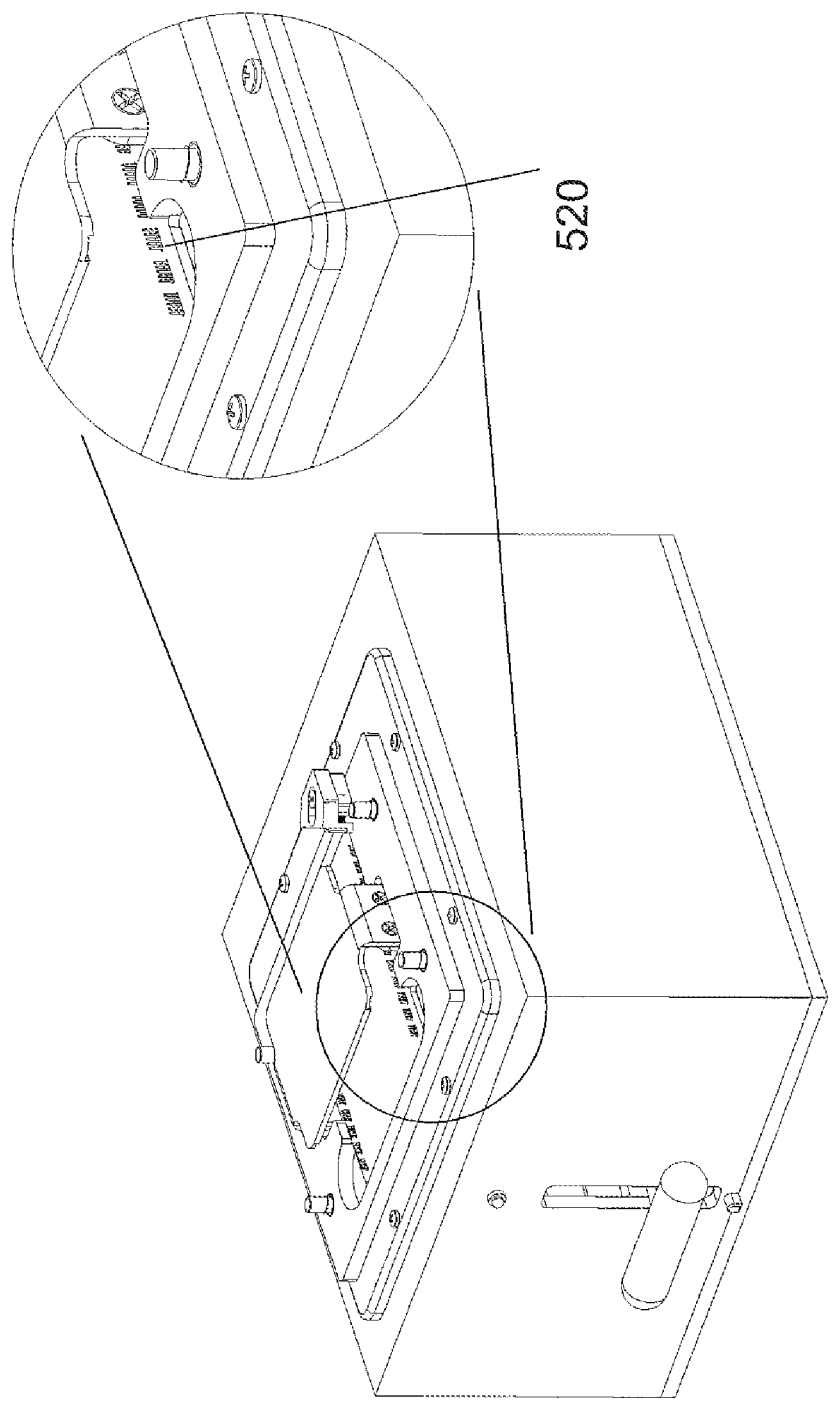
FIG. 5 shows one design of a 96× device station with a 96-well plate placed on the station.

FIG. 5 shows a 96 well device station with that can engage the 96-well device depicted in FIGS. 3A-B. The station uses POGO pins (520) to connect to the connection lines on small printed-circuit-boards (the device has small PCBs connected to connection pads on the edges of the device with metal clips. The POGO-pins (520) are connected a circuitry inside the device station. The circuitry comprises electronic switches that can be switched on (connected) or off (disconnected) digitally to connect electrode arrays in those electrode-containing wells to an impedance analyzer.

Figure 6A:
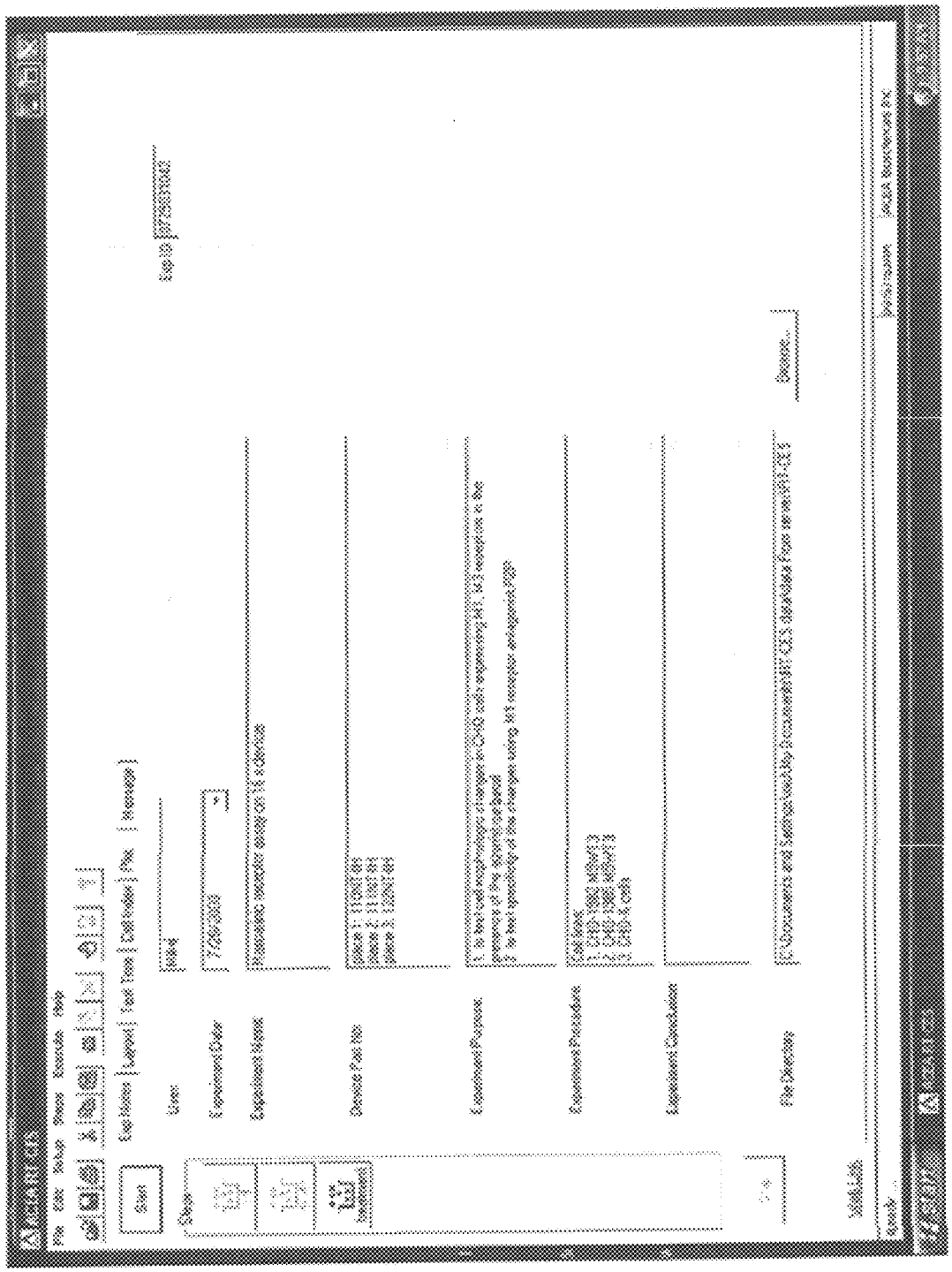
Figure 6B:
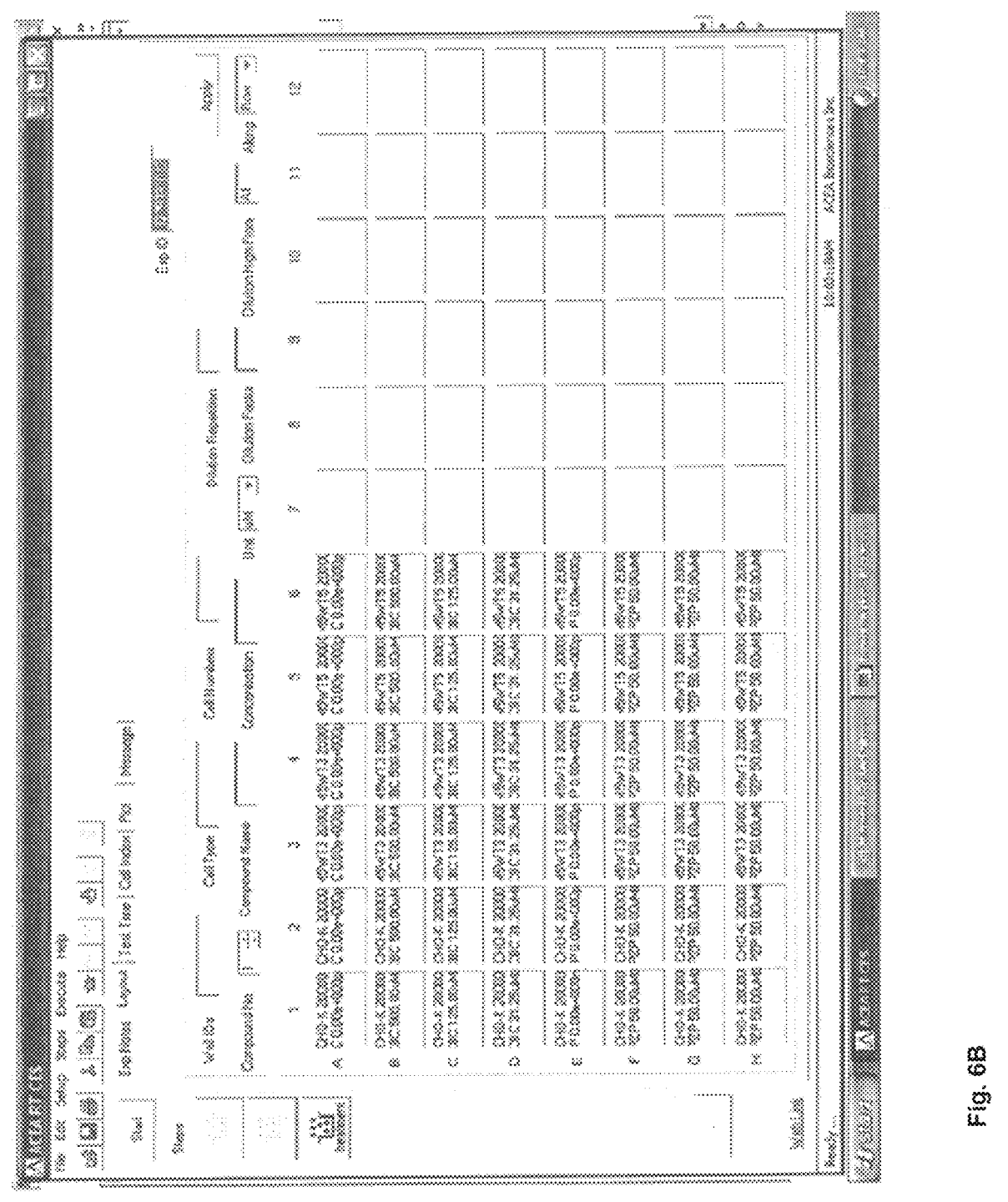
Figure 6C:
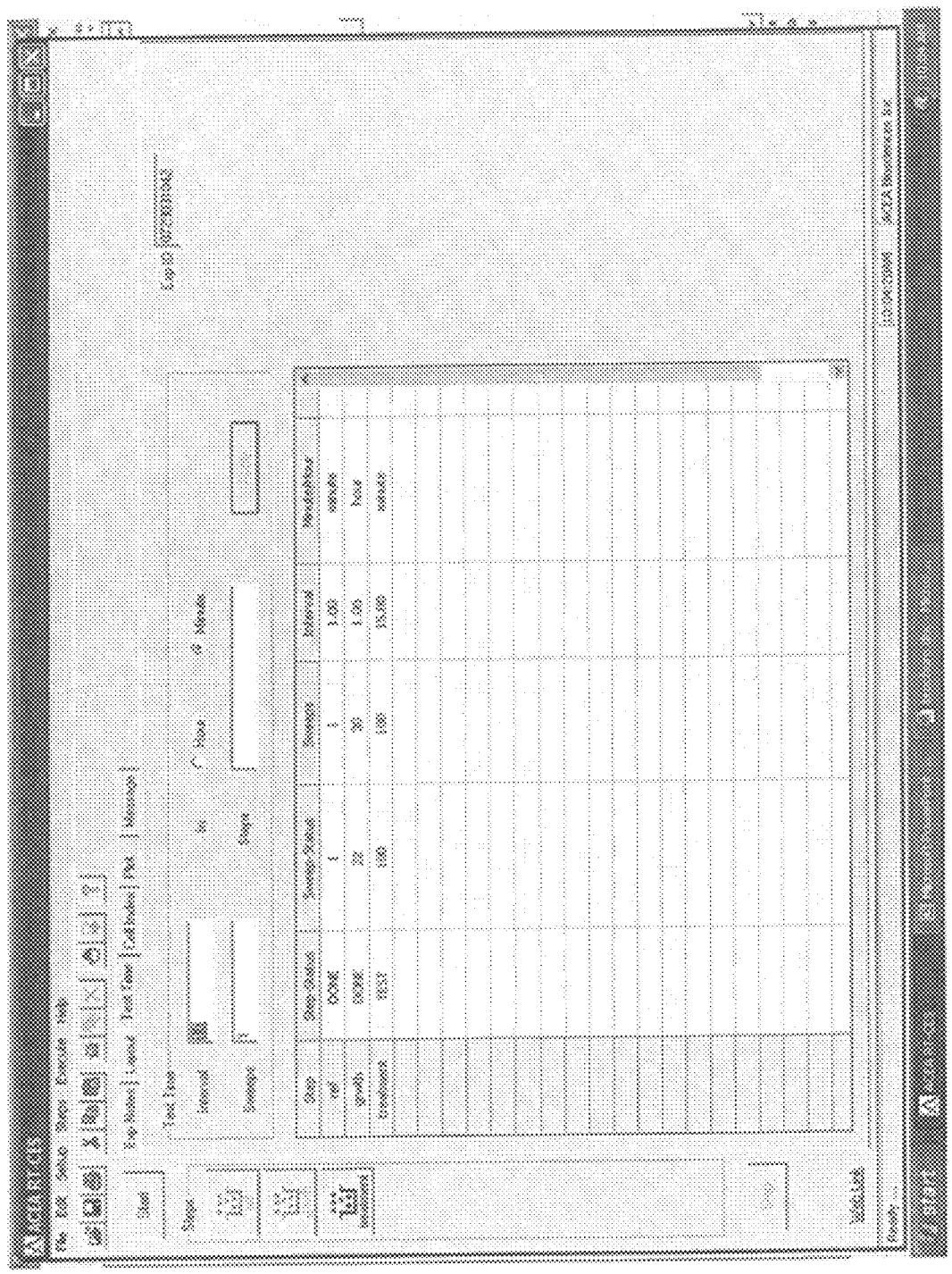
Figure 6D:
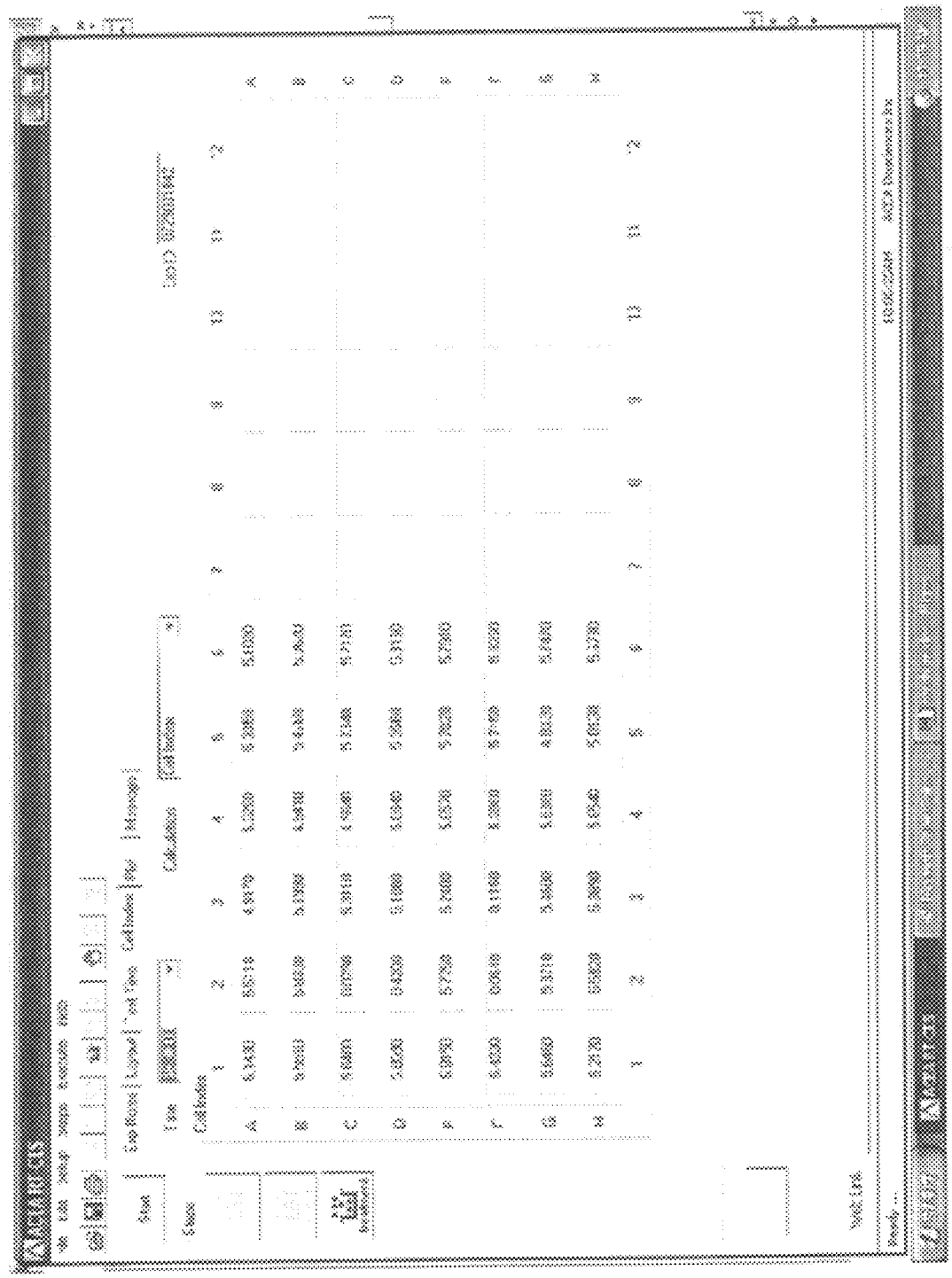
Figure 6E:
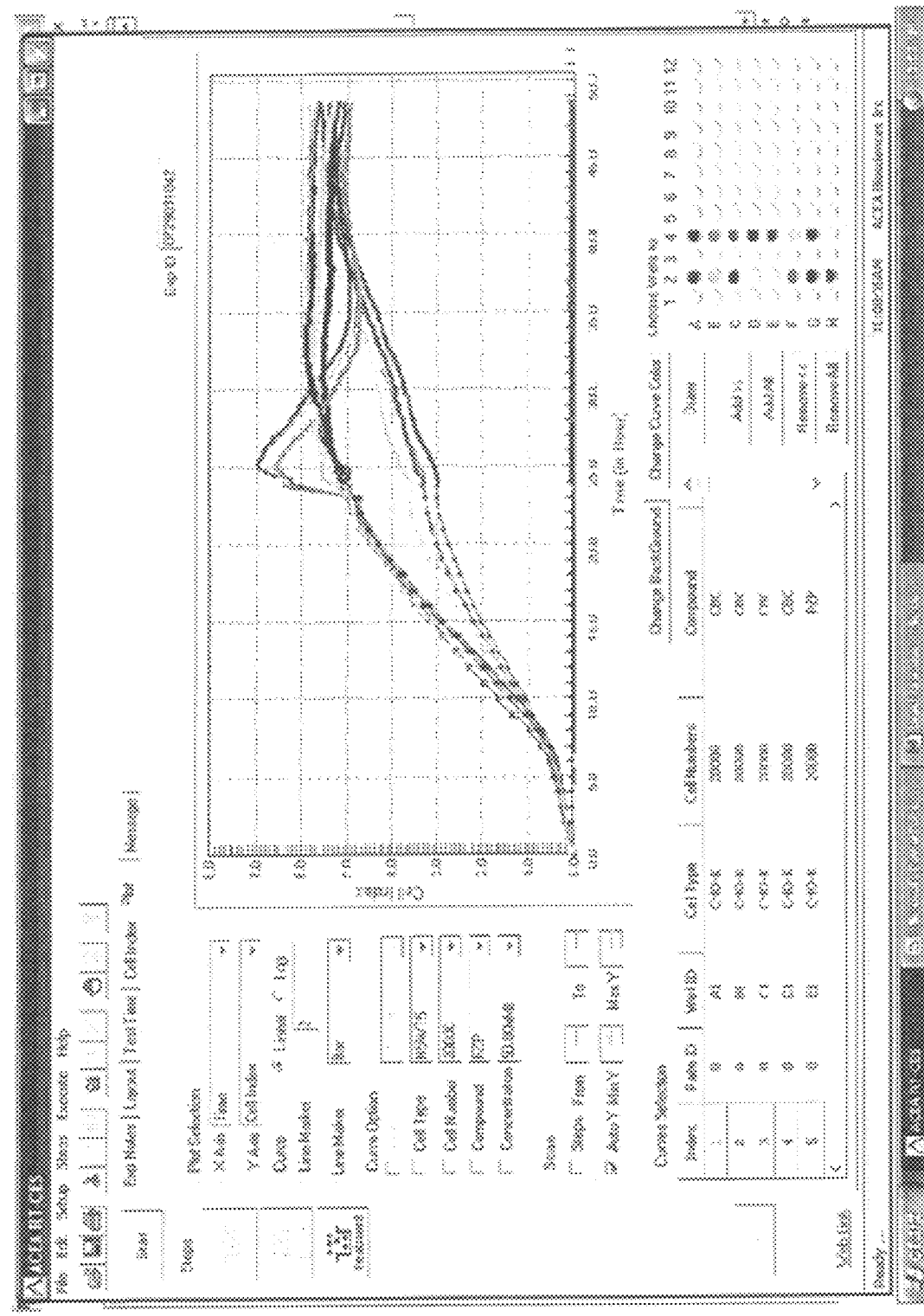

FIGS. 6A-E show different pages from real-time cell electronic sensing software, illustrating the entry of experimental parameters that can be entered and the display of results of data analysis. In FIG. 6A, an experimental note page allows the recording of key information about the experiment by the experimenter, such as the goals and procedures of the experiment. In FIG. 6B, an experimental layout page allows the recording of cells, cell number, compound and compound concentration added into each well. In FIG. 6C, a test time setting page allows for the recording and control of time intervals used for performing cell-substrate impedance measurement and multiple experimental steps each having different time interval values and different length times can be setup. In FIG. 6D, a cell index page is a result page where the software automatically update the measured and derived cell index values for all wells that are under test after the completion of each measurement at predetermined time interval as setup by the Test time setting page. In FIG. 6E, an experimental data plot page allows for flexible plotting and organization of experimental data.

C. Methods for Calculating Cell Index

Based on the dependent relationship between the measured impedance, cell number (more accurately, the viable cell number, or attached cell number) and cell attachment status, it is possible to derive a so-called "cell number index" or "cell index" from the measured impedance frequency spectra that provides a useful index for quantitating and comparing cell behavior in the impedance-based assays of the present invention. In some applications of the present invention, "cell index" in the present application is the same as "cell number index" in PCT Application No. PCT/US03/22557, entitled "IMPEDANCE BASED DEVICES AND METHODS FOR USE IN ASSAYS", filed on Jul. 18, 2003 and in U.S. patent application Ser. No. 10/705,447, entitled "IMPEDANCE BASED DEVICES AND METHODS FOR USE IN ASSAYS", filed on Nov. 10, 2003. U.S. patent application Ser. No. 10/705,447 and PCT Application No. PCT/US03/22557 are hereby incorporated by reference for the discussions and disclosures of cell index and cell number index they contain.

Various methods for calculating such a cell number index can be used, some of which are novel methods disclosed herein.

The present invention provides several methods of calculating cell index numbers for cells attached to two or more essentially identical arrays of a cell-substrate impedance device, where the cells are monitored for impedance changes. In preferred embodiments of the present invention, the methods calculate cell index number with better accuracy than previous methods of calculating cell index for cells on two or more arrays of a cell-substrate monitoring device. In some preferred methods of the present invention, methods of calculating a cell index rely on novel methods for calculating the resistances of electrical traces leading to two or more essentially identical arrays. The present invention therefore also includes methods of calculating resistances of electrical traces leading to two or more essentially identical arrays on a substrate.

By "essentially identical electrode arrays" or "essentially identical arrays" is meant that the dimensions and arrangement of electrodes, electrode structures, and electrode elements is the same for the referenced arrays. Thus, two essentially identical electrode arrays will have electrode structures of the same dimensions (length, width, thickness), where the electrode structures have the same number of electrode elements, and the arrangement of electrode structures and electrode elements in each array are the same. By arrangement is meant the distance between structures or elements (gap width), their physical position with respect to one another, and their geometry (angles, degree of curvature, circle-on-line or castellated geometries, etc.), including the same features of any electrode buses that may be connected to electrode structures or electrode elements. Electrodes of essentially identical arrays also comprise the same materials. For the purposes of calculating trace resistances and cell index number, a substrate can have any number of essentially identical arrays.

The following discussion provides novel methods of calculating cell index of cells adhered to arrays of a cell-substrate impedance monitoring device and novel methods for the calculation of the resistances of the electrical connection traces leading to two or more electrode arrays of a cell-substrate impedance monitoring device.

Impedance (Z) has two components, namely the resistance Rs and reactance Xs. Mathematically, the impedance Z is expressed as follows, $$Z = Rs + j\, Xs,$$

where $j=\sqrt{-1}$, depicting that for the (serial) reactance component Xs, the voltage applied over it is 90 degree phased-out from the current going through it. For the (serial) resistance, the voltage applied over it is in phase with the current going through it. As it is well-known in electronic and electrical engineering, the impedance can also be expressed in terms of parallel resistance Rp and parallel reactance Xp, as follows, $$Z = Rp*(j\, Xp)/(Rp + j\, Xp),$$

where $j=\sqrt{-1}$. Nevertheless, these expressions (serial resistance and serial reactance, or parallel resistance and parallel reactance) are equivalent. Those who are skilled in electrical and electronic engineering can readily derive one form of expression from the parameter values in the other expression. For the sake of clarity and consistency, the description and discussion in the present invention utilizes the expression of serial resistance and serial reactance. For simplicity, serial resistance and serial reactance are simply called resistance and reactance.

As described in U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, both of which are herein incorporated by reference for disclosures relating to cell-substrate impedance monitoring, monitoring cell-substrate impedance for detection or measurement of change in impedance can be done by measuring impedance in any suitable range of frequencies. For example, the impedance can be measured in a frequency range from about 1 Hz to about 100 MHz. In another example, the impedance can be measured in a frequency range from about 100 Hz to about 2 MHz. The impedance is typically a function of the frequency, i.e., the impedance values change as frequency changes. Monitoring cell-substrate impedance can be done either in a single frequency or multiple frequencies. If the impedance measurement is performed at multiple frequencies, then a frequency-dependent impedance spectrum is obtained—i.e., there is an impedance value at each measured frequency. As mentioned above, the impedance has two components—a resistance component and a reactance component. A change in either resistance component or reactance component or both components can constitute a change in impedance.

As described in the U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, herein incorporated by reference for disclosure of methods of measuring electrical impedance, the method for the measurement of electrical (or electronic) impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. As it is well-known in electrical and electronic engineering, in such calculations (e.g. divisions mentioned above), the current amplitude and voltage amplitude are expressed in the form of complex numbers, which take into account of how big the current and the voltage are and what the phase difference between the sinusoidal waves of the current and the voltage is. Similarly, the impedance value is also expressed in a complex form, having both resistance and reactance component, as shown in equations above.

As described in the U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, both incorporated herein by reference for disclosure relating to Cell Index or Cell Number Index, the measured cell-substrate impedance can be used to calculate a parameter termed Cell Index or Cell Number Index. Various methods for calculating such a cell number index can be used based on the changes in resistance or reactance when cells are attached to the electrode structures with respect to the cases no cells are attached to the electrode structures. The impedance (resistance and reactance) of the electrode structures with no cell attached but with same cell culture medium over the electrode structures is sometimes referred as baseline impedance. The baseline impedance may be obtained by one or more of the following ways: (1) the impedance measured for the electrode structures with a cell-free culture medium introduced into the well containing the electrode structures, wherein the culture medium is the same as that used for the impedance measurements for the condition where the cell attachment is monitored; (2) the impedance measured shortly (e.g. 10 minutes) after the cell-containing medium was applied to the wells comprising the electrode structures on the well bottom (during the short period after cell-containing medium addition, cells do not have enough time to attach to the electrode surfaces. The length of this short-period may depend on cell type and/or surface treatment or modification on the electrode surfaces); (3) the impedance measured for the electrode structures when all the cells in the well were killed by certain treatment (e.g. high-temperature treatment) and/or reagents (e.g. detergent) (for this method to be used, the treatment and/or reagents should not affect the dielectric property of the medium which is over the electrodes).

In one example (A), the cell index or cell number index can be calculated by:
(A1) at each measured frequency, calculating the resistance ratio by dividing the resistance of the electrode arrays when cells are present and/or attached to the electrodes by the baseline resistance,
(A2) finding or determining the maximum value in the resistance ratio over the frequency spectrum,
(A3) and subtracting one from the maximum value in the resistance ratio.

Using a mathematically formula, Cell Index is derived as $$\text{Cell Index} = \max_{i=1,2,\ldots N}\left(\frac{R_{cell}(f_i)}{R_b(f_i)} - 1\right) \quad (4)$$

Where N is the number of the frequency points at which the impedance is measured. For example, if the frequencies used for the measurements are at 10 kHz, 25 kHz and 50 kHz, then $N=3, f_1=10$ kHz, $f_2=25$ kHz, $f_3=50$ kHz. $R_{cell}(f_i)$ is the resistance (cell-substrate resistance) of the electrode arrays or electrode structures when the cells are present on the electrodes at the frequency $f_i$ and $R_b(f_i)$ is the baseline resistance of the electrode array or structures at the frequency $f_i$.

In this case, a zero or near-zero "cell index or cell number index" indicates that no cells or very small number of cells are present on or attached to the electrode surfaces. A higher value of "cell number index" indicates that, for same type of the cells and cells under similar physiological conditions, more cells are attached to the electrode surfaces. A higher value of "cell index" may also indicate that, for same type of the cells and same number of the cells, cells are attached better (for example, cells spread out more, or cell adhesion to the electrode surfaces is stronger) on the electrode surfaces.

In another example (B), the cell number index can be calculated by:
(B1) at each measured frequency, calculating the reactance ratio by dividing the reactance of the electrode arrays when cells are present on and/or attached to the electrodes by the baseline reactance,
(B2) finding or determining the maximum value in the reactance ratio over the frequency spectrum,
(B3) and subtracting one from the maximum value in the resistance ratio.

In this case, a zero or near-zero "cell number index" indicates that no cells or very small number of cells are present on or attached to the electrode surfaces. A higher value of "cell number index" indicates that, for same type of the cells and cells under similar physiological conditions, more cells are attached to the electrode surfaces.

In yet another example (C), the cell index can be calculated by:
(C1) at each measured frequency, subtracting the baseline resistance from the resistance of the electrode arrays when cells are present or attached to the electrodes to determine the change in the resistance with the cells present relative to the baseline resistance;
(C2) then finding or determining the maximum value in the change of the resistance.

In this case, "cell-number index" is derived based on the maximum change in the resistance across the measured frequency range with the cells present relative to the baseline resistance. This cell index would have a dimension of ohm.

In yet another example (D), the cell index can be calculated by:
(D1) at each measured frequency, calculating the magnitude of the impedance (equaling to $\sqrt{R_s^2+X_s^2}$, where $R_s$ and $X_s$ are the serial resistance and reactance, respectively).
(D2) subtracting the magnitude of the baseline impedance from the magnitude of the impedance of the electrode arrays when cells are present or attached to the electrodes to determine the change in the magnitude of the impedance with the cells present relative to the baseline impedance;
(D3) then finding or determining the maximum value in the change of the magnitude of the impedance.

In this case, "cell-number index" is derived based on the maximum change in the magnitude of the impedance across the measured frequency range with the cells present relative to the baseline impedance. This cell index would have a dimension of ohm.

In yet another example (E), the index can be calculated by:
 (E1) at each measured frequency, calculating the resistance ratio by dividing the resistance of electrode arrays when cells are present or attached to the electrodes by the baseline resistance,
 (E2) then calculating the relative change in resistance in each measured frequency by subtracting one from the resistance ratio,
 (E3) then integrating all the relative-change value (i.e., summing together all the relative-change values at different frequencies).

In this case, "cell-number index" is derived based on multiple-frequency points, instead of single peak-frequency like above examples. Again, a zero or near-zero "cell number index" indicates that on cells are present on the electrodes. A higher value of "cell number index" indicates that, for same type of the cells and cells under similar physiological conditions, more cells are attached to the electrodes.

In yet another example (F), the cell index can be calculated by:
 (F1) at each measured frequency, subtracting the baseline resistance from the resistance of the electrode arrays when cells are attached to the electrodes to determine the change in the resistance with the cells present relative to the baseline impedance; (here the change in the resistance is given by $\Delta R(f_i)=R_{s\text{-}cell}(f_i)-R_{s\text{-}baseline}(f_i)$ for the frequency $f_i$, $R_{s\text{-}cell}$ and $R_{s\text{-}baseline}$ are the serial resistances with the cells present on the electrode array and the baseline serial resistances, respectively);
 (F2) analyzing the frequency dependency of the change of the resistance to derive certain parameters that can quantify such dependency. In one example, such parameters can be calculated as $$\sqrt{\sum_i [\Delta R(f_i)]^2}.$$

In another example, such parameter can be calculated as $$\sum_i |\Delta R(f_i)|.$$

The parameter(s) are used as cell index or cell number index.

In this case, "cell-number index" is derived based on the analysis of the frequency spectrum of the change in the resistance. Depending how the parameters are calculated, the cell index may have a dimension of ohm.

In yet another example (G), the cell index can be calculated by:
 (G1) at each measured frequency, calculating the magnitude of the impedance (equaling to $\sqrt{R_s^2+X_s^2}$, where $R_s$ and $X_s$ are the serial resistance and reactance, respectively).
 (G2) subtracting the magnitude of the baseline impedance from the magnitude of the impedance of the electrode arrays when cells are attached to the electrodes to determine the change in the magnitude of the impedance with the cells present relative to the baseline impedance; (here, the change in the magnitude of the impedance is given by $\Delta Z(f_i)=|Z_{cell}(f_i)|-|Z_{baseline}(f_i)|$ for the frequency $f_i$, $|Z_{cell}(f_i)|=\sqrt{R_{s\text{-}cell}(f_i)^2+X_{s\text{-}cell}(f_i)^2}$, $R_{s\text{-}cell}$ and $X_{s\text{-}cell}$ being the serial resistance and reactance with the cells present on the electrode arrays, respectively, $|Z_{cell}(f_i)|$ is the magnitude of the impedance of the electrode array with cells present on the electrode arrays, $|Z_{baseline}(f_i)|$ is the magnitude of the baseline impedance of the electrode array);
 (G3) analyzing the frequency dependency of the change of the magnitude of the impedance to derive certain parameters that can quantify such dependency. In one example, such parameters can be calculated as $$\sqrt{\sum_i [\Delta Z(f_i)]^2}.$$

In another example, such parameter can be calculated as $$\sum_i |\Delta Z(f_i)|.$$

The parameter(s) are used as cell index or cell number index.

In this case, "cell-number index" is derived based on the analysis of the frequency spectrum of the change in the magnitude of the impedance. Depending how the parameters are calculated, the cell index may have a dimension of ohm.

As described in the U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, both herein incorporated by reference for disclosure of Cell Index or Cell Number Index and its calculation, there are different methods for calculating the parameter termed Cell Index or Cell Number Index from the measured cell-substrate impedance (resistance or reactance). Cell Index or Cell Number Index is a quantitative measure of cells in the wells under cell-substrate impedance measurement.

It is worthwhile to point out that it is not necessary to derive such a "cell number index" for utilizing the impedance information for monitoring cell conditions over the electrodes. Actually, one may choose to directly use impedance values (e.g., at a single fixed frequency; or at a maximum relative-change frequency, or at multiple frequencies) as an indicator of cell conditions.

Still, deriving "cell index" or "cell number index" and using such index to monitor cell conditions may have advantages. There are several advantages of using "cell number index" to monitor cell growth and/or attachment and/or viability conditions.

First, one can compare the performance of different electrode geometries by utilizing such cell number index.

Secondly, for a given electrode geometry, it is possible to construct "calibration curve" for depicting the relationship between the cell number and the cell number index by performing impedance measurements for different number of cells added to the electrodes (in such an experiment, it is important to make sure that the seeded cells have well-attached to the electrode surfaces). With such a calibration curve, when a new impedance measurement is performed, it is then possible to estimate cell number from the newly-measured cell number index.

Thirdly, cell number index can also be used to compare different surface conditions. For the same electrode geometry and same number of cells, a surface treatment given a larger cell number index indicates a better attachment for the cells to the electrode surface and/or better surface for cell attachment.

As shown above, for some methods of calculating cell index or cell number index, it is important to know the impedance (resistance and/or reactance) of the electrode structures with and without cells present on them. Based on the equation (1), the impedance of the electrode array (with or without cells present on the electrodes) is given by $$Z_{electrode\text{-}array} = Z_{total} - Z_{trace} - Z_{switch} \quad (5)$$

Where $Z_{switch}$ is the impedance of electronic switch at its on stage, $Z_{trace}$ is the impedance of the electrical connection traces (or electrical conductive traces) on the substrate between the connection pads and the electrode buses, $Z_{total}$ is the total impedance measured at the impedance analyzer. By choosing electronic switches with good quality, it is possible to have all the electronic switches have a consistent on-impedance (mainly resistance). For example, the on-resistance of electronic switches can be about 3 ohm (+/− 10%) with the on reactance being negligible (for example, less than 0.2 ohm in the frequency range of interest). Thus, if the trace impedance is determined or calculated, then formula (5) can be used to calculate the impedance of the electrode arrays with or without cells present.

A method is invented in the present application to determine the impedance of electrical conductive (electrical connection) traces (mainly trace resistance, trace reactance is very small for the thin conductive film trace) based on the relationships among two or more essentially identical arrays on a cell-substrate impedance monitoring device. In the following, the four electrode arrays A, B, C and D as indicated in FIG. 1A, are used to illustrate this method. The electrical reactance (serial reactance) of the electronic switches and the electrical reactance (serial reactance) of the electrical connection traces are small as compared with the corresponding electrical resistances (serial resistances). Thus, we focus on the analysis of the resistance of the electrical connection traces. The impedance determined from the impedance analyzer does contain both resistance (serial resistance, $R_{total}$) and reactance (serial reactance). For the electrode arrays A-D, the measured total resistance $R_{total}$, the resistance ($R_{trace}$) of electrical conductive (connection) trace, the switch resistance ($R_{switch}$) and the resistance ($R_{e\text{-}array}$) of the electrode array satisfy the following equations:

$$R_{e\text{-}array\text{-}A} = R_{total\text{-}A} - R_{trace\text{-}A} - R_{switch\text{-}A} \quad (6A)$$

$$R_{e\text{-}array\text{-}B} = R_{total\text{-}B} - R_{trace\text{-}B} - R_{switch\text{-}B} \quad (6B)$$

$$R_{e\text{-}array\text{-}C} = R_{total\text{-}C} - R_{trace\text{-}C} - R_{switch\text{-}C} \quad (6C)$$

$$R_{e\text{-}array\text{-}D} = R_{total\text{-}D} - R_{trace\text{-}D} - R_{switch\text{-}D} \quad (6D)$$

With chosen electronic switches having consistent switch-on resistance, $R_{switch\text{-}A}$, $R_{switch\text{-}B}$, $R_{switch\text{-}C}$ and $R_{switch\text{-}D}$ have very similar values and can be assumed to be the same, $R_{switch}$. Thus, in above equations, the known parameters are $R_{total\text{-}A}$, $R_{total\text{-}B}$, $R_{total\text{-}C}$, and $R_{total\text{-}D}$, and $R_{switch\text{-}A}$, $R_{switch\text{-}B}$, $R_{switch\text{-}C}$ and $R_{switch\text{-}D}$, and there are eight unknown parameters $R_{e\text{-}array\text{-}A}$, $R_{e\text{-}array\text{-}B}$, $R_{e\text{-}array\text{-}C}$ and $R_{e\text{-}array\text{-}D}$, and $R_{trace\text{-}A}$, $R_{trace\text{-}B}$, $R_{trace\text{-}C}$ and $R_{trace\text{-}D}$. It is impossible to solve these equations for the eight unknown variables from these four equations directly. Additional relationships between these variables are needed to solve for them. Each trace resistance ($R_{trace\text{-}A}$, $R_{trace\text{-}B}$, $R_{trace\text{-}C}$ and $R_{trace\text{-}D}$) depends on the metal film type used, and the geometry of the trace such as the how many rectangular segments the trace has, the film thickness(es) of the segments, the width(s) of the segments, the length(s) of the segment(s). For example, $$R_{trace\text{-}A} = \sum_{i=1}^{N} \rho \frac{L_{A-i}}{t_{A-i} * d_{A-i}} \quad (7)$$

where N is the number of the segments of the trace-A, $t_{A-i}$, $d_{A-i}$ and $L_{A-i}$ is the thickness, width and length of the i-th segment of the traces for the electrode array A, and $\rho$ is the resistivity of the thin film. The equation here applies to the film comprising a single type of metal. The equation can be readily modified to be applicable to the film comprising two or more metal types (e.g. gold film over chromium adhesion layer).

If the film thickness is reasonably uniform (for example, less than 10% in thickness variation) across the substrate, then the relationship among the trace resistances is simply determined by the pre-determined geometrical shapes (e.g. the length, width of the segments). For example, it would be straightforward to calculate the ratio $\alpha_{A-D}$ between the resistance of the electrically conductive traces for the electrode array A to the resistance of the electrically conductive traces for the electrode array D as below, where the film thickness is assumed to be the same everywhere on these traces and the resistivity is also the same everywhere on these traces, $$\alpha_{A-D} = \frac{R_{trace\_A}}{R_{trace\_D}} = \frac{\sum_{i=1}^{N} \rho \frac{L_{A-i}}{t_{A-i} * d_{A-i}}}{\sum_{i=1}^{M} \rho \frac{L_{D-i}}{t_{D-i} * d_{D-i}}} = \frac{\sum_{i=1}^{N} \frac{L_{A-i}}{d_{A-i}}}{\sum_{i=1}^{M} \frac{L_{D-i}}{d_{D-i}}}. \quad (8)$$

Similarly, one can determine the ratio $\alpha_{B-D}$ and $\alpha_{C-D}$ based on the pre-determined geometrical relationships for the traces of the electrode arrays B, C and D. Note that above equations can be similarly derived for the cases where the thin film in these traces comprises more than one metal type. Thus, based on the equalities $$R_{switch\text{-}A} = R_{switch\text{-}B} = R_{switch\text{-}C} = R_{switch\text{-}D} = R_{switch}, \quad (9A)$$

$$R_{trace\text{-}A} = \alpha_{A-D} \cdot R_{trace\text{-}D}, \quad (9B)$$

$$R_{trace\text{-}B} = \alpha_{B-D} \cdot R_{trace\text{-}D}, \quad (9C)$$

and $R_{trace\text{-}C} = \alpha_{C-D} \cdot R_{trace\text{-}D} \quad (9D)$ equations (6A)-(6D) can be re-written in the following format:

$$R_{e\text{-}array\text{-}A} = R_{total\text{-}A} - \alpha_{A-D} \cdot R_{trace\text{-}D} - R_{switch} \quad (10A)$$

$$R_{e\text{-}array\text{-}B} = R_{total\text{-}B} - \alpha_{B-D} \cdot R_{trace\text{-}D} - R_{switch} \quad (10B)$$

$$R_{e\text{-}array\text{-}C} = R_{total\text{-}C} - \alpha_{C-D} \cdot R_{trace\text{-}D} - R_{switch} \quad (10C)$$

$$R_{e\text{-}array\text{-}D} = R_{total\text{-}D} - R_{trace\text{-}D} - R_{switch\text{-}D} \quad (10D)$$

For equations (10A) through (10D), there are five unknown variables, $R_{e\text{-}array\text{-}A}$, $R_{e\text{-}array\text{-}B}$, $R_{e\text{-}array\text{-}C}$, and $R_{e\text{-}array\text{-}D}$ and $R_{trace\text{-}D}$. Mathematically, these unknown variables cannot be determined from these equations. Additional information is needed to solve for these variables $R_{e\text{-}array\text{-}A}$, $R_{e\text{-}array\text{-}B}$, $R_{e\text{-}array\text{-}C}$, and $R_{e\text{-}array\text{-}D}$ and $R_{trace\text{-}D}$.

One approach is invented and described in the present invention. In this approach, same biological or chemical solutions or suspensions are applied to the electrode-arrays A through D. Because the electrode arrays A through D have essentially identical electrode structures, the electrode array resistances $R_{e\text{-}array\text{-}A}$, $R_{e\text{-}array\text{-}B}$, $R_{e\text{-}array\text{-}C}$ and $R_{e\text{-}array\text{-}D}$ should be of same, or very similar value for such a condition when all the electrode arrays are exposed to the same biological or chemical solutions or suspensions, i.e.: $R_{e\text{-}array\text{-}A} \approx R_{e\text{-}array\text{-}B} \approx R_{e\text{-}array\text{-}C} \approx R_{e\text{-}array\text{-}D}$. If we assume the averaged electrode array resistance is $R_{e\text{-}array}$, then these approximate relationship exists $R_{e\text{-}array\text{-}A} \approx R_{e\text{-}array\text{-}B} \approx R_{e\text{-}array\text{-}C} \approx R_{e\text{-}array\text{-}D} \approx R_{e\text{-}array}$. Thus equations (10A-10D) can be changed to the following:

$$R_{e\text{-}array} \approx R_{total\text{-}A} - \alpha_{A\text{-}D} \cdot R_{trace\text{-}D} - R_{switch} \quad (11A)$$

$$R_{e\text{-}array} \approx R_{total\text{-}B} - \alpha_{B\text{-}D} \cdot R_{trace\text{-}D} - R_{switch} \quad (11B)$$

$$R_{e\text{-}array} \approx R_{total\text{-}C} - \alpha_{C\text{-}D} \cdot R_{trace\text{-}D} - R_{switch} \quad (11C)$$

$$R_{e\text{-}array} \approx R_{total\text{-}D} - R_{trace\text{-}D} - R_{switch\text{-}D} \quad (11D)$$

Thus, we would need to find $R_{trace\text{-}D}$ and $R_{e\text{-}array}$ that satisfy the above approximate equality as close as possible. One mathematical approach is to find $R_{trace\text{-}D}$ and $R_{e\text{-}array}$ that would result in the minimum value for the following expression—an expression that quantifies the differences between the two sides of the approximate equality in (11A, 11B, 11C and 11D), $$F(R_{trace\text{-}D}, R_{e\text{-}array}) = [R_{e\text{-}array} - (R_{total\text{-}A} - \alpha_{A\text{-}D} R_{trace\text{-}D} - R_{switch})]^2 + [R_{e\text{-}array} - (R_{total\text{-}B} - \alpha_{B\text{-}D} R_{trace\text{-}D} - R_{switch})]^2 + [R_{e\text{-}array} - (R_{total\text{-}C} - \alpha_{C\text{-}D} R_{trace\text{-}D} - R_{switch})]^2 + [R_{e\text{-}array} - (R_{total\text{-}D} - R_{trace\text{-}D} - R_{switch})]^2 \quad (12)$$

The expression $F(R_{trace\text{-}D}, R_{e\text{-}array})$ is the sum of the squared-differences between the two-sides of the approximate equality in (11A, 11B, 11C and 11D). The smaller $F(R_{trace\text{-}D}, R_{e\text{-}array})$, the closer the two sides of the approximate equality (11A, 11B, 11C and 11D). Thus, values of $R_{trace\text{-}D}$ and $R_{e\text{-}array}$ that result in the minimum value of $F(R_{trace\text{-}D}, R_{e\text{-}array})$ should be determined. Mathematical approach involves in the calculation of the first order derivative of $F(R_{trace\text{-}D}, R_{e\text{-}array})$ to $R_{trace\text{-}D}$ and to $R_{e\text{-}array}$ and let such first order derivatives equal to zero. The values of $R_{trace\text{-}D}$ and $R_{e\text{-}array}$ that result in zero for these first-order-derivatives are those that result in the minimum value of $F(R_{trace\text{-}D}, R_{e\text{-}array})$. The first order derivatives are as follows:

$$\frac{\partial [F(R_{trace\text{-}D}, R_{e\text{-}array})]}{\partial R_{trace\text{-}D}} = \quad (13A)$$

$$2 \cdot \alpha_{A\text{-}D} \cdot [R_{e\text{-}array} - (R_{total\text{-}A} - \alpha_{A\text{-}D} R_{trace\text{-}D} - R_{switch})] +$$
$$2 \cdot \alpha_{B\text{-}D} \cdot [R_{e\text{-}array} - (R_{total\text{-}B} - \alpha_{B\text{-}D} R_{trace\text{-}D} - R_{switch})] +$$
$$2 \cdot \alpha_{C\text{-}D} \cdot [R_{e\text{-}array} - (R_{total\text{-}C} - \alpha_{C\text{-}D} R_{trace\text{-}D} - R_{switch})] +$$
$$2 \cdot [R_{e\text{-}array} - (R_{total\text{-}D} - R_{trace\text{-}D} - R_{switch})] = 0;$$

$$\frac{\partial [F(R_{trace\text{-}D}, R_{e\text{-}array})]}{\partial R_{e\text{-}array}} = \quad (13B)$$

$$2 \cdot [R_{e\text{-}array} - (R_{total\text{-}A} - \alpha_{A\text{-}D} R_{trace\text{-}D} - R_{switch})] +$$
$$2 \cdot [R_{e\text{-}array} - (R_{total\text{-}B} - \alpha_{B\text{-}D} R_{trace\text{-}D} - R_{switch})] +$$
$$2 \cdot [R_{e\text{-}array} - (R_{total\text{-}C} - R_{trace\text{-}D} - R_{switch})] +$$
$$2 \cdot [R_{e\text{-}array} - (R_{total\text{-}D} - R_{trace\text{-}D} - R_{switch})] = 0.$$

Equations (13A) and (13B) can be re-written as $$R_{e\text{-}array} \cdot [\alpha_{A\text{-}D} + \alpha_{B\text{-}D} + \alpha_{C\text{-}D} + 1] + R_{trace\text{-}D} \cdot [\alpha_{A\text{-}D}^2 + \alpha_{B\text{-}D}^2 + \alpha_{C\text{-}D}^2 + 1] = \alpha_{A\text{-}D} \cdot [R_{total\text{-}A} - R_{switch}] + \alpha_{B\text{-}D} \cdot [R_{total\text{-}B} - R_{switch}] + \alpha_{C\text{-}D} \cdot [R_{total\text{-}C} - R_{switch}] + [R_{total\text{-}D} - R_{switch}] \quad (14A)$$

$$4 \cdot R_{e\text{-}array} + R_{trace\text{-}D} \cdot [\alpha_{A\text{-}D} + \alpha_{B\text{-}D} + \alpha_{C\text{-}D} + 1] = [R_{total\text{-}A} - R_{switch}] + [R_{total\text{-}B} - R_{switch}] + [R_{total\text{-}C} - R_{switch}] + [R_{total\text{-}D} - R_{switch}] \quad (14B)$$

Thus, we can solve for $R_{trace\text{-}D}$ as follows:

$$R_{trace\text{-}D} = \frac{4 \cdot S_1 - A_{11} \cdot S_2}{4 \cdot A_{12} - A_{11} \cdot B_{12}} \quad (15)$$

where $A_{11} = [\alpha_{A\text{-}D} + \alpha_{B\text{-}D} + \alpha_{C\text{-}D} + 1]$;

$A_{12} = [\alpha_{A\text{-}D}^2 + \alpha_{B\text{-}D}^2 + \alpha_{C\text{-}D}^2 + 1]$;

$S_1 = \alpha_{A\text{-}D} \cdot [R_{total\text{-}A} - R_{switch}] + \alpha_{B\text{-}D} \cdot [R_{total\text{-}B} - R_{switch}] +$
$\alpha_{C\text{-}D} \cdot [R_{total\text{-}C} - R_{switch}] + [R_{total\text{-}D} - R_{switch}]$;

$B_{12} = [\alpha_{A\text{-}D} + \alpha_{B\text{-}D} + \alpha_{C\text{-}D} 1]$;

$S_2 [R_{total\text{-}A} - R_{switch}] + [R_{total\text{-}B} - R_{switch}] +$
$[R_{total\text{-}C} - R_{switch}] + [R_{total\text{-}D} - R_{switch}]$.

Thus, with the determined $R_{trace\text{-}D}$, the trace resistances of $R_{trace\text{-}A}$, $R_{trace\text{-}B}$, and $R_{trace\text{-}C}$ can be calculated using equations (9B), (9C) and (9D). Furthermore, the electrode array resistance $R_{e\text{-}array\text{-}A}$, $R_{e\text{-}array\text{-}B}$, $R_{e\text{-}array\text{-}C}$ and $R_{e\text{-}array\text{-}D}$ can be calculated from the measured resistance $R_{total\text{-}A}$, $R_{total\text{-}B}$, $R_{total\text{-}C}$ and $R_{total\text{-}D}$ respectively using equations (10A), (10B), (10C) and (10D).

Thus, one aspect of the present invention is directed to a method of calculation of the resistances of the electrical connection traces s from the measured, total resistances for two or more essentially identical electrode arrays (such as, for example arrays A-D in FIG. 1A), comprising the following steps:

(1) exposing the electrode arrays to the solutions having same or similar solutions or suspensions;

(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIG. 1A), and the resistance of the electrode array with the solutions or suspensions present;

(3) solving for the resistances of electrical connection traces using equation (15) and equations (9B), (9C) and (9D), noting in the calculation with equation (15), the geometrical relationships between the electrode arrays are used to determine the factor $\alpha_{A\text{-}D}$, $\alpha_{B\text{-}D}$ and $\alpha_{C\text{-}D}$.

Another aspect of the present invention is directed to a method of calculating the resistance of the electrode arrays from the measured, total electrode resistances for two or more essentially identical electrode arrays (such as, for example arrays A-D in FIG. 1A) if the same or similar solutions or suspensions are added to be in contact with the electrode assays, comprising the following steps:

(1) exposing the electrode arrays to the solutions having same or similar solutions or suspensions;

(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIG. 1A) and the resistance of the electrode arrays with the solutions or suspensions present;

(3) solving for the resistances of electrical connection traces using equation (15) and equations (9B), (9C) and (9D), noting in the calculation with equation (15), the geometrical relationships between the electrode arrays are used to determine the factor $\alpha_{A-D}$, $\alpha_{B-D}$ and $\alpha_{C-D}$;

(4) calculating the resistances of the electrode arrays using equations (10A, 10B, 10C and 10D)).

In many applications, the solutions or suspensions (for example, cell suspension) applied to each electrode array may have different compositions. For example, cell suspensions of different cell numbers may be used so that the suspensions applied to each electrode array are quite different. Under such cases, the determination of the resistance of the electrode arrays with the cells present would require the determination of the resistance of the electrical connection traces by performing a "reference run" or "calibration run" in which the electrode arrays are exposed to a same, reference solution. From the "reference run", the resistances of the electrical connection traces can be determined. In a separate test, the electrode arrays are exposed to the solutions or cell suspensions of interest and the resistances for the electrode arrays under such conditions are measured with an impedance analyzer or impedance measuring circuit. The resistance of the electrode arrays with such cell suspensions present can be determined (or continuously determined) from the measured resistance by subtracting the sum of the resistance of the electronic switches and the resistance of the electrical connection traces for corresponding electrode arrays from the measured resistances.

Thus, another aspect of the present invention is directed to a method of calculating the resistance of the electrode arrays from the total electrical resistances measured at an impedance analyzer for essentially identical electrode arrays (such as electrode arrays A-D in FIG. 1A used as an example) if different solutions or suspensions of interest are applied to the electrode assays, comprising the following steps:

(1) exposing the electrode arrays to the solutions having same or similar solutions or suspensions (reference solutions);

(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIG. 1A) and the resistance of the electrode arrays with the reference solutions present;

(3) solving for the resistances of electrical connection traces using equation (15) and equations (9B), (9C) and (9D), noting in the calculation with equation (15), the geometrical relationships between the electrode arrays of FIG. 1A are used to determine the factor $\alpha_{A-D}$, $\alpha_{B-D}$ and $\alpha_{C-D}$;

(4) applying the solutions or suspensions of interest to each electrode array; and with an impedance analyzer or impedance measurement circuit, measuring the resistance (serial resistance) of each electrode array, such resistance being the sum of the resistance of electronic switches, the resistance of the electrical connection traces between the connection pads and the electrode structures, the resistance of the electrode arrays with the solutions or suspensions of the interest present;

(5) Calculating the resistance of the electrode arrays using equations (10A), (10B), (10C) and (10D) by subtracting the electronic switch resistances and the resistances of electrical connection traces from the measured resistances in the step (4).

Note that in above method, the steps of exposing the electrode arrays to reference solutions for the determination of the resistances of electrically conductive traces (step (1), (2) and (3)) may be performed before or after the steps of applying the solutions or suspensions of interest to the electrode arrays and measuring the total electrical resistance (step (4)). For example, step (4) may be performed first. After that, the solutions or suspensions of the interest may be removed from the electrode array. The reference solutions can then be added to the electrode arrays (step (1)). Step (2) and step (3) can be then performed to determine the resistances of electrical connection traces. Finally, Step (5) can be done.

In another approach, step (1) and (2) can be performed ahead of step (4).

Another aspect of the present invention is directed to a method of determining the resistance of the electrode arrays with the cells present for a cell-based assay based on the total electrical resistance measured at an impedance analyzer for essentially identical electrode arrays. In this method, the electrode arrays are exposed to a same, reference solution (for example, a same cell culture medium that does not contain any cells) and electrical measurement is conducted to determine the resistance of electrical connection traces. With the resistances of the electrical connection traces determined, electrical resistances of the electrode arrays with cell suspensions added to electrode arrays can be calculated from the total electrical resistances measured at an impedance analyzer. Such total electrical resistance would include the resistance of the electrode arrays with cells present, the resistance of electronic switches and the resistance of electrical connection traces. The method comprises following steps:

(1) exposing the electrode arrays to the solutions having same or similar solutions or suspensions (reference solutions);

(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIG. 1A) and the resistance of the electrode arrays with the reference solutions present;

(3) solving for the resistances of electrical connection traces using equation (15) and equations (9B), (9C) and (9D), noting in the calculation with equation (15), the geometrical relationships between the electrode arrays in FIG. 1A are used to determine the factor $\alpha_{A-D}$, $\alpha_{B-D}$ and $\alpha_{C-D}$;

(4) applying the cell suspensions of interest to each electrode array; and with an impedance analyzer or impedance measurement circuit, measuring the resistance (serial resistance) of each electrode array, such resistance being the sum of the resistance of electronic switches, the resistance of the electrical connection traces between the connection pads and the electrode structures, the resistance of the electrode arrays with the cell suspensions of the interest present, (5) Calculating the resistance of the electrode arrays using equations (10A), (10B), (10C) and (10D) by subtracting the electronic switch resistances and the resistances of electrical connection traces from the measured resistances in step (4).

Note that in above method, the steps of exposing the electrode arrays to reference solution for the determination of the electrical resistance of electrically conductive traces (step (1), (2) and (3)) may be performed before or after the steps of applying the solutions of interest or cell suspensions of interest to the electrode arrays and measuring the total electrical resistance (step (4)). For example, step (4) may be performed first, followed by steps (1) and (2). In one approach, after step (4), the cell suspensions of the interest may be removed from the electrode array. Then reference solutions can be added to the electrode arrays. In another approach, after step (4), the cells are all lysed with some cell lysis solutions so that the electrodes are exposed to the same, reference solutions for the measurement and calculation of step (2) and (3). And then, step (5) is performed to determine the electrical resistance of electrode arrays with the cell suspensions of interest present.

The determination of the resistances of the electrical conductive traces for the electrode arrays that essentially identical electrode arrays may be, or may not be, part of the monitoring of cell-substrate impedance for cell-based assays. It depends on how the impedance data (measured at a single frequency or multiple frequencies, measured at multiple time points) of the electrode arrays is analyzed.

In some assays, one is interested in the relative change in the resistance or impedance of the electrode arrays with the cells present relative to the baseline resistance or impedance. For such cases, it is preferred to determine the resistance (or impedance) of the electrode arrays from the total, measures resistance (or impedance) by subtracting the resistance of the electrical conductive traces and the resistance of electronic switches. Thus, determination of the resistances or impedance of the electrically conductive traces may be required.

In some other assays, one is interested in the absolute changes in the resistance (or impedance) of the electrode arrays with cells present relative to the baseline resistance (or impedance). In these cases, one can directly subtract the measured resistance or impedance for the baseline condition from the measured resistance or impedance for the condition that the cells are present on the electrode arrays. The contribution of the resistance (or impedance) of the electronic switches and the resistance (or impedance) of the electrically conductive traces to the total measured resistance (or impedance) values is cancelled out in such subtractions. Thus, there is no need for determining the resistances of the electrically conductive traces.

In some assays, one is interested in calculating the Cell Index or Cell Number Index based on the monitored impedance values. Depending on which method is used for calculating the Cell Index, it may, or may not, be necessary to determine the resistances of the electrically conductive traces. For example, for the Cell Index calculation method (A) described above, the resistances of the electrically conductive traces are needed, in order to remove the effect of the resistance of the electrically conductive traces on the analysis of the relative change of the resistance or impedance. In another example, for the Cell Index calculation method (F) described above, there is no need to determine the resistances of the electrically conductive traces since the effect of the resistance of the electrically conductive traces is canceled out in the calculations.

The monitoring of the cell-substrate impedance may be or may not be based on the change with respect to the baseline impedance (or resistance). For example, a cell-based assay is performed to assess the effect of a test compound on the cells. One method in performing such an assay is by monitoring of the cell-substrate impedance and determining the change in the cell-substrate impedance before and after the addition of the test compound to the cells. The monitoring of cell-substrate impedance can be performed at a single frequency point or multiple frequency points, at a single time point or multiple time points after drug addition. For example, the impedance is first measured at a single frequency or multiple frequencies for the electrode arrays with the cells present just before addition of test compound. The test compound is then added to the cells. The impedance is then measured again at the same single frequency or multiple frequencies for the electrode arrays with the cells after the addition of test compound. Such post-compound addition measurement may be performed for many time points continuously in a regular or irregular time intervals. The change in the cell-substrate impedances can be determined or quantified by subtracting the impedance(s) (resistance and/or reactance) measured before addition of the test compound from the impedance(s) (resistance and/or reactance) measured after the addition of the test compound. If the measurement is done at multiple frequencies, a single parameter or multiple parameters may be further derived for each time point after compound addition based on the calculated change in the cell-substrate impedances. Such parameters are used to quantify the cell changes after compound addition. Such approaches can be used further to analyze the responses of the cells to a test compound at multiple concentrations to derive dose-dependent response curves.

D. Methods for Performing Real-Time Cell-Based Assays

The present invention provide cell-based assays that can be performed in real time to assess cell proliferation, cell growth, cell death, cell morphology, cell membrane properties (for example, size, morphology, or composition of the cell membrane) cell adhesion, and cell motility. Thus the assays can be cytotoxicity assays, proliferation assays, apoptosis assays, cell adhesion assays, cell activation assays, anti-cancer compound efficacy assays, receptor-ligand binding and signal transduction analysis, assays of cytoskeletal changes, assays of cell structural changes (including but not limited to, changes in cell membrane size, morphology, or composition), assays of cell differentiation or de-differentiation, assays of cell adhesivity, assays of cell-cell interactions, analysis of microbial and environmental toxins, etc. The assays are real-time assays in the sense that cell behavior or cell condition being assayed can be assessed continuously at regular or irregular intervals. Depending on the applications, cell behaviors, cell responses, or cell conditions being assayed can be within seconds to minutes of their occurrence. The cell response during an assay can be monitored essentially continuously over a selected time period. For example, a culture can be monitored every five to fifteen minutes for several hours to several days after addition of a reagent. The interval between impedance monitoring, whether impedance monitoring is performed at regular or irregular intervals, and the duration of the impedance monitoring assay can be determined by the experimenter.

Thus, the cell-based impedance assays of the present invention avoid inadvertently biased or misleading evaluation of cell responses due to the time point or time points chosen for sampling or assaying the cells. In addition, the assays do not require sampling of cell cultures or addition of reagents and thus eliminate the inconvenience, delay in obtaining results, and error introduced by many assays.

Descriptions of cell-substrate monitoring and associated devices, systems and methods of use have been provided in U.S. provisional application No. 60/379,749, filed on Jul. 20, 2002; U.S. provisional application No. 60/435,400, filed on Dec. 20, 2002; U.S. Provisional application 60/469,572, filed on May 9, 2003, PCT application number PCT/US03/22557, entitled "Impedance based devices and methods for use in assays", filed on Jul. 18, 2003; PCT application number PCT/US03/22537, entitled "Impedance based apparatuses and methods for analyzing cells and particles", filed on Jul. 18, 2003; U.S. patent application Ser. No. 10/705,447, entitled "Impedance based devices and methods for use in assays", filed on Nov. 10, 2003; U.S. patent application Ser. No. 10/705,615, entitled "Impedance based apparatuses and methods for analyzing cells and particles", filed on Nov. 10, 2003, all incorporated herein by reference for their disclosure of cell-substrate impedance devices, systems, and methods of use. Additional details of cell-substrate impedance monitoring technology is further disclosed in the present invention.

In brief, for measurement of cell-substrate or cell-electrode impedance using the technology of the present invention, cell-substrate impedance monitoring devices are used that have microelectrode arrays with appropriate geometries fabricated onto the bottom surfaces of wells such as microtiter plate wells, or have a similar design of having multiple fluid receptacles (wells) having electrodes fabricated on their bottom surfaces facing into the wells. Cells are introduced into the wells of the devices, and make contact with and attach to the electrode surfaces. The presence, absence or change of properties of cells affects the electronic and ionic passage on the electrode sensor surfaces.

Measuring the impedance between or among electrodes provides important information about biological status of cells present on the sensors. When there are changes to the biological status of the cells analogue electronic readout signals can be measured automatically and in real time, and can be converted to digital signals for processing and for analysis. In a system of the present invention, a cell index can be automatically derived and provided based on measured electrode impedance values. The cell index obtained for a given well reflects: 1) how many cells are attached to the electrode surfaces in this well, 2) how well (tightly or extensively) cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index.

In one aspect of the present invention, a method is provided for performing cell-based assays, comprising: a) providing a cell-substrate impedance monitoring system of the present invention; b) introducing cells into one or more wells of a device of the system, wherein at least one of the one or more wells comprises an electrode array; and d) monitoring cell-substrate impedance of at least one of the wells that comprise an electrode array and cells.

The method can be used to assay cell status, where cell status includes, not limited to, cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. The cell-based assays that be performed with above methods include, but are not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

In preferred embodiments of this aspect of the present invention, cells are added to at least two wells of a device, each of which comprises an electrode array, and impedance is monitored from at least two wells that comprise cells and an electrode array.

The cells used in the assay can be primary cells isolated from any species or cells of cell lines. The cells can be engineered cells. In some embodiments, different cell types are added to different wells and the behavior of the cells is compared.

Impedance can be monitored at regular or irregular time intervals. Preferably, impedance is monitored at three or more time points, although this is not a requirement of the present invention. In one embodiment of the above cell-based assay, the cell-substrate impedance is monitored at regular time intervals. Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

Figure 7:
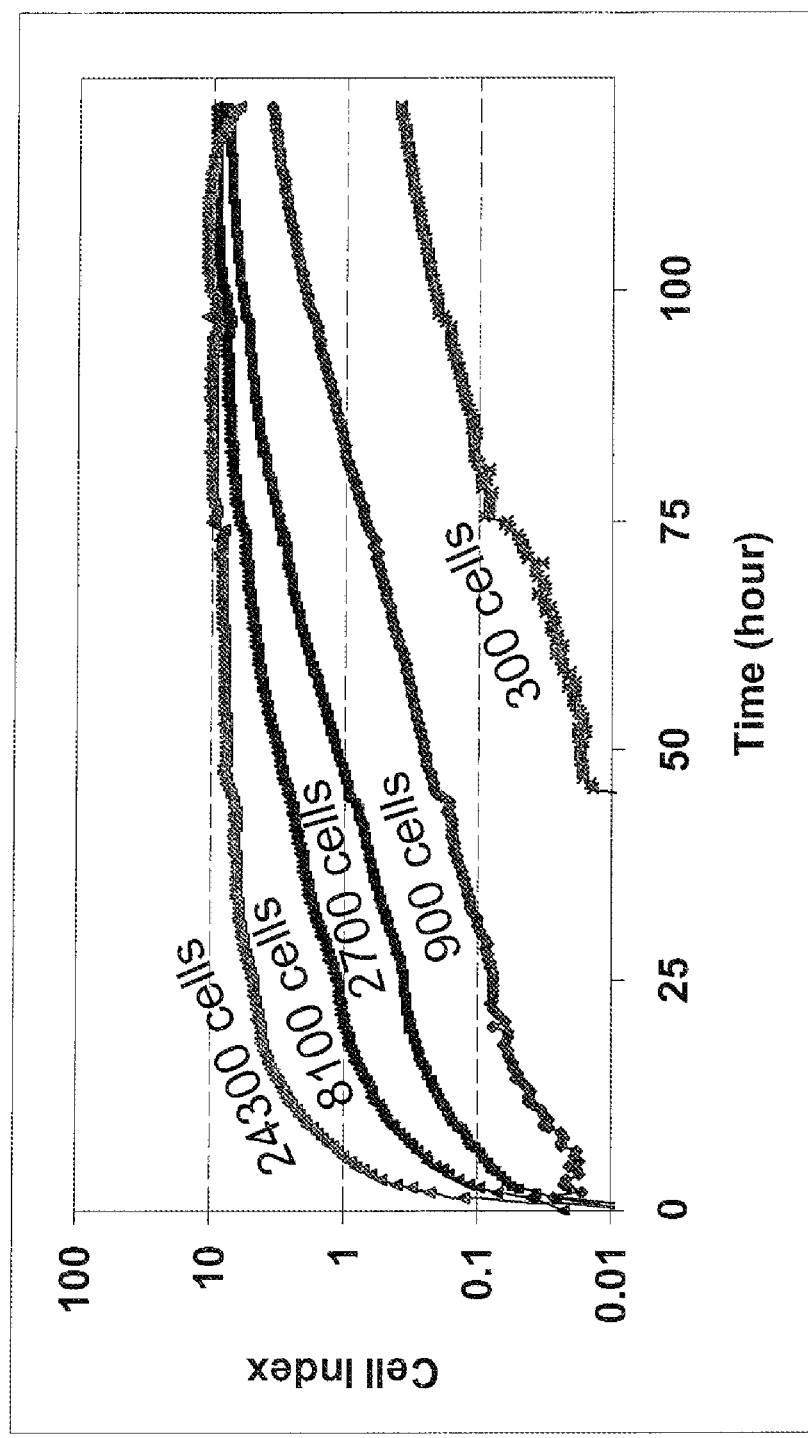
FIG. 7 shows real-time monitoring of proliferation of H460 cells seeded at different initial cell seeding numbers on a cell substrate monitoring system of the present invention. Cell proliferation was continuously recorded every 15 minutes for over 125 hours. The cell growth curves in the log scale show exponential cell growth or cells in the stationary phase.

FIG. 7 depicts results of the use of methods of the present invention to monitor cell proliferation. In this experiment, H460 cells were introduced into wells of a 16 well device of a cell-substrate impedance monitoring system of the present invention, with different wells receiving different initial cell seeding numbers. The device was engaged with a device station of the system that was in a tissue culture incubator that kept a temperature of 37 degrees C. and an atmosphere of 5% $CO_2$. Cell-substrate impedance was monitored at 15 minute intervals for 125 hours. The cell index was calculated by the system for each time point and displayed as a function of time to give cell growth (proliferation) curves for each cell seeding number. The cell growth curves were plotted on a log scale showing exponential growth phases and stationary phases.

Figure 8:
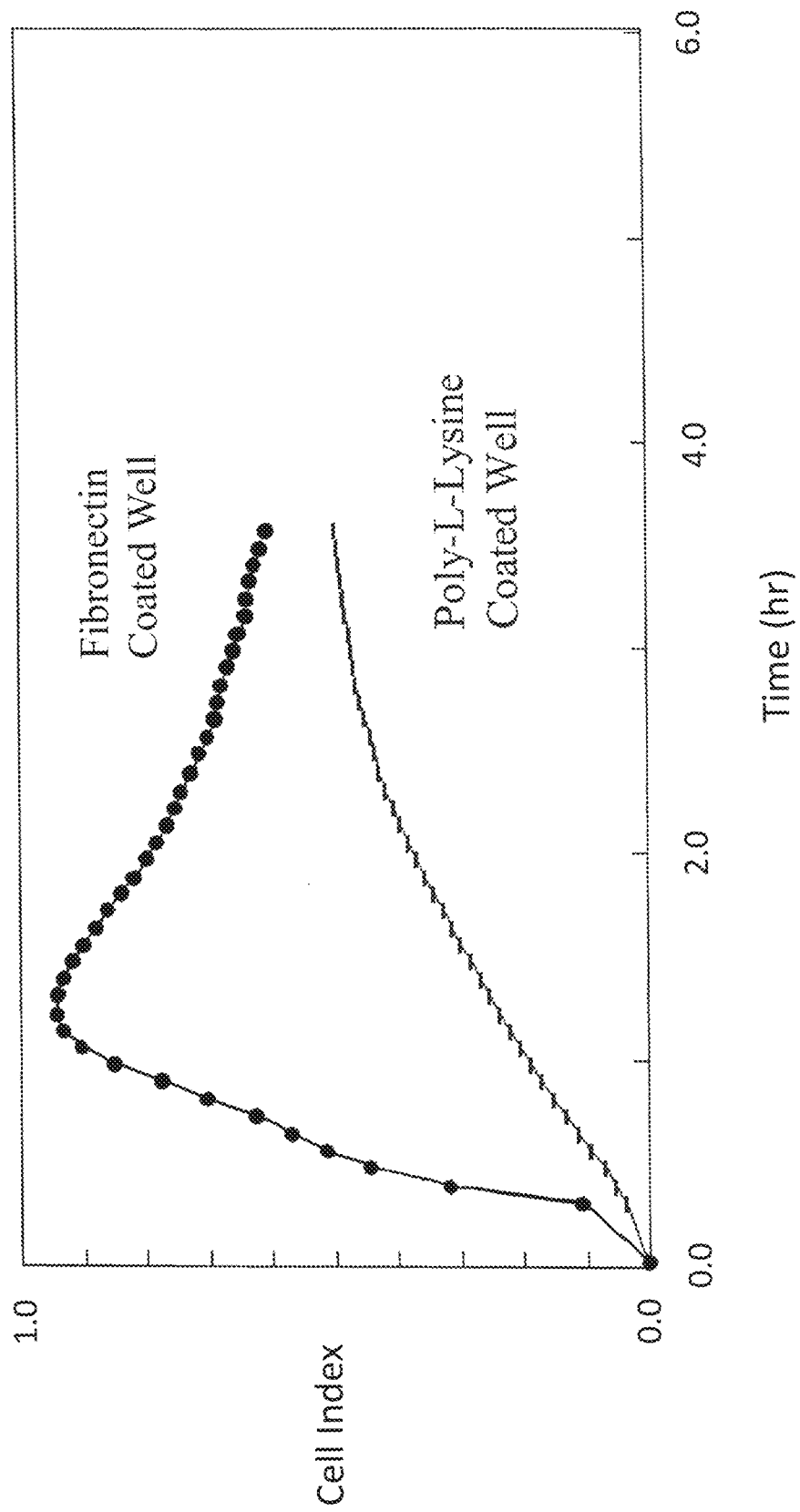
FIG. 8 shows real time monitoring of cell attachment and spreading of NIH3T3 cells using a cell-substrate impedance monitoring system of the present invention. The cells were seeded onto devices coated with either poly-L-lysine or fibronectin. The cell attachment and cell spreading processes on the different coating surfaces were monitored every 3 minutes for over 3 hours in real time.

FIG. 8 depicts results of real-time monitoring of cell attachment and spreading of NIH3T3 cells. The cells were seeded onto cell-substrate impedance monitoring devices of the present invention that were coated with either poly-L-lysine or fibronectin. The device was engaged with a device station that was in a tissue culture incubator that kept a temperature of 37 degrees C. and an atmosphere of 5% $CO_2$. Cell attachment and cell spreading on the difference coating surfaces were monitored by measuring impedance on the cell-substrate monitoring system. Impedance was monitored in real time every 3 minutes for 3 hours. The cell index for each time point was calculated by the impedance monitoring system and plotted as a function of time.

Figure 9:
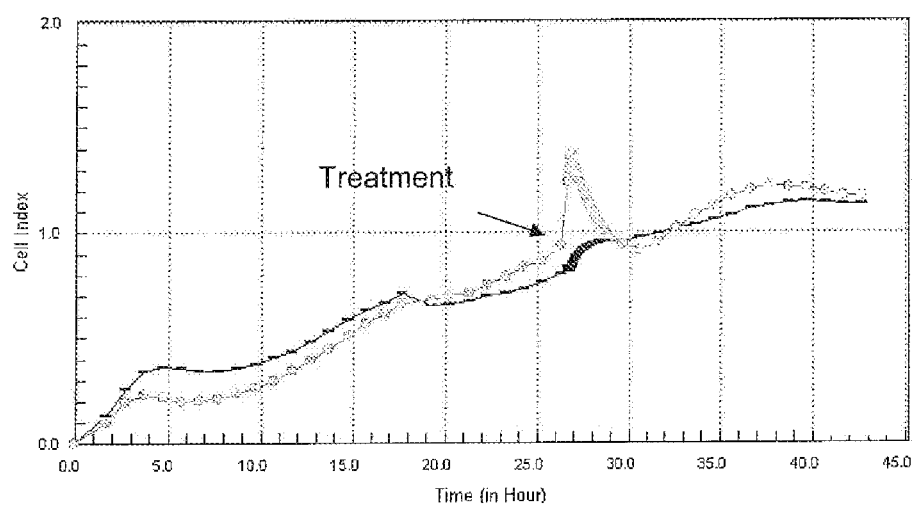
FIG. 9 shows real-time monitoring of morphological changes in Cos-7 cells using a cell-substrate impedance monitoring system of the present invention. The cells were serum starved for 8 hours and stimulated with or 50 ng/mL EGF. Changes in cell morphology were monitored at 3 min intervals for 2 hours and then 1 hour interval for 14 hours. The initial jump in the signal in EGF-treated cells is due to membrane ruffling and actin dynamics in response to EGF. The arrow indicates the point of EGF stimulation.

FIG. 9 shows the results of an experiment monitoring morphological changes in Cos-7 cells in response to stimulation with epidermal growth factor (EGF). Cells were seeded in wells of a 16 well monitoring device of the present invention that engaged a device station of a cell-substrate monitoring system. The device station was positioned in an incubator held at 37 degrees C. and 5% $CO_2$. The cells were serum starved for 8 hours and then stimulated with 50 nanograms/mL of EGF. Control cells did not receive EGF. Impedance was monitored at 3 minute intervals for 2 hours and then at 1 hour intervals for 14 hours. The cell index was calculated by the system and plotted as a function of time. An initial jump in cell index is seen in EGF-treated cells due to membrane ruffling and actin dynamics in response to EGF. The arrow indicated the point of EGF addition.

D.1. Cell-Based Assays to Test the Effects of Compounds on Cells

In yet another aspect, the present invention provides a method for performing a cell-based assay investigating the effect of one or more test compounds on cells, comprising: a) providing a cell-substrate impedance monitoring system of the present invention; b) introducing cells into at least one of the well of the device that comprises an electrode array; c) adding at least one test compound to one or more of the wells comprising cells and an electrode array; and d) monitoring cell-substrate impedance of the one or more wells before and after adding the compound, in which changes in impedance can provide information about cell responses to the one or more compounds.

Information about cell responses to the one or more compounds includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance. The cell-based assays that be performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

The cells used in the assay can be primary cells isolated from any species or can be cells of cell lines. The cells can be genetically engineered cells (For example, cells from a genetically modified organism, such as for example from a "gene knockout" organism, or cells that have been engineered to overexpress an endogenous gene or a transgene, or cells whose normal gene expression has been manipulated by use of antisense molecules or silencing RNA.) In some embodiments, different cell types are added to different wells and the behavior of the different cell types in response to one or more compounds is compared.

A test compound can be any compound, including a small molecule, a large molecule, a molecular complex, an organic molecule, an inorganic molecule, a biomolecule such as but not limited to a lipid, a steroid, a carbohydrate, a fatty acid, an amino acid, a peptide, a protein, a nucleic acid, or any combination of these. A test compound can be a synthetic compound, a naturally occurring compound, a derivative of a naturally-occurring compound, etc.

In preferred methods of the present invention, cells are added to at least two wells of the cell-substrate impedance monitoring device that comprise an electrode array, and at least one well that comprises an electrode array and comprises cells does not receive a test compound. A control well that does not receive a test compound can be monitored, and its impedance data can be compared with that of wells that do receive compound to determine the effect of the one or more test compounds on cells.

Impedance can be monitored at regular or irregular time intervals. Preferably, impedance is monitored at three or more time points, at least one of which is prior to the addition of one or more test compounds. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

Preferably, data from impedance monitoring of a well that comprises cells and a test compound is compared with data from impedance monitoring of a well that comprises cells in the absence of a test compound, however, this is not a requirement of the present invention. For example, it is also possible to compare impedance measurements from one or more time points prior to the addition of compound to compare impedance measurements from one or more time points after the addition of compound. Such comparisons can be used directly to assess the cells' response to a compound. It is also possible to calculate a cell index (or cell number index) using the impedance values obtained. Methods of calculating a cell index (cell number index) are disclosed herein as well as in parent application U.S. patent application Ser. No. 10/705,447, herein incorporated by reference for disclosures relating to cell number index and its calculation. The cell index calculated from impedance measurements of wells receiving compound can be compared with the cell index calculated from impedance measurements of control wells to assess the effect of a compound on cells. Alternatively, cell index calculated from impedance measurements of wells from one or more time points after the addition of a compound can be compared with the cell index calculated from impedance measurements of wells from one or more time points prior to the addition of a compound to assess the effect of a compound on cells. In some preferred embodiments, the cell index can be used as an indicator of cytotoxicity.

The present invention includes assays in which different concentrations of a compound are added to wells of a device. The method includes: a) providing a cell-substrate impedance monitoring system of the present invention; b) introducing cells into at least two wells of the device that each comprise an electrode array; c) adding to at least one well of the device comprising cells and an electrode array a first concentration of a test compound; d) adding to at least one other well of the device comprising cells and an electrode array a second concentration of a test compound; and e) monitoring cell-substrate impedance of the two or more wells before and after adding the compound, in which changes in impedance can provide information about cell responses to the compound.

Information about cell responses to the compound includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance. The cell-based assays that be performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

The cells and test compound used in the assay can be as described above for assays testing effects of test compounds. In preferred methods of the present invention, cells are introduced into at least three wells of the device that each comprise an electrode array, and at least one well that comprises an electrode array and comprises cells does not receive test compound. A control well that does not receive a test compound can be monitored, and its impedance data can be compared with that of wells that do receive compound to determine the effect of the one or more test compounds on cells.

Impedance monitoring can be as described immediately above for assays testing effects of test compounds.

Preferably, data from impedance monitoring of wells that comprise cells and different concentrations of test compounds are compared. Such comparisons can be used directly to assess the cells' response to increasing concentrations of a compound. It is also possible to calculate a cell index (or cell number index) using the impedance values obtained. Methods of calculating a cell index (cell number index) are disclosed herein as well as in parent application U.S. application Ser. No. 10/705,447, herein incorporated by reference for disclosure of cell index number and method of calculating cell index number. In some preferred embodiments, the cell index can be used as an indicator of cytotoxicity.

The cell index calculated from impedance measurements of wells receiving different concentrations of compound can be compared to assess the effect of a compound on cells. Alternatively, cell index calculated from impedance measurements of wells comprising different concentrations of a compound can be compared. Dose response relationships can be derived from such comparisons. In some preferred embodiments, time dependent IC50 values may be calculated from cell index values for compounds that exhibit cytotoxicity or inhibit particular cell responses.

In one embodiment of the method, analyzing the cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

Cell-Based Assays with More Than One Compound

In yet another aspect, the present invention provides a method for performing a cell-based assay investigating the effect of two or more test compounds on cells. The method includes: a) providing a cell-substrate impedance monitoring system of the present invention; b) introducing cells into at least two wells of the device that each comprise an electrode array; c) adding to at least one well of the device comprising cells and an electrode array a first test compound; d) adding to at least one other well of the device comprising cells and an electrode array a second test compound; and e) monitoring cell-substrate impedance of at least one well comprising cells and a first compound and at least one well comprising cells and a second compound, in which changes in impedance can provide information about cell responses to the first and second compounds.

Preferably, time-dependent responses of cells to the first compound and the second compound are compared to see how similar or different the responses from the two compounds are. In one preferred embodiment of this method, time-dependent cytotoxic responses are compared.

The cells and test compound used in the assay can be as described above for assays testing effects of test compounds. In preferred methods of the present invention, cells are introduced into at least three wells of the device that each comprise an electrode array, and at least one well that comprises an electrode array and comprises cells does not receive a test compound. A control well that does not receive a test compound can be monitored, and its impedance data can be compared with that of wells that receive a compound to determine the effect of the test compounds on cells.

Impedance monitoring can be as described immediately above for assays testing effects of test compounds.

Preferably, data from impedance monitoring of wells that comprise different test compounds are compared. In one preferred embodiment impedance monitoring is performed for the first compound at multiple dose concentrations. In another embodiment, time-dependent cellular responses are determined for the second compound at multiple dose concentrations. In yet another embodiment, time-dependent cellular responses are determined for both first compound and second compound at multiple dose concentrations.

In another embodiment of above method, the first compound is a compound with a known mechanism for its cytotoxic effect and the second compound is a compound with an unknown mechanism for its cytotoxic effect. If the time dependent cytotoxic responses from the second compound are similar to that of the first one, the second compound may follow a similar mechanism for its cytotoxic effect to the first compound.

Various approaches may be used in comparing the cytotoxic responses of the compounds. A cell index (or cell number index) can optionally be calculated using the impedance values obtained. In one embodiment of the method described above, time dependent IC50 may be derived for the compounds and comparison between their cytotoxic responses is done by comparing their time dependent IC50 curves based on cell index values. If the IC50 curves follow a similar time-dependent trend, the two compounds may follow a similar mechanism for inducing cytotoxicity effects. In another embodiment of the method described, direct comparison of time-dependent cytotoxic responses of two compounds are done where the concentrations for the two compounds may be the same or may be different. Direct comparison between time-dependent cytotoxic responses may be done by analyzing the slope of change in the measured responses (that is equivalent to the first order derivative of the response with respect to time) and comparing the time-dependent slopes for the two compounds. In another approach, the time-dependent cytotoxic responses may be analyzed for their higher order derivatives with respect to time. Comparing such high order derivatives may provide additional information as for the mechanisms of compound-induced cytotoxicity.

Cell-Based Assays with More Than One Cell Type

In yet another aspect, the present invention provides a method for cytotoxicity profiling for a compound on multiple cell types, comprising: a) providing a cell-substrate impedance monitoring system of the present invention; b) introducing a first type of cells into at least one well of the device that comprises an electrode array; c) introducing a second type of cells into at least one other well of the device that comprises an electrode array; d) adding a test compound to at least one well comprising cells of a first type and to at least one well comprising cells of a second type; and e) monitoring cell-substrate impedance of at least one well comprising cells of a first type and test compound and of at least one well comprising cells of a second type and test compound, in which changes in impedance can provide information about cell responses to the first and second compounds.

Preferably, time-dependent responses of the first and second types of cells are compared to see how similar or different the responses from the two types of cells are. In one preferred embodiment of this method, time-dependent cytotoxic responses are compared.

The cell types used in the assay can be primary cells isolated from any species or can be cells of cell lines. In some preferred embodiments, the different cell types are the same type of cell from different individuals, and thus have different genotypes. One or more of the cell types can be genetically engineered (For example, cells from a genetically modified organism, such as for example from a "gene knockout" organism, or cells that have been engineered to overexpress an endogenous gene or a transgene, or cells whose normal gene expression has been manipulated by use of antisense molecules or silencing RNA.) In these cases, genetically modified cells can be compared with control cells. In some embodiments, three or more different cell types are added to different wells and the behavior of the three or more different cell types in response to one or more compounds is compared.

The test compound or compounds used in the assay can be as described above for assays testing effects of test compounds. In preferred methods of the present invention, cells are introduced into at least three wells of the device that each comprise an electrode array, and at least one well that comprises an electrode array and comprises cells does not receive a test compound. A control well that does not receive a test compound can be monitored, and its impedance data can be compared with that of wells that receive a compound to determine the effect of the test compounds on cells. In preferred embodiments of the present invention, for each cell type tested there is a control performed in which the control does not receive test compound.

Impedance monitoring can be as described immediately above for assays testing effects of test compounds.

Preferably, data from impedance monitoring of wells that comprise different cell types are compared. In one preferred embodiment impedance monitoring is performed for different cell types exposed to multiple dose concentrations of a compound. In some embodiments, multiple compounds can be tested with multiple cell types. In some embodiments, multiple compounds at multiple concentrations can be tested with multiple cell types.

In one embodiment of the method, analyzing real-time cytotoxicity response may include the derivation of time-dependent IC50 values for the compound on the multiple cell types. In another embodiment of the method, analyzing real-time cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

In one embodiment of the method, analyzing real-time cytotoxicity responses may include the derivation of time-dependent IC50 values for the compound on the multiple cell types. In yet another embodiment, the above methods are applied to perform cytotoxicity profiling of multiple compounds on multiple cell types.

In another embodiment of the method, analyzing real-time cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

Some examples of compound assays that can be performed using a cell-substrate impedance system of the present invention are provided by way of illustration with reference to the figures. In these examples, cell index is calculated using the same method as the Cell Index calculation method (A) as described in Section C of the present application. In some of the figures of the present application, Normalized Cell Index was plotted. The Normalized Cell Index at a given time point is calculated by dividing the Cell Index at the time point by the Cell Index at a reference time point. Thus, the Normalized Cell Index is 1 at the reference time point.

As described in the present application, if the cell attachment conditions remain unchanged or exhibit little change over the course of an assay that uses impedance monitoring, then the larger the cell index, the larger the number of the cells in the wells. A decrease in cell index suggests that some cells are detaching from the substrate surface or dying under the influence of the compound. An increase in cell index suggests that more cells are attaching to the substrate surfaces, indicating an increase in overall cell number.

Figure 10:
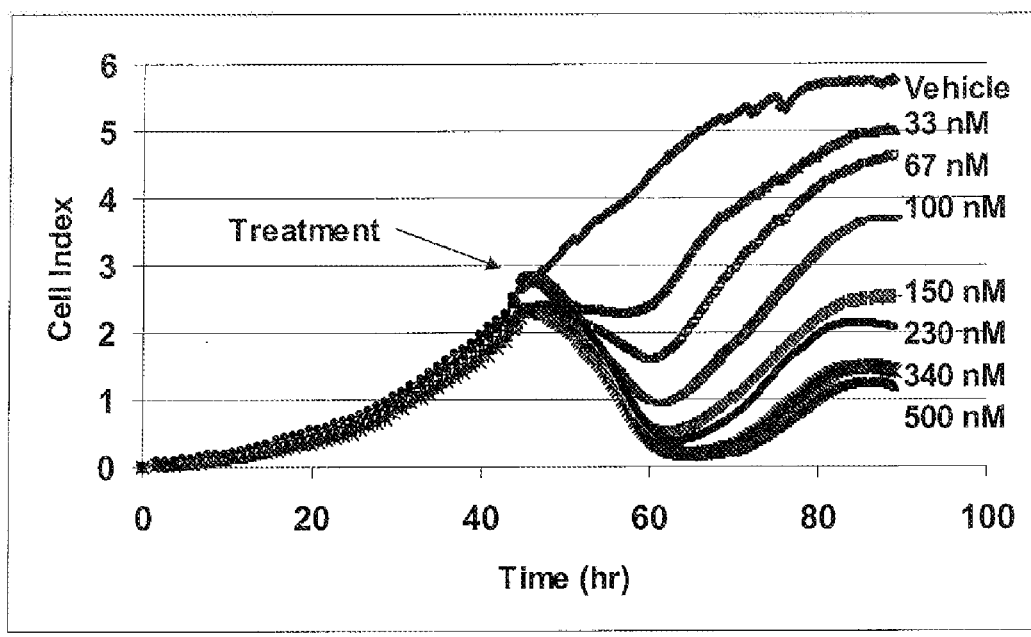
FIG. 10 shows a plots of time-dependent cell index for H460 cells treated by anticancer drug paclitaxel. Different wells of cultured H460 cells in their exponential growth phase were treated with different concentrations of Paclitaxel. The dynamic response of the cells to different doses of paclitaxel was monitored in real time every 15 minutes for 50 hours after treatment using a cell-substrate impedance monitoring system of the present invention.

FIG. 10 shows curves that represent the time-dependent cell index for H460 cells treated with different concentrations of the anticancer drug paclitaxel. In this experiment, H460 cells were introduced into wells of a 16× cell-substrate impedance monitoring device. The device was positioned on a device station that was located in an incubator maintaining conditions of 37 degrees C. and 5% $CO_2$. The cells were cultured and treated at their exponential growth phase with different concentrations of paclitaxel. The dynamic response of the cells to different doses of paclitaxel was monitored by monitoring cell-substrate impedance in real time every 15 minutes for 50 hours after treatment using a cell-substrate impedance monitoring system. The cell-substrate impedance monitoring system calculated the cell index at each time point monitored and plotted the cell index as a function of time. For paclitaxel concentrations between 67 nanomolar and 500 nanomolar, H460 cells exhibited a gradual decrease in cell index after compound addition. However, the cell index reached a minimum at a time dependent on the compound concentration, between about 15 hours and 20 hours after compound addition. After that point, there was a gradual increase in cell index in these wells. The cell index for compound concentration of 33 nanomolar exhibited a near-constant value for up to about 15 hours after compound addition. After 15 hours following compound addition, the cell index exhibited a gradual increase.

Figure 11:
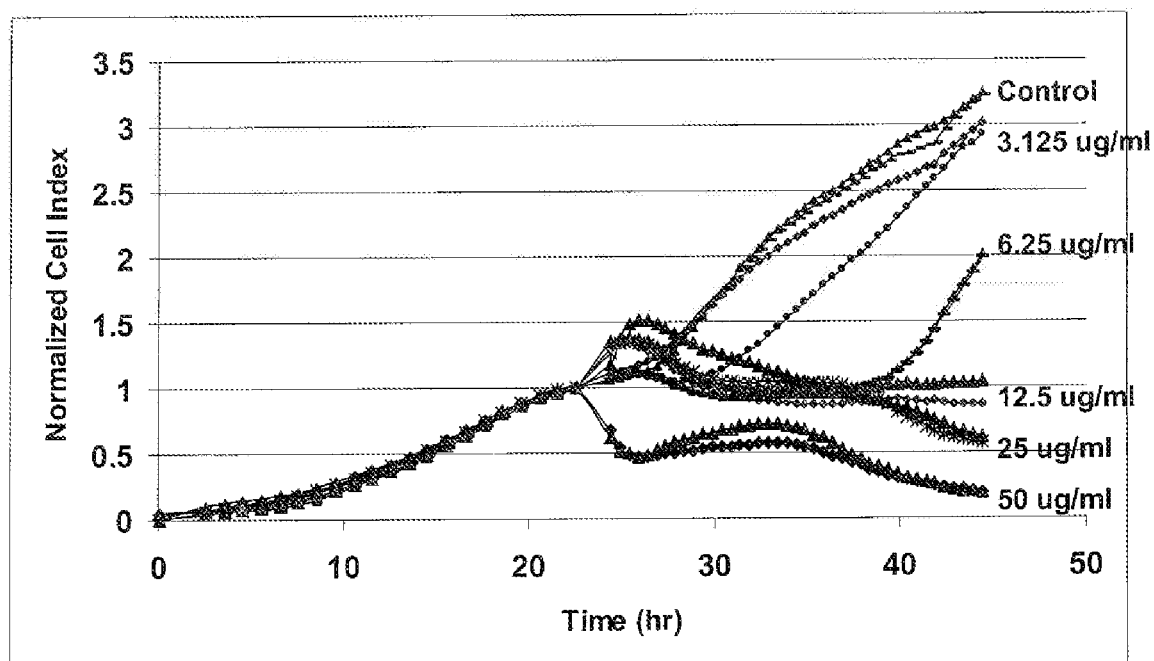
FIG. 11 shows plots of time-dependent cell index for H460 cells treated by anticancer drug AC101103. Different wells of cultured H460 cells were treated at their exponential growth phase with different concentrations of AC101103. The dynamic response of the cells to different doses of AC101103 was monitored in real time every 30 minutes for about 20 hours after treatment on a cell-substrate impedance monitoring system of the present invention.

FIG. 11 shows curves that represent the time-dependent cell index for H460 cells treated with anticancer drug AC101103. H460 cells were introduced into wells of a 16× cell-substrate impedance monitoring device. The device was positioned on a device station that was located in an incubator maintaining conditions of 37 degrees C. and 5% $CO_2$. The cells were cultured and treated at their exponential growth phase with different concentrations of AC101103. The dynamic response of the cells to different doses of AC101103 was monitored by measuring impedance in real time every 30 minutes for about 20 hours after treatment on the cell-substrate monitoring system.

Notably, the time-dependent cell index in FIG. 11 is significantly different from those shown in FIG. 10. For compound concentrations at 3.125 microgram/ml, 6.25 microgram/ml and 12.5 microgram/ml, the cell index exhibited a near-constant value for about 5 hrs, about 15 hrs and >20 hrs respectively. For compound concentrations at 3.125 microgram/ml and 6.25 microgram/ml, the cell index started to increase after about 5 hrs and about 15 hrs following compound addition. For the compound concentration of 25 microgram/ml, there was a gradual, yet slow decrease in the cell index after compound addition. For the compound concentration of 50 microgram/ml, there was an about 10 hr time period over which the cell index remained near-constant, and after that, the cell index decreased steadily.

Figure 12:
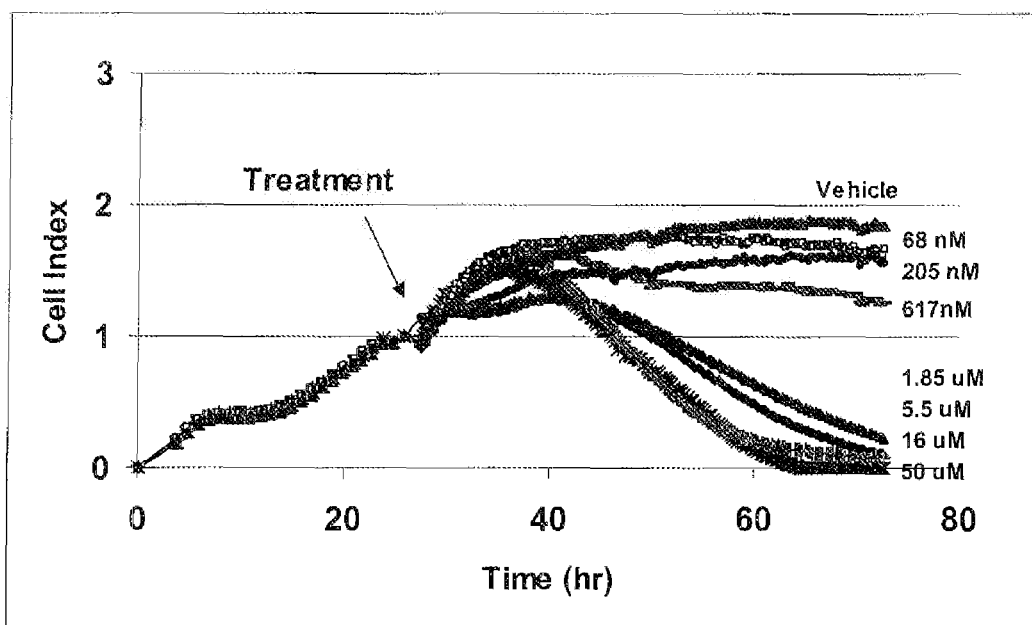
FIG. 12 shows dynamic drug response curves of A549 cells treated with doxorubicin. 10,000 A549 cells were seeded in each well of a 16× cell-substrate impedance monitoring device. Cell attachment and cell growth were monitored using a cell-substrate impedance monitoring system before treatment. When the cells were in exponential growth phase, doxorubicin at different concentration was added to the cells. The time and drug dose dependent cell response to doxorubicin was recorded in real time on the as shown in this figure.

FIG. 12 shows dynamic drug response curves of A549 cells treated with doxorubicin. 10,000 A549 cells were seeded into each well of a 16× device. The device was positioned on a device station that was located in an incubator maintaining conditions of 37 degrees C. and 5% $CO_2$. Cell attachment and cell growth were monitored on a cell-substrate impedance system in real time before treatment by monitoring impedance at regular intervals. When the cells were in exponential growth phase, doxorubicin at different concentrations was added to the wells. The same volume of the solvent used to dissolve the drug was added to some wells as a control. The time, and drug dose dependent cell response (calculated as cell index) to doxorubicin was recorded in real time on the cell-substrate impedance monitoring system as shown in this figure.

E. Cell-Substrate Impedance Assays to Monitor IgE-Mediated Cell Activation

The present invention also includes methods of monitoring cell-substrate impedance of cells stimulated by IgE. The method is based on quantifying in real time the cytoskeletal changes that result from antigen binding to the IgE-Fc (epsilon)RI complex on the surface of responsive cells, such as, but not limited to, mast cells. The electronic assays provided rely on cytoskeletal dynamics that are an intrinsic mast cell response to antigen and an essential part of the mast cell activation program, and precludes the need for establishing reporter cell lines or using other assay reagents. Furthermore, since the assay is performed in real time, both antigen-dependent and antigen-independent response to IgE-mediated activation of mast cells can be monitored in the same assay.

The assays described herein that monitor cell-substrate impedance of cells stimulated by IgE can use any cell-substrate impedance measuring device, including but not limited to those described in parent U.S. patent application Ser. No. 10/705,447 and herein. A cell-substrate impedance device useful in the methods of the present invention refers to any device that has a surface suitable for cells and has electrodes that cells can settle on and interact with. The measurement on the electrode impedance can reflect the cell status such as cell number, cell morphology, or cell adhesion. In preferred embodiments, a cell-substrate impedance device useful in the methods of the present invention comprises a substrate that comprises one or more electrode arrays on its surface, in which each of the one or more electrode arrays comprises two electrodes or electrode structures, where the two electrodes or electrode structures have substantially the same surface area. In operation, a cell-substrate impedance device used in the methods of the present invention can detect impedance changes at one or more frequencies due to changes in cell number, cell size, cell morphology, cell attachment to the substrate, and the quality of cell attachment to the substrate.

Preferably a cell-substrate impedance device used in the methods of the present invention comprises at least one fluid container that surrounds an electrode array of the device and provides a fluid-impermeable container for cells being monitored. In preferred embodiments, a device comprises at least two arrays and at least two receptacles in the form of wells, where each array of the device is encompasses by a well. More preferably, a device used in the screening methods described in the present application comprises at least 8 wells (for example, devices comprising 16 or 96 wells), of which the majority comprise electrode arrays, so that assays can be performed in a high-throughput fashion. Cells can optionally be assayed in multiple multi-well devices simultaneously (for example, connected to the same impedance analyzer, engaged with a device station that can engage more than one multi-well device, or connected to separate impedance analyzers) to increase high-throughput capacity.

Systems for monitoring cell-substrate impedance that comprise one or more multiwell devices, an impedance analyzer, and a device station are described herein and are preferred but not required for use in the methods of the present invention.

The cells used in the IgE stimulation assays can be any cells, isolated from one or more organisms or from cell lines. Cells can be isolated from blood or other tissues of one or more organisms. Preferably the cells are mammalian cells. Preferably the cells are mast cells, basophils, or eosinophils, but that is not a requirement of the present invention. The cells can be genetically engineered cells of any type that express components of the IgE response pathway. Cells can be engineered to inappropriately express or overexpress components of the IgE response pathway. Cells can also be engineered to express dominant negative or other altered versions of components of the IgE response pathway, or to ablate expression of components of the IgE response pathway (for example, by use of homologous recombination knockouts, antisense or silencing RNA technologies). As used herein, "components of the IgE response pathway" also includes molecules suspected of being components of the IgE response pathway.

In some embodiments of some aspects of the present invention, RBL-2H3 rat mast cells can be used investigate the IgE-mediated signaling mechanism and also to assess the effect of various inhibitors on the signaling pathways leading to mast cell degranulation and mediator release. RBL-2H3 cells offer the advantage of being maintained and expanded in culture and a large body of literature which has utilized this cell line as a model system for IgE-mediated mast cell activation. However, the methods and systems of the present invention can readily be adapted to other cells that may be of academic and pharmaceutical interest. The cells include but are not limited to mouse bone marrow mast cells, human lung mast cells, human skin mast cells, and mast cells and basophils from other mammalian species.

The following subsections disclose assays that use impedance monitoring devices that can measure both IgE binding and antigen-mediated IgE-Fc(epsilon)RI cross-linking leading to mast cell morphological changes and degranulation. The assays can be performed in high-throughput format, in real time and without the need for any other reagents or cellular manipulation.

E.1. Methods for Monitoring Changes in Cell-Substrate Impedance in Response to IgE Stimulation IgE-mediated cell stimulation has been shown to lead to dramatic morphological changes in cells such as mast cells. For example, RBL-2H3 mast cells are transformed from spindle shape morphology to flattened and fibroblastic cell morphology. Cell-substrate impedance monitoring devices of the present invention can be used to detect cell shape changes and changes in cell-substratum interaction that result from IgE-mediated stimulation of responsive cells.

The method comprises: a) providing a device for cell-substrate impedance monitoring that comprising at least one well that comprises at least one electrode array; b) connecting an impedance analyzer to the device; c) introducing cells into one or more wells of the device that comprise an electrode array; d) adding IgE to the one or more wells comprising cells; e) adding at least one antigen, at least one allergen, or at least one IgE crosslinker to the one or more wells comprising cells; and f) monitoring cell-substrate impedance of the one or more wells comprising cells.

In the methods of the present invention, a device for cell-substrate impedance monitoring is a device that comprises a substrate having one or more electrode arrays on its surface each of which is encompassed by a fluid container in the form of a well. Each of the one or more electrode arrays comprises two electrodes or electrode structures, where the two electrodes or electrode structures have substantially the same surface area, in which the device, when connected to an impedance analyzer, can detect impedance changes at one or more frequencies due to changes in cell number, cell size, cell morphology, cell attachment to the substrate, or the quality of cell attachment to the substrate.

The cells can be any cells whose response or possible response to IgE stimulation is of interest. Preferred cells are mast cells, eosinophils, basophils, or genetically engineered cells. In some preferred embodiments, the cells are of mammalian origin.

IgE can be added before, after, or simultaneous with the addition of the antigen, allergen, or IgE crosslinker. IgE can be added to wells at a concentration of from about 10 nanograms per milliliter to about 1 microgram per milliliter. Preferably, one well of the device that comprises an electrode array and cells does not receive IgE to provide at least one control well, but this is not a requirement of the present invention.

Antigens, allergens, or crosslinkers can be known or suspected antigens, allergens, or crosslinkers. The concentration added to the wells can be from about 1 nanogram per milliliter to about 1 microgram per milliliter. Different wells may receive different concentrations of an antigen, allergen, or crosslinker. Or, for replica purposes, multiple wells may receive same concentrations of an antigen, allergen or crosslinker. Preferably, one well of the device that comprises an electrode array and cells does not receive antigen, allergen, or crosslinker to provide at least one control well, but this is not a requirement of the present invention.

The method can be used to assess and quantify the morphological changes that occur in mast cells as a result of IgE stimulation and IgE cross-linking with an antigen by using cell-substrate impedance technology. Impedance is preferably monitored during two or more phases of the experiment. For example, in one embodiment, impedance is monitored before and after the addition of IgE to the wells. In another embodiment, impedance is monitored before and after the addition of antigen, allergen, or crosslinker to the wells. In yet another embodiment, impedance can be monitored before and after the addition of IgE plus antigen, allergen, or crosslinker to the wells. Impedance can be also be monitored after the addition of IgE to the wells and before the addition of antigen, allergen, or crosslinker to the wells, as well as after the addition of antigen, allergen, or crosslinker to the wells. In some preferred embodiments, impedance is monitored before addition of IgE to the wells, after the addition of IgE to the wells and before the addition of antigen, allergen, or crosslinker to the wells, and after the addition of antigen, allergen, or crosslinker to the wells.

Impedance can be monitored at two or more time points. Preferably, impedance is monitored at at least three time points. Preferably, impedance is monitored at at least three time points at two or more phases of the assay. Impedance at each time point can be monitored at one or at more than one frequency. Data obtained from impedance monitoring can be used to assess morphological changes to cells that result from IgE stimulation. For example, impedance before and after addition of IgE, and/or before and after addition of antigen, allergen, or crosslinker can be compared for each well. Impedance data can be compared for wells that receive IgE and control wells that do not receive IgE. Impedance data can be compared for wells that receive antigen, allergen, or crosslinker and control wells that do not receive antigen, allergen, or crosslinker. Impedance data can be used to calculate a cell index, which can be used for comparisons.

One exemplary protocol is as follows:
(1) Add a predetermined number of mast cells to the wells of either a 16-well or 96 well cell-substrate impedance measurement device that is attached to an impedance analyzer.
(2) Allow the cells to attach and grow for 16-20 hours while recording the IgE anywhere from 10 nanogram/ mL to 1 microg/mL final concentration and continue recording the cellular response using a cell-substrate impedance monitoring system as described herein.

(3) At 16-20 hours after IgE stimulation, change media to serum free media. Allow the cells to recover for 30 minutes and then stimulate with antigen. Continue monitoring the cellular response to antigen on the impedance monitoring system.

E.2. Methods of Screening for Compounds that Can Modulate a Cellular Response to IgE Stimulation The present invention also includes methods of assessing the effect of one or more compounds on one or more cellular responses to IgE-mediated stimulation. The methods comprise: a) providing a device for cell-substrate impedance monitoring that comprising at least one well that comprises an electrode array; b) connecting an impedance analyzer to the device; c) introducing cells into one or more wells of the device that comprise an electrode array; d) adding at least one test compound to one or more of the one or more wells that comprise cells; e) adding IgE to the one or more wells comprising cells and at least one test compound; e) adding at least one antigen, at least one allergen, or at least one IgE crosslinker to the one or more wells comprising cells and at least one test compound; and f) monitoring cell-substrate impedance of the one or more wells comprising cells and at least one test compound.

In the methods of the present invention, a device for cell-substrate impedance monitoring is a device that comprises a substrate having one or more electrode arrays on its surface, each of which is encompassed by a fluid container in the form of a well. Each of the one or more electrode arrays comprises two electrodes or electrode structures, where the two electrodes or electrode structures have substantially the same surface area. The device, when connected to an impedance analyzer, can detect impedance changes at one or more frequencies due to changes in cell number, cell size, cell morphology, cell attachment to the substrate, or the quality of cell attachment to the substrate.

Preferably, a device used in the methods of the present invention is part of a cell-substrate impedance monitoring system as described herein.

The cells can be any cells that have a detectable response to IgE stimulation. Preferred cells are mast cells, eosinophils, basophils, or genetically engineered cells. In preferred embodiments, the cells are of mammalian origin.

IgE can be added before, after, or simultaneous with the addition of the antigen, allergen, or IgE crosslinker. IgE can be added to wells at a concentration of from about 10 nanograms per milliliter to about 1 microgram per milliliter. Optionally, one well of the device that comprises an electrode array and cells does not receive IgE to provide a control well.

Antigens can be known or suspected antigens, allergens, or crosslinkers. The concentration added to the wells can be from about 1 nanogram per milliliter to about 1 microgram per milliliter. Different wells may receive different concentrations of an antigen, allergen, or crosslinker. Or, for replica purposes, multiple wells may receive same concentrations of an antigen, allergen or crosslinker. Optionally, one well of the device that comprises an electrode array and cells does not receive antigen, allergen, or crosslinker to provide a control well.

A test compound can be any compound, including a small molecule, a large molecule, a molecular complex, an organic molecule, an inorganic molecule, a biomolecule such as but not limited to a lipid, a steroid, a carbohydrate, a fatty acid, an amino acid, a peptide, a protein, a nucleic acid, or any combination of theses. A test compound can be a synthetic compound, a naturally occurring compound, a derivative of a naturally-occurring compound, etc. The structure of a test compound can be known or unknown. One or many compounds can be assayed in a single experiment. Compounds can be tested in combination. Different concentrations of a given compound can be assayed using the methods of the present invention.

The advent of combinatorial chemistry has allowed for the generation of large and diverse compound libraries that can be used to screen for potential inhibitors of IgE-mediated mast cell activation. Assays can be performed in cell-substrate impedance monitoring systems of the present invention to screen compound libraries for potential inhibitors in high-throughput manner.

Test compounds can be compounds that interfere with IgE-mediated signaling through the Fc(epsilon)RI receptor expressed on the surface of mast cells and basophils. For example, a test compound can be an antibody raised against the IgE. or a recombinant protein comprising all or a portion of the antigen binding domain of Fc(epsilon)RI that can be tested for its ability to specifically bind to the IgE and prevent it from interacting with the endogenous Fc(epsilon) RI. Test compounds can also be candidates for small molecule inhibitor compounds that can bind to the IgE-binding pocket of Fc(epsilon)RI and block its interaction with the IgE molecule. Test compounds can also be siRNAs that can be tested for their ability to down-regulate the expression of Fc(epsilon)RI on the surface of mast cells.

Test compounds can also be screened to identify compounds that can act intracellularly to inhibit cellular response to IgE stimulation. For example, test compounds can be screened to identify inhibitors of kinases or lipases that have a role in cell signaling in response to IgE stimulation. For example, the methods of the present invention can be used to screen for compounds that can inhibit protein kinase C, SRC, Syk, or PLC(gamma).

A test compound is preferably added to wells prior to the addition of IgE, but can also be added after the addition of IgE and before the addition of antigen, or after the addition of IgE and antigen. In embodiments where IgE and antigen are added at the same time, a test compound can be added after but is preferably added after the addition of IgE and antigen.

The method can be used to assess and quantify the effects of a compound on the response of cells, such as but not limited to mast cells, as a result of IgE by using cell-substrate impedance technology. Impedance is preferably monitored during two or more phases of the experiment. Depending on the experimental protocol, impedance is preferably monitored after adding IgE to the one or wells, and is preferably monitored before and after adding IgE to the one or wells. Impedance is preferably monitored after the addition of test compound, before and after the addition of IgE. Impedance can also be monitored after the addition of test compound and IgE, before and after addition antigen. In some preferred embodiments, impedance is monitored after the addition of test compound and before addition of IgE to the wells, and after the addition of IgE to the wells and before the addition of antigen, allergen, or crosslinker to the wells, and after the addition of antigen, allergen, or crosslinker to the wells.

Impedance is preferably monitored at two or more time points. Preferably, impedance is monitored at at least three time points. Preferably, impedance is monitored at at least three time points at two or more phases of the assay. Impedance at each time point can be monitored at one or at more than one frequency. Data obtained from impedance monitoring can be used to assess the effects of a test compound on the morphological changes to cells that result from IgE stimulation. For example, impedance before and after addition of test compound, and/or before and after addition of IgE, and/or before and after addition of antigen, allergen, or crosslinker can be compared for each well. Impedance data can be compared for wells that receive test compound and control wells that do not receive test compound Impedance data can be used to calculate a cell index, which can be used for comparisons. Such comparisons can be used to identify compounds that inhibit the response of cells such as mast cells to IgE stimulation. For example, IC50s can be calculated from recorded impedance values for one or more test compounds that inhibit a cellular response to IgE stimulation One exemplary protocol for compound screening is as follows:

(1) A predetermined number of mast cells is added to the wells of either a 16-well or 96 well cell-substrate impedance measurement device that is part of a cell impedance monitoring system.
(2) The attachment and growth of the cells is monitored using the impedance monitoring system.
(3) The cells are pre-incubated with increasing concentrations of one or more potential inhibitors of interest (anti-IgE antibody, recombinant fragment of the Fc(epsilon)RI antigen binding domain or small molecular compounds) for a defined length of time.
(4) IgE specific for the cell line used is administered and the transient morphological changes of the cells due IgE stimulation is electronically monitored by the system. The extent of inhibition and IC-50 determination is assessed by comparing the peak response of the recording of the cells in the presence of increasing concentrations of the inhibitor.

In another example of the methods of the present invention, mast cells or other cells of interest are dispensed into a 96 well device either by liquid handling station or by multi-channel pipette. Cell attachment and growth is monitored as above. To assess the effect of the inhibitors on IgE-alone mediated signaling, inhibitors at a single concentration or multiple concentrations are pre-incubated with the cells prior to IgE application. The cellular response to IgE in the presence of the drug is then monitored as described above. Alternatively, if the effect of the drugs are to be assessed in response to the antigen cross-linking of the IgE-Fc(epsilon)RI complex, the inhibitors are preincubated with the cells just prior to the addition of the antigen as described above.

E.3 Methods for Target Validation of Enzymes and Proteins Involved in the Signaling Pathway Initiated by Engagement of the High-Affinity Fc(epsilon)RI Receptor in the Presence or Absence of IgE Cross-Linking by Antigen Using the Cell-Substrate Impedance Technology The intracellular signaling pathway that is stimulated by engagement of the Fc(epsilon)RI by IgE involves the activation of key enzymes such as but not limited to kinases, phosphatases and phospholipases. These downstream mediators of the cellular response to IgE are potential targets for pharmaceutical drug discovery. However, prior to screening for potential inhibitors of these target proteins and enzymes, they must be validated to ascertain that they can interfere with IgE-mediated signaling. This can be achieved by introducing into responsive cells by transfection, electroporation or viral infection the DNA encoding for the dominant negative versions of suspected target proteins or one or more siRNAs that target and reduce the expression of these proteins. Alternatively, antisense reagents can be used to reduce or ablate expression of a suspected target.

The method includes: a) providing a device for cell-substrate impedance monitoring that comprising at least one well that comprises an electrode array; b) connecting an impedance analyzer to the device; c) introducing cells into one or more wells of the device that comprise an electrode array, wherein said cells are genetically modified to alter the function of, or reduce or ablate the expression of, a suspected target molecule; d) adding IgE to the one or more wells comprising cells; e) adding at least one antigen, at least one allergen, or at least one IgE crosslinker to the one or more wells comprising cells; and f) monitoring cell-substrate impedance of the one or more wells comprising cells.

In the methods of the present invention, a device for cell-substrate impedance monitoring is a device that comprises a substrate having one or more electrode arrays on its surface, each of which is encompassed by a fluid container in the form of a well. Each of the one or more electrode arrays comprises two electrodes or electrode structures, where the two electrodes or electrode structures have substantially the same surface area. The device, when connected to an impedance analyzer, can detect impedance changes at one or more frequencies due to changes in cell number, cell size, cell morphology, cell attachment to the substrate, or the quality of cell attachment to the substrate.

Devices for measuring cell-substrate impedance are described in parent U.S. patent application Ser. No. 10/705,447 and in the present application. Preferably a cell-substrate impedance device used in the methods of the present invention comprises at least one fluid container that surrounds an electrode array of the device and provides a fluid-impermeable container for cells being monitored. In preferred embodiments, a device comprises at least two arrays and at least two receptacles in the form of wells, where each array of the device is encompassed by a well. More preferably, a device used in the screening methods described in the present application comprises at least 8 wells (for example, devices comprising 16 or 96 wells), of which the majority comprise electrode arrays, so that assays can be performed in a high-throughput fashion. Cells can optionally be assayed in multiple multi-well devices simultaneously (for example, connected to the same impedance analyzer, engaged with a device station that can engage more than one multi-well device, or connected to separate impedance analyzers) to increase high-throughput capacity.

Systems for monitoring cell-substrate impedance that comprise one or more multiwell devices, an impedance analyzer, and a device station are described herein and are preferred but not required for use in the methods of the present invention.

The genetically modified cells can be any type of cells that is responsive to IgE stimulation. Preferably, mast cells are used, such as RBL-2H3 rat mast cells. Methods of genetically modifying cells are well known in the art, and include introducing expression constructs that direct the expression of altered versions of the suspected target protein (for example, dominant negative versions of a protein), introducing expression constructs that direct the expression of antisense RNAs that can reduce or ablate the expression of a target protein, and introducing expression constructs that direct the expression of silencing RNAs that can reduce or ablate the expression of a target protein. Antisense or gene silencing reagents can also be added to cultured cells before or after adding the cells to a device of the present invention.

Preferably, control cells that have not been genetically modified are also assayed alongside genetically modified cells.

Ig E can be added before, after, or simultaneous with the addition of the antigen, allergen, or IgE crosslinker. IgE can be added to wells at a concentration of from about 10 nanograms per milliliter to about 1 microgram per milliliter. Optionally, one well of the device that comprises an electrode array and cells does not receive IgE to provide a control well.

Antigens used in the assays can be antigens, allergens, or crosslinkers. The concentration added to the wells can be from about 1 nanogram per milliliter to about 1 microgram per milliliter.

The method can be used to assess and quantify the effects of a compound on the response of cells, such as but not limited to mast cells, as a result of IgE by using cell-substrate impedance technology. Impedance is preferably monitored during two or more phases of the experiment. Depending on the experimental protocol, impedance is preferably monitored after adding IgE to the one or wells, and is preferably monitored before and after adding IgE to the one or wells. Impedance is preferably monitored after the addition of test compound, before and after the addition of IgE. Impedance can also be monitored after the addition of test compound and IgE, before and after addition antigen. In some preferred embodiments, impedance is monitored after the addition of test compound and before addition of IgE to the wells, and after the addition of IgE to the wells and before the addition of antigen, allergen, or crosslinker to the wells, and after the addition of antigen, allergen, or crosslinker to the wells.

Impedance is preferably monitored at two or more time points. Preferably, impedance is monitored at at least three time points. Preferably, impedance is monitored at at least three time points at two or more phases of the assay. Impedance at each time point can be monitored at one or at more than one frequency. For example, impedance values before and after addition of IgE, and/or before and after addition of antigen can be compared for each well. Impedance data can be compared for wells that comprise genetically manipulated cells and control wells comprise cells that are not genetically manipulated. Impedance data can be used to calculate a cell index, which can be used for comparisons. Such comparisons can be used to identify genes that affect the response of cells to IgE stimulation.

Data obtained from impedance monitoring can be used to assess the effects of a genetic manipulation (such as expression knockdown, expression knockout, or dominant negative expression) on the morphological changes to cells that result from IgE stimulation. Identification of a genetic manipulation that affects the morphological changes to cells that result from IgE stimulation is used to identify a gene, and thus a gene product, that has a role in the IgE response.

One example of an assay of the present invention for validating a target is as follows:
(1) Provide cells having either the DNA for the dominant negative version of a protein of interest or for siRNA targeting of a protein of interest.
(2) Transfer cells to wells of a device of an impedance monitoring system and monitor the attachment and growth of the cells as described above. Alternatively, gene interfering reagents can be directly introduced into the cells in the wells of the device.
(3) Cells are stimulated with IgE in the presence or absence of antigen and the cellular response is recorded by the impedance monitoring system as previously discussed. The ability of a genetic construct or reagent to interfere with the response of cells to IgE stimulation by antigen will allow identification of the molecule the construct or reagent acts against as a potential target for drug discovery.

E.4 Method for Screening Genetic Markers that Determine or Influence Engagement of High-Affinity Fc(epsilon)RI Cross-Linking and Subsequently Mast Cell Activation It is well known that host genetic background determines the types and severity of allergic response to similar antigens. The present invention also includes methods of comparing the responses of cell of different genotypes to antigen-mediated IgE stimulation. The responses of cells of different genotypes to antigen-mediated IgE stimulation can be correlated with any of a number of genetic markers that the cells of different genotypes display.

The method includes: a) providing a device for cell-substrate impedance monitoring that comprising at least one well that comprises an electrode array; b) connecting an impedance analyzer to the device; c) introducing cells of a first genotype into at least one well of the device; d) introducing cells of a second genotype into at least one other well of the device; e) adding IgE to at least one well comprising cells of a first genotype and at least one well comprising cells of a second genotype; f) adding at least one antigen to the one or more wells comprising cells of a first genotype and to the one or more wells comprising cells of a second genotype; g) monitoring cell-substrate impedance of the one or more wells comprising cells of a first genotype and of the one or more wells comprising cells of a second genotype; and g) comparing the cell-substrate impedance values of the one or more wells comprising cells of a first genotype with the cell-substrate impedance values of the one or more wells comprising cells of a second genotype.

Preferably, the method further includes: correlating at least one genetic marker with the cell substrate impedance values obtained from monitoring cells of said first genotype and cells of said second genotype.

In the methods of the present invention, a device for cell-substrate impedance monitoring is a device that comprises a substrate having one or more electrode arrays on its surface, each of which is encompassed by a fluid container in the form of a well. Each of the one or more electrode arrays comprises two electrodes or electrode structures, where the two electrodes or electrode structures have substantially the same surface area. The device, when connected to an impedance analyzer, can detect impedance changes at one or more frequencies due to changes in cell number, cell size, cell morphology, cell attachment to the substrate, or the quality of cell attachment to the substrate.

Devices for measuring cell-substrate impedance are described in parent U.S. patent application Ser. No. 10/705, 447 and in the present application. Preferably a cell-substrate impedance device used in the methods of the present invention comprises at least one fluid container that surrounds an electrode array of the device and provides a fluid-impermeable container for cells being monitored. In preferred embodiments, a device comprises at least two arrays and at least two receptacles in the form of wells, where each array of the device is encompassed by a well. More preferably, a device used in the screening methods described in the present application comprises at least 8 wells (for example, devices comprising 16 or 96 wells), of which the majority comprise electrode arrays, so that assays can be performed in a high-throughput fashion. Cells can optionally be assayed in multiple multi-well devices simultaneously (for example, connected to the same impedance analyzer, engaged with a device station that can engage more than one multi-well device, or connected to separate impedance analyzers) to increase high-throughput capacity.

Systems for monitoring cell-substrate impedance that comprise one or more multiwell devices, an impedance analyzer, and a device station are described herein and are preferred but not required for use in the methods of the present invention.

The cells used in the methods of the present invention can be any IgE responsive cells, but are preferably mast cells isolated from different individuals. In addition to impedance monitoring, mast cells isolated from individuals can be analyzed for genetic markers. These genetic markers include, as nonlimiting examples, SNPs, mutations, alternative RNA splicing variants, gene expression profiles, and protein expression profiles. Methods of analyzing genetic markers using cell isolated from individuals is well-known in the art.

In the assay procedure, IgE can be added before, after, or simultaneous with the addition of the antigen. IgE can be added to wells at a concentration of from about 10 nanograms per milliliter to about 1 microgram per milliliter. Optionally, one well of the device that comprises an electrode array and cells does not receive IgE to provide a control well.

Antigens used in the assays can be antigens, allergens, or crosslinkers. The concentration added to the wells can be from about 1 nanogram per milliliter to about 1 microgram per milliliter. Antigens can be chosen for their characteristic propensity to be identified as allergens among members of a population.

The method can be used to correlate a genetic marker with the antigen-IgE response of cells, such as but not limited to mast cells, as a result of by using cell-substrate impedance technology. Impedance is preferably monitored during two or more phases of the experiment. Depending on the experimental protocol, impedance is preferably monitored after adding IgE to the one or wells, and is preferably monitored before and after adding IgE to the one or wells. Impedance is preferably monitored after the addition of test compound, before and after the addition of IgE. Impedance can also be monitored after the addition of test compound and IgE, before and after addition antigen. In some preferred embodiments, impedance is monitored after the addition of test compound and before addition of IgE to the wells, and after the addition of IgE to the wells and before the addition of antigen, allergen, or crosslinker to the wells, and after the addition of antigen, allergen, or crosslinker to the wells.

Impedance is preferably monitored at two or more time points. Preferably, impedance is monitored at at least three time points. Preferably, impedance is monitored at at least three time points at two or more phases of the assay. Impedance at each time point can be monitored at one or at more than one frequency. For example, impedance values before and after addition of IgE, and/or before and after addition of antigen can be compared for each well. Impedance data can be compared for wells that comprise genetically manipulated cells and control wells comprise cells that are not genetically manipulated. Impedance data can be used to calculate a cell index, which can be used for comparisons. Such comparisons can be used to identify genetic markers that affect the response of cells to IgE stimulation.

Data obtained from impedance monitoring can be used to correlate genetic markers assigned to the cells with the responses of the cells to IgE stimulation. Identification of a genetic marker that correlates with the responsiveness of cells to IgE can be used to develop strategies for developing therapies that moderate the IgE response.

An exemplary assay is as follows:
1) Isolate mast cells from two or more individuals potent to allergic reactions
2) Identify genetic markers of interest in the individuals
3) Incubate the mast cells (or differentiate stem cells to mast cells in the presence of specific differentiation factors)
4) Transfer the cells to impedance monitoring devices and monitor the cell growth
5) Add IgE (human) with or without an allergen
6) Quantify mast cell impedance response
7) Correlate genetic markers with mast cell response Genetic analysis can be conducted using standard RFLP and SNP analysis, RNA and protein expression profiling, and RNA splicing detection methods as they are known in the art. Preferably, assays are performed in a high throughput manner using cells from a very large number of individuals to provide robust correlations of genetic markers and IgE responses.

E.4 Method for Screening, Discovering, and Validating Chemical Structures of Antigen (Allergen) or Half Antigen Binding the IgE Receptor Leading to Receptor Cross-Linking The present invention also provides methods of identifying antigens or half-antigens that can cause an allergic response. The method comprises: a) providing a device for cell-substrate impedance monitoring that comprising at least one well that comprises at least one electrode array; b) connecting an impedance analyzer to the device; c) introducing cells into one or more wells of the device that comprise an electrode array; d) adding IgE to the one or more wells comprising cells; e) adding at least one suspected antigen or at least one suspected allergen or half-allergen to the one or more wells comprising cells; and f) monitoring cell-substrate impedance of the one or more wells comprising cells.

In the methods of the present invention, a device for cell-substrate impedance monitoring is a device that comprises a substrate having one or more electrode arrays on its surface each of which is encompassed by a fluid container in the form of a well. Each of the one or more electrode arrays comprises two electrodes or electrode structures, where the two electrodes or electrode structures have substantially the same surface area, in which the device, when connected to an impedance analyzer, can detect impedance changes at one or more frequencies due to changes in cell number, cell size, cell morphology, cell attachment to the substrate, or the quality of cell attachment to the substrate.

The cells can be any cells whose response or possible response to IgE stimulation is of interest. Preferred cells are mast cells, eosinophils, basophils, or genetically engineered cells. In some preferred embodiments, the cells are of mammalian origin. In some preferred embodiments, the cells are mast cells isolated from individuals.

IgE can be added before, after, or simultaneous with the addition of the antigen, allergen, or half-allergen. IgE can be added to wells at a concentration of from about 10 nanograms per milliliter to about 1 microgram per milliliter. Preferably, one well of the device that comprises an electrode array and cells does not receive IgE to provide at least one control well, but this is not a requirement of the present invention.

Antigens, allergens, or half-allergens can be known or suspected antigens, allergens, or allergens. The concentration added to the wells can be from about 1 nanogram per milliliter to about 1 microgram per milliliter. Different wells may receive different concentrations of an antigen, allergen, or half-allergens. Or, for replica purposes, multiple wells may receive same concentrations of an antigen, allergen or crosslinker. Preferably, one well of the device that comprises an electrode array and cells does not receive antigen, allergen, or half-allergen to provide at least one control well, but this is not a requirement of the present invention.

The method can be used to assess and quantify the morphological changes that occur in mast cells as a result of IgE stimulation and IgE cross-linking with an allergen by using cell-substrate impedance technology. Impedance is preferably monitored during two or more phases of the experiment. For example, in one embodiment impedance is monitored before and after the addition of antigen, allergen, or half-allergen to the wells. In another embodiment, impedance is additionally monitored before and after the addition of IgE to the wells. In yet another embodiment, impedance can be monitored before and after the addition of IgE plus antigen, allergen, or half-allergen to the wells. Impedance can be also be monitored after the addition of IgE to the wells and before the addition of antigen, allergen, or half-allergen to the wells, as well as after the addition of antigen, allergen, or half-allergen to the wells. In some preferred embodiments, impedance is monitored before addition of IgE to the wells, after the addition of IgE to the wells and before the addition of antigen, allergen, or half-allergen to the wells, and after the addition of antigen, allergen, or half-allergen to the wells.

Impedance can be monitored at two or more time points. Preferably, impedance is monitored at at least three time points. Preferably, impedance is monitored at at least three time points at two or more phases of the assay. Impedance at each time point can be monitored at one or at more than one frequency. Data obtained from impedance monitoring can be used to assess morphological changes to cells that result from IgE stimulation. For example, impedance before and after addition of IgE, and/or before and after addition of antigen, allergen, or half-allergen can be compared for each well. Impedance data can be compared for wells that receive IgE and control wells that do not receive IgE. Impedance data can be compared for wells that receive antigen, allergen, or half-allergen and control wells that do not receive antigen, allergen, or crosslinker. Impedance data can be used to calculate a cell index, which can be used for comparisons.

One exemplary protocol is as follows:
(1) Mast cells are seeded into wells of an impedance monitoring device.
(2) The cells are monitored electronically using an impedance monitoring system for a given amount of time.
(3) The IgE that is specific for the allergen or the half allergen will be added to the cells.
(4) Cellular response will be monitored by using the system
(5) After a pre-determined increment of time, the antigen or half antigen that is specific for the IgE in step (3) will be added.
(6) Cellular response will continue to be monitored using the system.

Example 1

As an example, we describe here the use of the use of a cell-substrate impedance monitoring system of the present invention to measure and monitor the morphological changes that occur as a result of IgE-mediated stimulation of RBL-2H3 cells (ATCC) in the presence or absence of an antigen. The cell-substrate impedance monitoring system has a device station that can engage 6 16× devices as depicted in FIG. 4. It also has an impedance analyzer, and software that directs impedance measurement and recording and analysis of impedance data.

RBL-2H3 cells were seeded in the 16× device chamber (depicted in FIG. 2) at 20,000 cells/well and the attachment and growth of the cells in the 37° C. tissue culture incubator were monitored in real-time using the cell-substrate monitoring system. After 22 hours mouse monoclonal anti-dinitrophenyl (DNP) antibody (Clone SPE-7, Sigma) was added at final concentration of 1 microgram/mL. As a control, a non-specific mouse IgG was added at a final concentration of 1 microgram/mL. The device chambers were returned to the incubator and recording was resumed. At 24 hours post-IgE stimulation the media in the chamber was aspirated and 150 microliters of fresh media was added to the cells. Recording was resumed for 1 hour followed by the addition of DNP-albumin (Sigma) at a final concentration of 1 microgram/ml. The recording was continued for an additional 4 hours.

Figure 13:
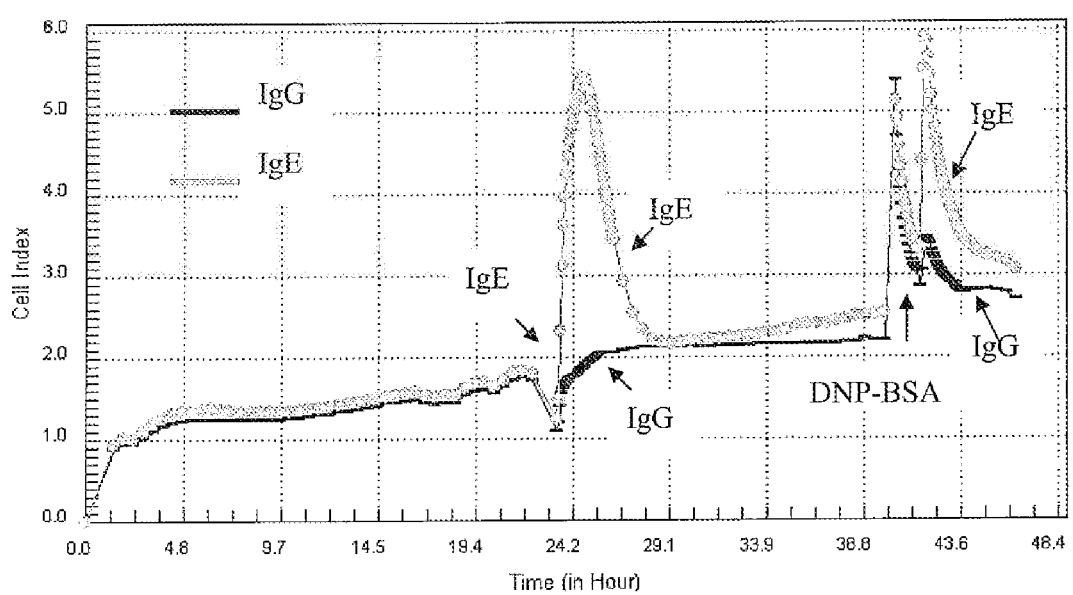
FIG. 13 is a plot of cell index recording indicating mast cell responses to IgE in the presence or absence of antigen. 20,000 RBL-2H3 mast cells were seeded in each well of a 16× device. Cells were allowed to adhere and grow for 22 hours while being recorded. At 22 hours the cells were treated with either 1 microgram/mL non-specific mouse IgG or 1 microgram/mL anti-DNP mouse IgE. The electronic impedance response of the cells were continued to be recorded for an additional 20 hours after which the media in the wells were aspirated and replaced with fresh serum free media. The cells were allowed to recover for 30 minutes and then treated with the 1 microgram/mL of the antigen, DNP-BSA. The electronic impedance response of the cells was measured for an additional 3 hours.

RBL-2H3 mast cells have been used extensively as a model system to investigate the signaling pathways that are initiated as a result of IgE-mediated binding to and stimulation of the high affinity Fc(epsilon)RI receptors located on the membrane. Mast cell degranulation is accompanied by distinct morphological changes which involve the actin cytoskeleton (Pfeiffer et al. J Cell Biol. 1985 December; 101(6):2145-55.). Engagement of Fc(epsilon)RI by IgE, even in the absence of cross-linking by an antigen, leads to dose-dependent degranulation and morphological changes (Oka et al. Am J Physiol Cell Physiol. 2003 Sep. 17). This IgE-mediated dose-dependent phenomenon is also observed using the impedance system as shown in FIG. 13. It is observed as an abrupt shift in the trace of the cell index number at 22 hours, immediately after the administration of the IgE. The duration of the signal for the IgE concentrations that illicit a change lasts for approximately 6 hours. Such dynamic changes are consistent with morphological dynamics observed by microscopy and degranulation detected by enzymatic assays. Importantly, the shift in the trace does not occur in those wells which have IgG, indicating that the response is specific for IgE. The peak amplitude of the recording is directly dependent on the concentration of the IgE used to stimulate the cells. The duration of the signal for the IgE concentrations that illicit a change lasts for approximately 6 hours.

Once RBL-2H3 mast cells have been sensitized with IgE, further degranulation and actin-mediated morphological dynamics can be elicited by the administration of the antigen to which the IgE has been raised against. In RBL-2H3 cells this has been observed by immunofluorescence microscopy as extensive membrane ruffling and lamellapodia formation on the apical surface of the cells. The phenomenon of antigen-mediated IgE-dependent mast cell degranulation and morphological dynamics can also be monitored and measured using cell-impedance monitoring system. 20 hours after IgE addition the media is removed and replaced by fresh media. The change in media also induces a non-specific transient change in the signal which immediately returns to baseline after 30 minutes. Application of DNP-albumin at this point induced an abrupt shift in the recording which peaks at about 15-20 minutes and returns to baseline about 1 hour later. The duration of the shift in the signal is much more transient under these conditions, when compared to IgE alone stimulation (3 hours vs. 6 hours).

Example 2

The following example is provided to show how a real-time cell electronic sensing system and methods can be used in real-time monitoring of IgE-mediated mast cell activation. The methods and devices of the present invention are not limited to those described in the Examples. Indeed, within the scope of the present invention, there are other specific methods and approaches to conduct assays for monitoring IgE-mediated mast cell signaling and activation.

Introduction

The work presented here describes an assay for IgE-mediated mast cell activation using measurements of cell-substrate impedance. The method is based on quantification in real time of the morphological, cytoskeletal and cell adhesion changes that arise as a response to multivalent antigen aggregation of the IgE-Fc(epsilon)RI complex on the surface of mast cells. Because the electronic assay readout relies on morphological, cytoskeletal and adhesive dynamics, which are intrinsic mast cell responses to the antigen and an essential part of the mast cell activation program, it precludes the need for establishing reporter cell lines or using any other reagent or cellular manipulation. Since the assay is performed in real time, both antigen-dependent and independent responses to IgE-mediated activation of mast cells can be monitored in the same assay. The assay is readily adaptable to a 96 well format and as shown here can be used to assay for pharmacological inhibitors of mast cell activation in high throughput manner.

Materials and Methods

Cells and Reagents

The RBL-2H3 cell line was purchased from American Type Culture Collection (ATCC) and maintained in DMEM containing 10% fetal bovine serum at 37° C. and 5% $CO_2$. Mouse monoclonal anti-dinitrophenyl IgE antibody (Clone SPE-7) and DNP-HSA were purchased from Sigma Aldich (St. Louis, Mo.). The Src-specific inhibitor SU6656, MEK-specific inhibitor PD98059 and the PLC-specific inhibitor U73122 were purchased from Calbiochem (La Jolla, Calif.). The PKC-specific inhibitor Bisindolylmaleimide and the Syk inhibitor Piceatannol were purchased from Sigma. Rhodamine phalloidin was obtained from Molecular Probes (Eugene, Oreg.). Lab-Tek chamber slides were purchased through VWR Scientific.

Cell-Substrate Impedance Monitoring System

The real-time cell-substrate impedance monitoring system comprises three components, an impedance analyzer, a device station, and one or more 16× microtiter devices. Microelectrode sensor arrays were fabricated on glass slides using lithographical microfabrication methods and the electrode-containing slides were assembled to plastic trays to form 16 electrode-containing wells. The device station of the system receives the 16× microtiter devices and is capable of electronically switching any one of the wells to the sensor (impedance) analyzer for impedance measurement. In operation, the devices with cells cultured in the wells are placed into a device station that is located inside an incubator. Electrical cables connect the device station to the sensor (impedance) analyzer. Under the impedance monitoring system's software control, the impedance analyzer can automatically select wells to be measured and continuously conduct impedance measurements. The impedance data from the analyzer is transferred to a computer, analyzed and processed by integrated software.

Impedance measured between electrodes (electrode elements) in an individual well depends on electrode geometry, ionic concentration in the well and whether there are cells attached to the electrodes. In the absence of cells, electrode impedance is mainly determined by the ion environment both at the electrode/solution interface and in the bulk solution. In the presence of cells, cells attached to the electrode sensor surfaces will alter the local ionic environment at the electrode/solution interface, leading to an increase in the impedance. The more cells there are on the electrodes, the larger the increase in cell-electrode impedance. Furthermore, the impedance change also depends on cell morphology and the extent to which cells attach to the electrodes.

To quantify cell status based on the measured cell-electrode impedance, a parameter termed Cell Index is derived, according to $$CI = \max_{i=1,...,N} \left( \frac{R_{cell}(f_i)}{R_b(f_i)} - 1 \right)$$

where $R_b(f)$ and $R_{cell}(f)$ are the frequency dependent electrode resistances (a component of impedance) without cells or with cell present, respectively. N is the number of the frequency points at which the impedance is measured. Thus, Cell Index is a quantitative measure of the status of the cells in an electrode-containing well. Under the same physiological conditions, more cells attached on to the electrodes leads to larger $R_{cell}(f)$ value, leading to a larger value for Cell Index. Furthermore, for the same number of cells present in the well, a change in the cell status such as morphology will lead to a change in the Cell Index. For example, an increase in cell adhesion or cell spreading leads to larger cell-electrode contact area which will lead to an increase in $R_{cell}(f)$ and thus a larger value for Cell Index.

Fluorescence Microscopy

RBL-2H3 cells were seeded in 16 well Lab-Tec chamber slides and allowed to attach and spread for 6 hours. The cells were stimulated with anti-DNP IgE at a final concentration of 100 ng/mL or a non-specific mouse IgG at 100 ng/mL and then 16 hours later, the media was aspirated, replaced with fresh media and treated with 100 ng/mL DNP-BSA for the indicated time and then fixed with 4% parafarmaldehyde. The cells were washed 3× with PBS, permeablized in PBS containing 0.2% TX-100 and blocked in PBS containing 0.5% BSA. The cells were then stained with rhodamine-phalloidin for 30 minutes, washed 3× with PBS and visualized and imaged using the tritc filter on a Nikon E400 epi-fluorescence microscope and Nikon ACT software.

2.5. Beta-Hexosaminidase Assay

RBL-2H3 cells growing in 96 well plates were washed and incubated in Tyrode buffer (10 mM Hepes, pH 7.4, 130 mM NaCl, 5 mM KCl, 1.4 mM CaCl2, 1 mM MgCl2, 5.6 mM Glucose, and 0.1% BSA) and stimulated with 100 ng/mL anti-DNP IgE. After 2 hours the supernatant was removed and the cell monolayer was lysed in Tyrode buffer containing 0.5% TX-100. Hexosaminidase activity was measured in both supernatant and the cell monolayer using the substrate 4-nitrphenyl-2acetamido-2-deoxy-b-D-glucopyranoside (1 mg/mL). After 1 hour incubation at 37° C., the reaction was stopped by the addition of 2 volumes of 0.4 M glycine pH 10.7. The absorbance at 405 nm was read in Molecular Devices ELISA reader.

Impedance Assay 20,000 RBL-2H3 cells were seeded per well of a 16× microtiter device and monitored by the impedance measuring system. The cells were allowed to attach and spread for 5-24 hours prior to the addition of IgE at the indicated final concentration. The cell-electrode impedance was continuously measured and the corresponding, time dependent Cell-Index values were derived and recorded.

Impedance Monitoring of RBL-2H3 Mast Cell Activation

IgE-mediated RBL-2H3 mast cell activation in the presence of antigen leads to initiation of signaling cascade resulting in degranulation of secretory vesicles which contain mediators of allergic reaction such as histamine. In addition, IgE-mediated stimulation through Fc(epsilon)RI also leads to dramatic remodeling of the actin cytoskeleton (Oliver et al., 1997). Since monitoring of cell-electrode impedance provides information about the parameters of cell morphology and adhesion we sought to determine the impedance response of RBL-2H3 mast cells that were pre-sensitized with IgE in the presence of antigen application.

Figure 14:
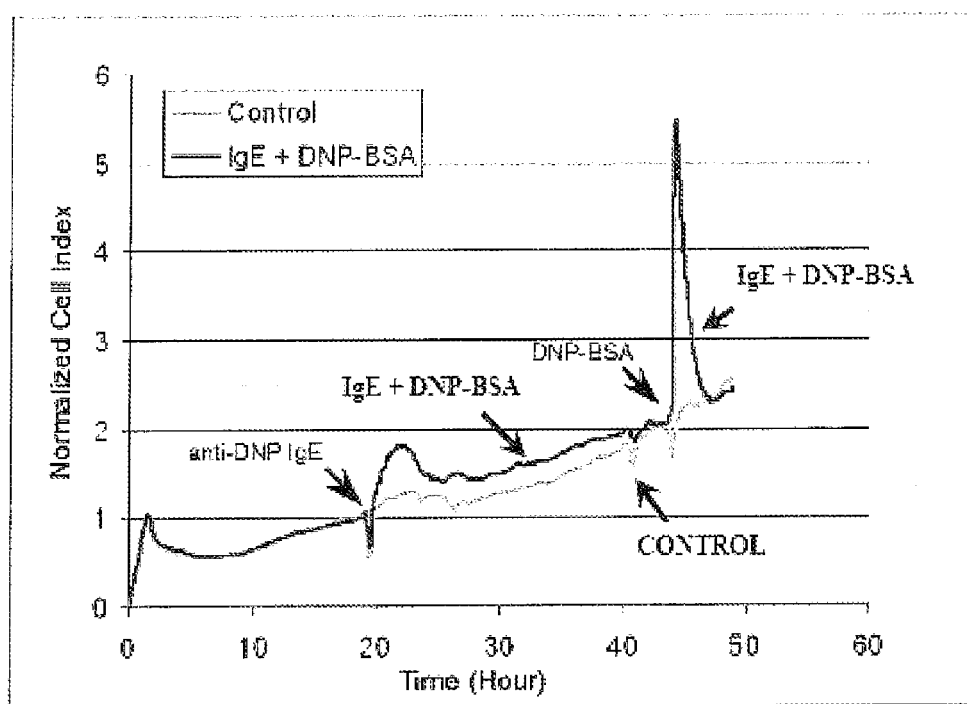
FIG. 14 shows the results of another experiment monitoring cell-electrode impedance responses of RBL-2H3 mast cells sensitized with anti-DNP IgE and activated by the application of DNP-BSA. RBL-2H3 mast cells were seeded at a density of 20,000 cells/well onto the surface of a 16× device and the impedance was continuously measured and Cell Index recorded every 30 minutes using a cell-substrate impedance monitoring system of the present invention.

RBL-2H3 mast cells were seeded onto the surface of 16× microtiter plate devices having integrated microelectronic sensor arrays in the bottom of each well. The cells were allowed to adhere to the surface of the sensors and 18 hours later were sensitized with anti-DNP IgE (FIG. 14). Approximately 24 hours later DNP-BSA at a final concentration of 100 ng/mL was applied to the cells to induce oligomerization of the IgE-bound Fc(epsilon)RI receptor and induce mast cell activation. The cell-electrode impedance measurements were continuously monitored using the impedance monitoring system. As shown in FIG. 14, DNP-BSA application induced an immediate and transient increase in the impedance value which was detectable within 5 minutes of DNP-BSA application, maximal by 30 minutes and returned to baseline in approximately 2.5 hours. IgE-mediated activation of mast cells not only led to dramatic morphological changes (Pfeiffer et al., 1985) but also to augmentation of integrin-mediated cell adhesion (Wyczolkowska et al., 1994), both of which contributed to cell-electrode impedance measurements using the impedance monitoring system.

Impedance Measurement of Mast Cell Activation Correlates with Cytoskeletal Dynamics and Degranulation To determine if the IgE-mediated cell-electrode impedance increase correlates with RBL-2H3 mast cell activation, both IgE-mediated morphological dynamics and mediator release were monitored.

RBL-2H3 mast cells were sensitized and activated as described above and at the indicated time points, fixed with parafarmaldehyde and stained with rhodamine-phalloidin to visualize the actin cytoskeleton (FIG. 15A). As seen in FIG. 15A and shown previously (Pfeiffer et al., 1985; O'Luanaigh et al., 2002; Powner et al., 2002), DNP-BSA-mediated cross-linking of the Fc(epsilon)RI receptor leads to time-dependent remodeling of the actin cytoskeleton. The cells undergo extensive ruffling which is apparent as early as 2.5 minutes post IgE stimulation, followed by morphological changes which lead to cell spreading and formation of lamellapodia. The peak cytoskeletal reorganization is observed at 30-45 minutes post-IgE stimulation which correlates directly with the peak cell-electrode impedance response using the impedance monitoring system. As a control, RBL-2H3 mast cells were also sensitized with an irrelevant IgG and subsequently cross-linked with DNP-BSA. No obvious cytoskeletal and morphological changes were observed.

As an additional marker for RBL-2H3 mast cell activation, beta-hexosaminidase activity was also measured in response to IgE stimulation in the presence of antigen cross-linking. The enzyme beta-hexosaminidase is stored within the secretory vesicles and is a marker for mast cell degranulation. It has been shown that beta-hexosaminidase is released into the culture media in response to antigen-mediated cross-linking of IgE-bound Fc(epsilon)RI on the surface of mast cells (Razin et al., 1983). RBL-2H3 cells were sensitized with anti-DNP IgE, activated by application of DNP-BSA and beta-hexoseaminidase activity was measured as described in materials and methods section. Antigen cross-linking leads to a two and a half to 4 fold increase in beta-hexosaminidase depending on the experiment (FIG. 15B). Taken together, IgE-mediated mast cell-electrode impedance increase correlates directly with morphological changes and degranulation which is characteristic of mast cell activation. Therefore, cell-electrode impedance measurements can be used as readout for mast cell activation.

Cell-Substrate Monitoring of RBL-2H3 Sensitization Step

It has recently been shown that high concentrations of monomeric IgE induce mast cell activation in the absence of antigen cross-linking (Oka et al., 2004). Accordingly, we wanted to determine if high concentrations of IgE alone may induce an increase in cell-electrode impedance response. RBL-2H3 mast cells growing on the surface of 16× microtiter cell-substrate impedance monitoring devices were stimulated with increasing amounts of IgE-ranging from 15 nanogram/mL to 1 micrograms/mL and their impedance response was continuously monitored (FIG. 16A). IgE application alone leads to a dose-dependent increase in cell-electrode impedance response which correlated with morphological dynamics and mediator release. To determine if the initial concentration of IgE used to sensitize the cells influences the subsequent antigen-mediated response, RBL-2H3 cells were sensitized with the indicated concentrations of anti-DNP IgE and after 16 hours were incubated with 100 nanograms/mL final concentration of DNP-BSA. As shown in FIG. 16B, the DNP-BSA-mediated response is inversely proportional to the initial anti-DNP IgE concentration used to sensitize the cells. Sensitizing with 1 microgram/ml anti-DNP IgE leads to negligible increase in cell-electrode impedance response when cross-linked with the multi-valent antigen DNP-BSA while sensitization with 15 nanograms/mL anti-DNP IgE resulted in a robust increase in cell-electrode (cell-substrate) impedance in the presence of DNP-BSA aggregation. Furthermore, if the increment of time between High IgE application and DNP-BSA addition is increased to 24 hours, then the cell will undergo antigen-mediated activation.

In conclusion these experiments illustrate that IgE concentration and the timing between IgE sensitization and subsequent antigen stimulation is critical and should be taken into account. Additionally, these experiments further illustrate the advantage of real-time monitoring of mast cell activation on microelectronic cell-substrate impedance sensor arrays with respect to cell status and response at any given time point.

Pharmacological Inhibition of Mast Cell Activation as Detected by the Cell-Substrate Impedance Monitoring System Antigen-mediated aggregation of the IgE-bound Fc(epsilon)RI triggers a signaling cascade which involves a number of signaling proteins such as protein kinases, protein phosphatases, and phospholipases amongst others whose activity and function is indispensable for mast cell activation (Turner and Kinet, 1999). Accordingly, we were interested in determining if pharmacological inhibitory effects of some of these signaling proteins can be monitored by mast cell-electrode impedance measurement.

RBL-2H3 cells were seeded in a 16× microtiter plate device and pre-stimulated with anti-DNP-IgE were incubated for 1 hour with the indicated doses of the PKC-specific inhibitor Bisindolylmaleimide and subsequently treated with 100 ng/mL DNP-BSA (FIG. 17). The dose-dependent inhibition of RBL-2H3 mast cell activation by Bisindolylmaleimide can be monitored on the cell-substrate monitoring system in real-time. A number of other pharmacological agents such as SU6656, specific for Src family kinases, U73122, specific for phospholipase C, Piceatannol, specific for Syk tyrosine kinase and PD98059 specific for MEK were also tested. The IC-50 value for these pharmacological inhibitors at peak response was calculated and is shown in Table I. All the inhibitors with the exception of PD 98059 dose dependently inhibited antigen-mediated RBL-2H3 mast cell activation. The PLC-specific inhibitor U73122 displayed potent inhibitory effect with an IC-50 value of around 1 microM. The Src and Syk specific inhibitors also inhibited the antigen-mediated response although at higher concentrations (Table I). The MEK-specific inhibitor PD 98059 had minimal effect on IgE-mediated RBL-2H3 response at the concentrations tested.

In order to ascertain that inhibitor-mediated abrogation of the cell-electrode impedance response correlates with inhibition of mast cell activation, the beta-hexosaminidase activity of IgE stimulated RBL-2H3 cells were measured in the presence of pharmacological agents. According to FIG. 18, SU6656, U73122, Bisindolylmaleimide and Piceatannol abrogated the anti-DNP IgE mediated stimulation of beta-hexosaminidase activity in the presence of antigen aggregation whereas the MEK specific inhibitor had minimal effect. These findings are in agreement with previously published data indicating that the Src, PLC, PKC and Syk specific inhibitors completely block IgE-mediated mast cell degranulation and activation (Oliver et al., 1994; Amoui et al., 1997; Moriya et al., 1997; Tedeschi et al., 2000). In summary, the results presented here indicate that real-time monitoring of IgE-mediated mast cell activation on microelectronic cell sensor arrays offer a convenient way of assessing mast cell activation. The assay does not require any cellular manipulation such as labeling, fixation or lysis. The assay was validated by demonstrating that the cell-electrode (cell-substrate) impedance measurement correlates directly with IgE-mediated mast cell activation as measured by actin cytoskeleton dynamics and mediator release. Furthermore, previously characterized specific inhibitors of mast cell activation pathway inhibit mast cell activation as measured by the cell-substrate impedance monitoring system, further validating this assay.

TABLE I

IC-50 determination of pharmacological agents inhibiting mast cell activation monitored by cell-substate impedance monitoring.

| Compound | Target | IC50 ± SD (µM) |
| --- | --- | --- |
| Bisindolylmaleimide | Protein Kinase C | 2.9 ± 1.7 (N = 3) |
| SU6656 | SRC | 5.8 ± 3.5 (N = 5) |
| U73122 | Phospholipase C | 0.93 ± 0.6 (N = 5) |
| Piceatannol | Syk | 1 (N = 1) |

Discussion

Cell-electrode impedance reading is primarily influenced by three main parameters: the number of cells seeded on microelectronic sensor arrays, the shape of the cell and the strength of cell adhesion to the electrode surface. IgE-mediated RBL-2H3 mast cell activation is accompanied by an increase in effective surface area due to fusion of secretory granules, dramatic actin cytoskeleton rearrangement as well as an increase in integrin-mediated adhesion (Pfeiffer et al., 1985; Wyczolkowska et al., 1994). Morphological dynamics combined with an increase in adhesive interaction of the cell with the electrode surface leads to an increase in antigen-dependent IgE-mediated mast cell electrode impedance value. Furthermore, pharmacological inhibitors of signaling proteins which participate in IgE-mediated mast cell activation inhibit IgE-mediated mast cell activation in a dose-dependent manner (FIG. 17 and Table I).

According to the current paradigm for mast cell activation, antigen-mediated cross-linking of the IgE-bound Fc☐RI leads to phosphorylation of critical tyrosines in the immunoreceptor tyrosine-based activation motifs (ITAM) by Src family kinase, Lyn (Turner and Kinet, 1999). Phosphorylation of the ITAMS serves as a docking site for the Syk protein tyrosine kinase, which subsequently leads to its activation and phosphorylation of its downstream substrates such as phospholipase C gamma (PLCgamma). PLC☐gamma catalyzes the hydrolysis of membrane phospholipids to generate inositol 1,4,5-trisphosphate ($IP_3$) and diacylglycerol (DAG). $IP_3$ mobilizes calcium from internal reserves in the endoplasmic reticulum and both calcium and DAG lead to general activation of protein kinase C (PKC) family as well as other kinases and signaling proteins. Activation of IgE-mediated kinase pathways ultimately results in mast cell degranulation and release of inflammatory mediators. Accordingly pharmacological inhibitors of Src, Syk, PLCgamma and PKC led to a dose-dependent inhibition of IgE-mediated RBL-2H3 mast activation which can be monitored by the cell-electrode impedance measurement. The cell-electrode impedance values of the mast cells treated with these pharmacological inhibitors correlated with mast cell degranulation as measured by beta-hexosaminidase activity (FIG. 18). Utilization of these pharmacological inhibitors further validates this assay and indicates that the cell-substrate impedance monitoring system can be used to assess mast cell activation.

Several lines of recent evidence indicate that IgE-alone mediated interaction with mast cells has crucial biological functions that surpass its role as merely a sensitizer of mast cells (Kawakami and Galli, 2002). Two different groups have shown that application of monomeric IgE without antigen-mediated aggregation induces phosphorylation and activation of mitogen activated protein kinases (MAPKs) and AKT leading to enhanced mast cell survival (Asai et al., 2001; Kalesnikoff et al., 2001; Kitaura et al., 2003). However, the same papers also showed that monomeric IgE did not induce mast cell degranulation. In contrast, another recently published report indicates that high concentrations of monomeric IgE can induce mast cell activation in itself without the need for antigen-mediated ligation (Oka et al., 2004). According to the authors, IgE alone-mediated mast cell activation as measured by mediator release and actin cytoskeleton rearrangement was indistinguishable from antigen-mediated cross-linking (Oka et al., 2004). According to our results application of high concentrations of monomeric IgE alone also elicited an increase in mast cell-electrode impedance value, indicating mast cell activation (FIGS. 16A-B). However, the duration of the response was prolonged when compared to the antigen-mediated mast cell activation. While the molecular mechanism of antigen-independent and antigen-dependent mast cell activation response remains to be clarified, it is clear that monomeric IgE can illicit biologically important responses. We've also determined that the initial IgE concentration used to sensitize the cells ultimately determines the amplitude and duration of the subsequent antigen-mediated mast cell activation. Sensitization with high concentrations of IgE (1 microgram/mL) resulted in very low antigen-dependent mast cell response, while sensitization with low concentrations of IgE (15 nanogram/mL) resulted in mast cell response with much higher duration and amplitude (FIG. 16B). The lack of a significant antigen-mediated mast cell response with high concentration of IgE-sensitized mast cells more likely is due to the fact that mast cells have not had an opportunity to fully reform their secretory granules after IgE-mediated activation and this is supported by the fact that increasing the time increment between sensitization with 1 microgram/mL IgE and the cross-linking step will ultimately result in antigen-mediated mast cell activation.

In summary, the real-time and label-free IgE mediated mast cell activation assay described here should provide researchers in pharmaceutical industry as well as academia with a new and convenient tool to assess and quantify IgE-mediated mast cell activation. The adaptability of this assay to 96× microtiter plates with microelectronic sensors integrated in the bottom of the wells makes it ideal for high throughput analysis to screen large chemical compound libraries. Furthermore, microelectronic cell sensor technology in general can be used to assess other receptor ligand interactions.

All of the references cited herein, including patents, patent applications, and publications, and including references cited in the Bibliography, are incorporated by reference in their entireties.

Headings are for the convenience of the reader and do not limit the scope of the invention.

BIBLIOGRAPHY

Abbas, A. K. and Lichtman, A. H. (2000) Cellular and Molecular Immunology. In. Elseiver Science, p. 432-452.

Amon, U., von Stebut, E., Subramanian, N. and Wolff, H. H. (1993) CGP 41251, a novel protein kinase inhibitor with in vitro selectivity for protein kinase C, strongly inhibits immunological activation of human skin mast cells and human basophils. Pharmacology 47, 200-8.

Amoui, M., Draber, P. and Draberova, L. (1997) Src family-selective tyrosine kinase inhibitor, PP1, inhibits both Fc epsilonRI- and Thy-1-mediated activation of rat basophilic leukemia cells. Eur J Immunol 27, 1881-6.

Asai, K., Kitaura, J., Kawakami, Y., Yamagata, N., Tsai, M., Carbone, D. P., Liu, F. T., Galli, S. J. and Kawakami, T. (2001) Regulation of mast cell survival by IgE. Immunity 14, 791-800.

Corry, D. B. and Kheradmand, F. (1999) Induction and regulation of the IgE response. Nature 402, B18-23.

Demo, S. D., Masuda, E., Rossi, A. B., Throndset, B. T., Gerard, A. L., Chan, E. H., Armstrong, R. J., Fox, B. P., Lorens, J. B., Payan, D. G., Scheller, R. H. and Fisher, J. M. (1999) Quantitative measurement of mast cell degranulation using a novel flow cytometric annexin-V binding assay. Cytometry 36, 340-8.

Dietze, S. C., Auerswald, E. A. and Fritz, H. (1990) A new, highly sensitive enzymatic assay for human tryptase and its use for identification of tryptase inhibitors. Biol Chem Hoppe Seyler 371 Suppl, 65-73.

Giaever, I. and Keese, C. R. (1984) Monitoring fibroblast behavior in tissue culture with an applied electric field. Proc Natl Acad Sci USA 81, 3761-4.

Giaever, I. and Keese, C. R. (1986) Use of electric fields to monitor the dynamical aspect of cell behavior in tissue culture. IEEE Trans Biomed Eng 33, 242-7.

Giaever, I. and Keese, C. R. (1991) Micromotion of mammalian cells measured electrically. Proc Natl Acad Sci USA 88, 7896-900.

Giaever, I. and Keese, C. R. (1993) A morphological biosensor for mammalian cells. Nature 366, 591-2.

Gould, H. J., Sutton, B. J., Beavil, A. J., Beavil, R. L., McCloskey, N., Coker, H. A., Fear, D. and Smurthwaite, L. (2003) The biology of IGE and the basis of allergic disease. Annu Rev Immunol 21, 579-628.

Gurish, M. F. and Austen, K. F. (2001) The diverse roles of mast cells. J Exp Med 194, F1-5.

Hamid, Q., Tulic, M. K., Liu, M. C. and Moqbel, R. (2003) Inflammatory cells in asthma: mechanisms and implications for therapy. J Allergy Clin Immunol 111, S5-S12; discussion S12-7.

Holgate, S. T. and Broide, D. (2003) New targets for allergic rhinitis—a disease of civilization. Nat Rev Drug Discov 2, 902-14.

Kalesnikoff, J., Huber, M., Lam, V., Damen, J. E., Zhang, J., Siraganian, R. P. and Krystal, G. (2001) Monomeric IgE stimulates signaling pathways in mast cells that lead to cytokine production and cell survival. Immunity 14, 801-11.

Kawakami, T. and Galli, S. J. (2002) Regulation of mast-cell and basophil function and survival by IgE. Nat Rev Immunol 2, 773-86.

Kitaura, J., Song, J., Tsai, M., Asai, K., Maeda-Yamamoto, M., Mocsai, A., Kawakami, Y., Liu, F. T., Lowell, C. A., Barisas, B. G., Galli, S. J. and Kawakami, T. (2003) Evidence that IgE molecules mediate a spectrum of effects on mast cell survival and activation via aggregation of the FcepsilonRI. Proc Natl Acad Sci USA 100, 12911-6.

Lavens, S. E., Proud, D. and Warner, J. A. (1993) A sensitive colorimetric assay for the release of tryptase from human lung mast cells in vitro. J Immunol Methods 166, 93-102.

Lo, C. M., Keese, C. R. and Giaever, I. (1999) Cell-substrate contact: another factor may influence transepithelial electrical resistance of cell layers cultured on permeable filters. Exp Cell Res 250, 576-80.

Marone, G., Genovese, A., Granata, F., Forte, V., Detoraki, A., de Paulis, A. and Triggiani, M. (2002) Pharmacological modulation of human mast cells and basophils. Clin Exp Allergy 32, 1682-9.

Moriya, K., Rivera, J., Odom, S., Sakuma, Y., Muramato, K., Yoshiuchi, T., Miyamoto, M. and Yamada, K. (1997) ER-27319, an acridone-related compound, inhibits release of antigen-induced allergic mediators from mast cells by selective inhibition of fcepsilon receptor I-mediated activation of Syk. Proc Natl Acad Sci USA 94, 12539-44.

Noll, T., Dieckmann, D., Gibbs, B. F., Nitschke, M., Albrecht, C., Vollrath, I., Tamaoki, T., Wolff, H. H. and Amon, U. (1997) Heterogeneity of signal transduction mechanisms in human basophils and human skin mast cells. II. Effects of 7-O-methyl-UCN-01, NPC 15437 and bryostatin 1 and 2, four protein kinase C-modulatory agents, on mediator release. Biol Signals 6, 1-10.

Oka, T., Hori, M., Tanaka, A., Matsuda, H., Karaki, H. and Ozaki, H. (2004) IgE alone-induced actin assembly modifies calcium signaling and degranulation in RBL-2H3 mast cells. Am J Physiol Cell Physiol 286, C256-63.

Oliver, J. M., Burg, D. L., Wilson, B. S., McLaughlin, J. L. and Geahlen, R. L. (1994) Inhibition of mast cell Fc epsilon R1-mediated signaling and effector function by the Syk-selective inhibitor, piceatannol. J Biol Chem 269, 29697-703.

Oliver, J. M., Pfeiffer, J. R. and Wilson, B. S. (1997) Regulation and roles of the membrane, cytoskeletal and adhesive responses of RBL-2H3 rat tumor mast cells to Fc epsilon RI crosslinking. In: M. M. Hamawy (Ed) The High Affinity IgE Receptor FceRI Structure and Function. R. G. Landes, Austin, Tex., p. 139-172.

O'Luanaigh, N., Pardo, R., Fensome, A., Allen-Baume, V., Jones, D., Holt, M. R. and Cockcroft, S. (2002) Continual production of phosphatidic acid by phospholipase D is essential for antigen-stimulated membrane ruffling in cultured mast cells. Mol Biol Cell 13, 3730-46.

Pfeiffer, J. R., Seagrave, J. C., Davis, B. H., Deanin, G. G. and Oliver, J. M. (1985) Membrane and cytoskeletal changes associated with IgE-mediated serotonin release from rat basophilic leukemia cells. J Cell Biol 101, 2145-55.

Powner, D. J., Hodgkin, M. N. and Wakelam, M. J. (2002) Antigen-stimulated activation of phospholipase D1b by Rac1, ARF6, and PKCalpha in RBL-2H3 cells. Mol Biol Cell 13, 1252-62.

Razin, E., Mencia-Huerta, J. M., Stevens, R. L., Lewis, R. A., Liu, F. T., Corey, E. and Austen, K. F. (1983) IgE-mediated release of leukotriene C4, chondroitin sulfate E proteoglycan, beta-hexosaminidase, and histamine from cultured bone marrow-derived mouse mast cells. J Exp Med 157, 189-201.

Rivera, J. (2002) Molecular adapters in Fc(epsilon)RI signaling and the allergic response. Curr Opin Immunol 14, 688-93.

Satomura, K., Shimizu, S., Nagato, T., Komeichi, H., Osuga, M., Katsuta, Y., Aramaki, T. and Omoto, Y. (2002) Establishment of an assay method for human mast cell chymase. Hepatol Res 24, 361-367.

Shichijo, M., Yamamoto, N., Tsujishita, H., Kimata, M., Nagai, H. and Kokubo, T. (2003) Inhibition of syk activity and degranulation of human mast cells by flavonoids. Biol Pharm Bull 26, 1685-90.

Smith, T. J., Wang, H. S., Hogg, M. G., Henrikson, R. C., Keese, C. R. and Giaever, I. (1994) Prostaglandin E2 elicits a morphological change in cultured orbital fibroblasts from patients with Graves ophthalmopathy. Proc Natl Acad Sci USA 91, 5094-8.

Tedeschi, A., Lorini, M., Gibelli, S. and Miadonna, A. (2000) Effects of protein kinase C and phospholipase C inhibitors on IgE-dependent and IgE-independent basophil histamine release. Inflamm Res 49, 480-5.

Turner, H. and Kinet, J. P. (1999) Signalling through the high-affinity IgE receptor Fc epsilonRI. Nature 402, B24-30.

Wang, H. S., Keese, C. R., Giaever, I. and Smith, T. J. (1995) Prostaglandin E2 alters human orbital fibroblast shape through a mechanism involving the generation of cyclic adenosine monophosphate. J Clin Endocrinol Metab 80, 3553-60.

Wyczolkowska, J., Dastych, J., Slusarczyk, A. and Kolago, B. (1994) Relations between Fc epsilon RI crosslinking-induced mast cell activation and adhesion to fibronectin. J Physiol Pharmacol 45, 501-16.

Yamamoto, N., Takeshita, K., Shichijo, M., Kokubo, T., Sato, M., Nakashima, K., Ishimori, M., Nagai, H., Li, Y. F., Yura, T. and Bacon, K. B. (2003) The orally available spleen tyrosine kinase inhibitor 2-[7-(3,4-dimethoxyphenyl)-imidazo[1,2-c]pyrimidin-5-ylamino]nicotinamide dihydrochloride (BAY 61-3606) blocks antigen-induced airway inflammation in rodents. J Pharmacol Exp Ther 306, 1174-81.

What is claimed is:

1. A method for identifying a target for modulating cellular responses to IgE stimulation, the method comprising:
   a) providing an impedance-based system that monitors cell-substrate impedance of cells on a substrate;
   b) introducing cells into the system, wherein the cells are genetically modified to alter a function of, or reduce or ablate expression of, a suspected target molecule;
   c) adding IgE to the cells;
   d) adding an antigen to the cells;
   e) monitoring cell-substrate impedance of the cells on the substrate;
   f) analyzing cell-substrate impedance data compared to control cells that are not genetically modified to identify a target for modulation of cellular responses to IgE stimulation.

2. The method of claim 1, wherein the cells are primary cells.

3. The method of claim 1, wherein the cells are selected from the group consisting of mast cells, eosinophils, basophils, and genetically engineered cells.

4. The method of claim 1, wherein one or more compounds for genetically modifying the cells are added to the cells prior to the step of adding IgE.

5. The method of claim 1, wherein cell-substrate impedance is monitored before the step of adding the IgE to the cells.

6. The method of claim 1, wherein the cell-substrate impedance is monitored after the step of adding the IgE to the cells.

7. The method of claim 1, wherein the cell-substrate impedance is monitored before and after the step of adding the IgE to the cells.

8. The method of claim 7, wherein said cell-substrate impedance is monitored before and after the step of adding the antigen to the cells.

9. A method for comparing responses to IgE stimulation between cells of different genotypes, the method comprising:
   a) providing an impedance-based system that monitors cell-substrate impedance of cells on a substrate;
   b) introducing cells of two different genotypes to the substrate of the system to form two different genotype cell populations;
   c) adding IgE to the cells of both genotypes;
   d) adding an antigen to the cells of both genotypes;
   e) monitoring cell-substrate impedance of the cells of both genotypes on the substrate; and
   f) comparing the cell-substrate impedances between the cells of different genotypes.

10. The method of claim 9, wherein the cells of two different genotypes are primary cells from human subjects.

11. The method of claim 9, wherein the antigen is a known or suspected allergen.

12. The method of claim 9, further comprising correlating the cell-substrate impedances with molecular genetic data obtained from the different genotypes.

13. The method of claim 12, wherein the molecular genetic data is selected from one or more of the group consisting of RFLIP data, SNP data, DNA marker data, RNA expression profiling data, protein expression profiling data, and alternative splicing data.

14. A method for identifying an antigen or half antigen that can cause an allergic response, the method comprising:
   a) providing an impedance-based system that monitors cell-substrate impedance of cells on a substrate;
   b) introducing cells to the substrate of the system;
   c) adding IgE to the cells;
   d) adding at least one compound suspected of being an antigen or half antigen to the cells;
   e) monitoring cell-substrate impedance of cells on the substrate to obtain cell-substrate impedance data of the cells treated with the antigen or the half antigen; and
   f) analyzing the data to identify whether the compound is an antigen or half antigen.

15. The method of claim 14, wherein the substrate is positioned in an incubator.

* * * * *